(12) United States Patent
Rimsa et al.

(10) Patent No.: US 9,446,189 B2
(45) Date of Patent: Sep. 20, 2016

(54) TISSUE TRANSFER SYSTEMS

(71) Applicant: LifeCell Corporation, Branchburg, NJ (US)

(72) Inventors: Joseph Rimsa, Palo Alto, CA (US); Brian J. Domecus, San Francisco, CA (US); Christopher S. Jones, Menlo Park, CA (US); Paul James Lingane, Redwood City, CA (US)

(73) Assignee: LifeCell Corporation, Branchburg, NJ (US)

( * ) Notice: Subject to any disclaimer, the term of this patent is extended or adjusted under 35 U.S.C. 154(b) by 0 days.

(21) Appl. No.: 13/743,039

(22) Filed: Jan. 16, 2013

(65) Prior Publication Data

US 2013/0131635 A1 May 23, 2013

Related U.S. Application Data

(63) Continuation of application No. 13/664,925, filed on Oct. 31, 2012, now Pat. No. 8,632,498, which is a continuation-in-part of application No. 13/371,270, filed on Feb. 10, 2012.

(60) Provisional application No. 61/442,060, filed on Feb. 11, 2011, provisional application No. 61/510,967, filed on Jul. 22, 2011.

(51) Int. Cl.
- *A61M 5/145* (2006.01)
- *A61L 27/36* (2006.01)
- *A61M 5/168* (2006.01)

(52) U.S. Cl.
CPC ......... *A61M 5/1452* (2013.01); *A61L 27/3604* (2013.01); *A61L 2400/06* (2013.01); *A61L 2430/04* (2013.01); *A61L 2430/34* (2013.01); *A61M 2005/16863* (2013.01)

(58) Field of Classification Search
CPC ................ A61M 5/1452; A61M 2005/16863; A61L 27/3604; A61L 2430/34; A61L 2400/06; A61L 2430/04
USPC .......... 604/67, 121, 131, 151, 152, 246, 506
See application file for complete search history.

(56) References Cited

U.S. PATENT DOCUMENTS

| | | |
|---|---|---|
| 4,753,634 A | 6/1988 | Johnson |
| D401,336 S | 11/1998 | Muller et al. |

(Continued)

OTHER PUBLICATIONS

Yoshimura et al., Cell-Assisted Lipotransfer for Cosmetic Breast Augmentation: Supportive Use of Adipose-Derived Stem/Stromal Cells, Aesthetic Plastic Surgery Journal, vol. 32, pp. 48-55, Sep. 2007.

*Primary Examiner* — Theodore Stigell
(74) *Attorney, Agent, or Firm* — McCarter & English, LLP; Matthew R. Van Eman

(57) ABSTRACT

Devices and methods for tissue transfer are described where a cannula may be inserted into the breast of a subject at one of several points of entry. Insertion of the cannula into the breast may be accomplished by using a guidance system to distinguish between tissue types. Once desirably positioned, the cannula may be withdrawn from the breast while automatically (or manually) injecting the fat in multiple deposits of adipose tissue or fat such that the deposited fat remains within the tract formed by the withdrawn cannula. Multiple tracts of the deposited fat may be injected within the breast until the breast has been desirably remodeled and/or augmented.

33 Claims, 67 Drawing Sheets

(56) References Cited

U.S. PATENT DOCUMENTS

| | | |
|---|---|---|
| D424,194 S | 5/2000 | Holdaway et al. |
| 6,258,054 B1 | 7/2001 | Mozsary et al. |
| D492,995 S | 7/2004 | Rue et al. |
| D575,393 S | 8/2008 | Stephens |
| 7,588,732 B2 | 9/2009 | Buss |
| 7,780,649 B2 | 8/2010 | Shippert |
| 7,789,872 B2 | 9/2010 | Shippert |
| 7,794,449 B2 | 9/2010 | Shippert |
| 8,062,286 B2 | 11/2011 | Shippert |
| 8,293,532 B2 | 10/2012 | Moynahan |
| 8,333,740 B2 | 12/2012 | Shippert |
| D679,011 S | 3/2013 | Kitayama et al. |
| 8,409,860 B2 | 4/2013 | Moynahan |
| D683,851 S | 6/2013 | Greenhalgh |
| D687,549 S | 8/2013 | Johnson et al. |
| D692,559 S | 10/2013 | Scheibel et al. |
| 8,622,997 B2 | 1/2014 | Shippert |
| 8,632,498 B2 | 1/2014 | Rimsa et al. |
| 2008/0167613 A1 | 7/2008 | Khouri et al. |
| 2009/0181104 A1* | 7/2009 | Rigotti et al. ............. 424/574 |
| 2009/0299328 A1* | 12/2009 | Mudd et al. ............. 604/506 |
| 2010/0268189 A1* | 10/2010 | Byrnes et al. ............. 604/506 |

\* cited by examiner

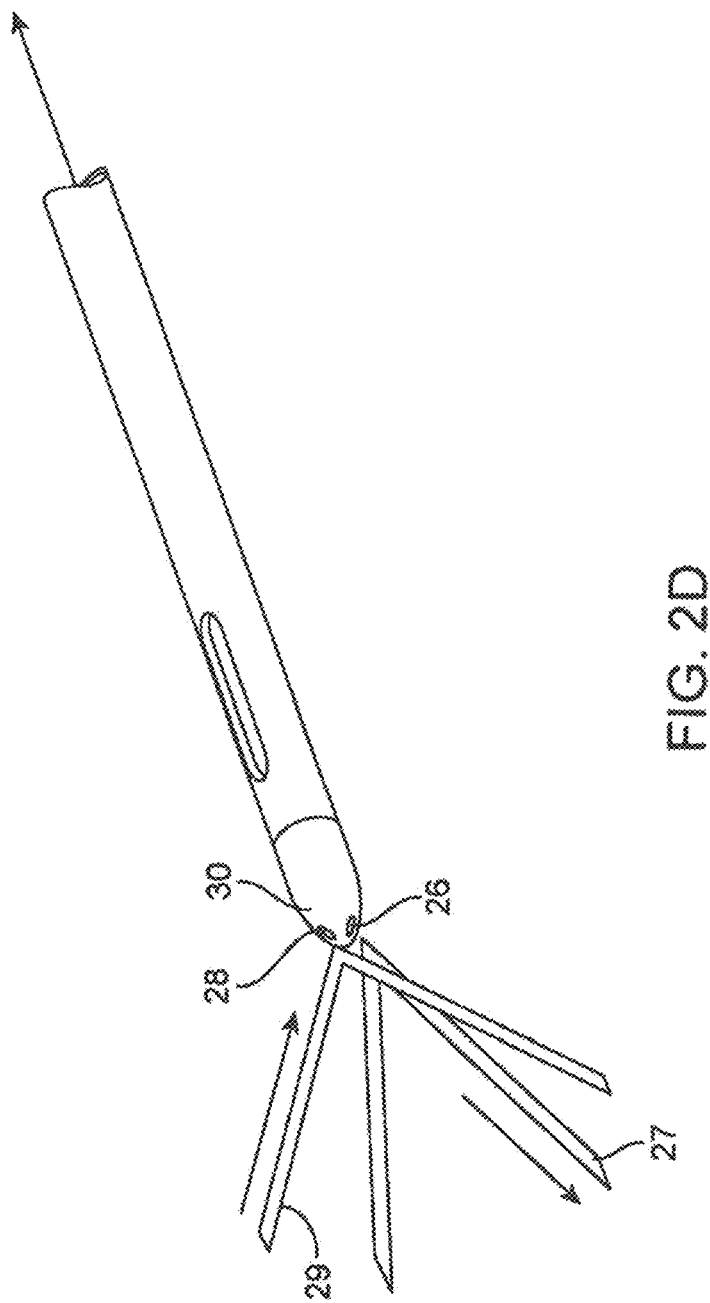

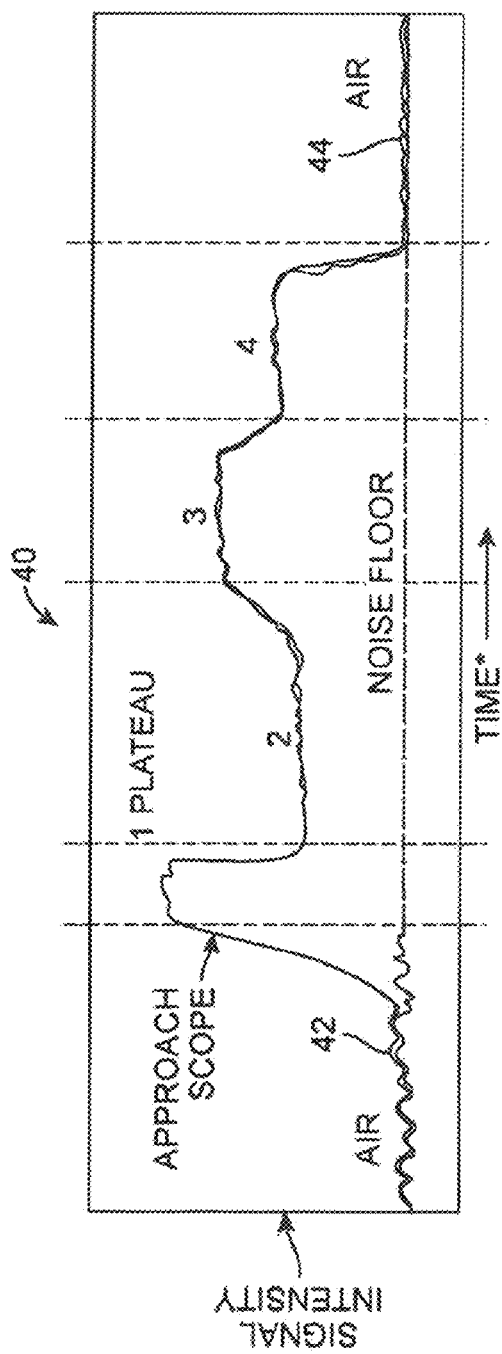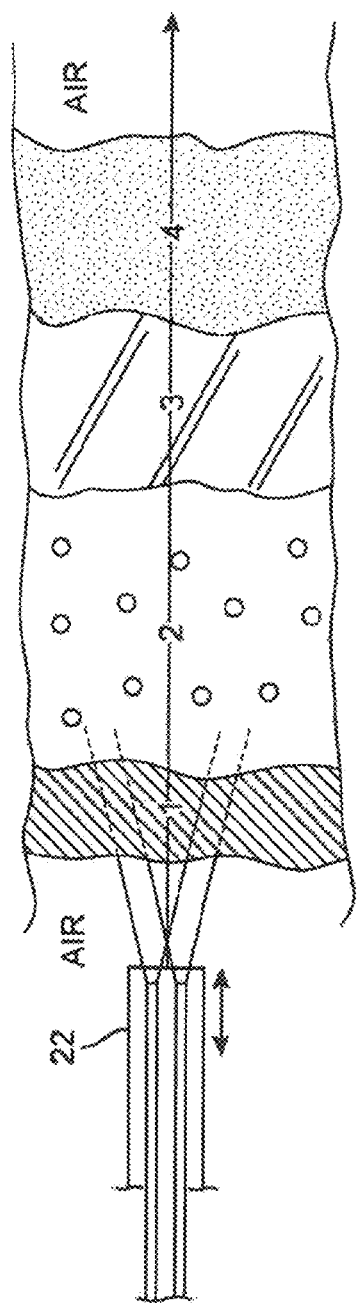

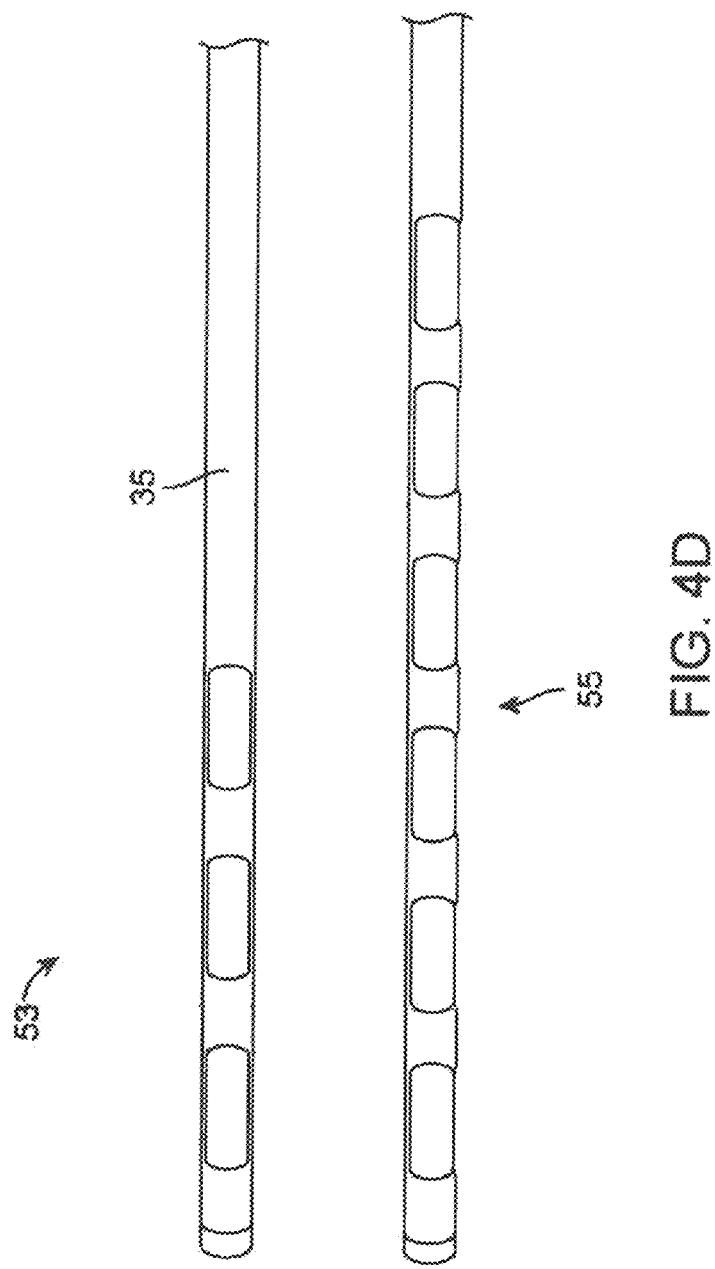

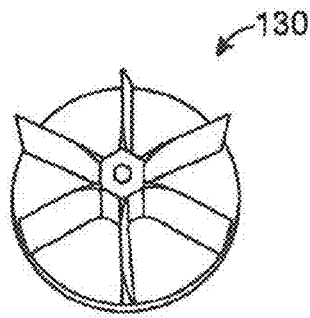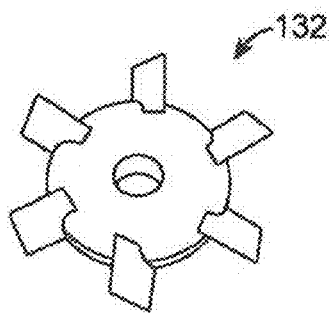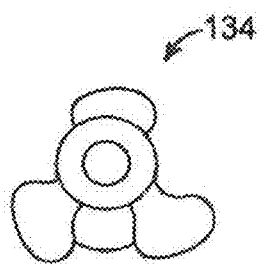
FIG. 12A  FIG. 12B  FIG. 12C
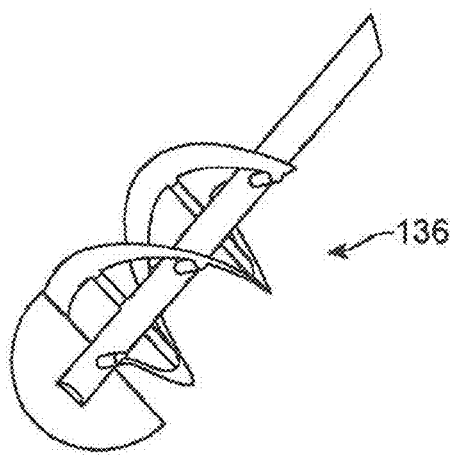
FIG. 12D
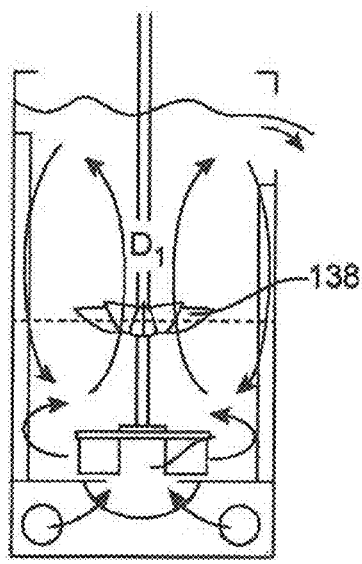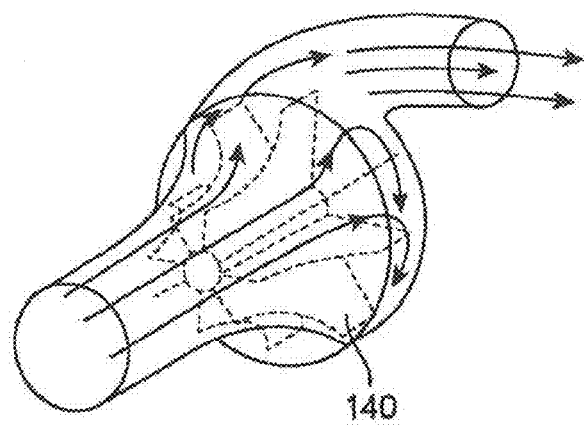
FIG. 12E  FIG. 12F

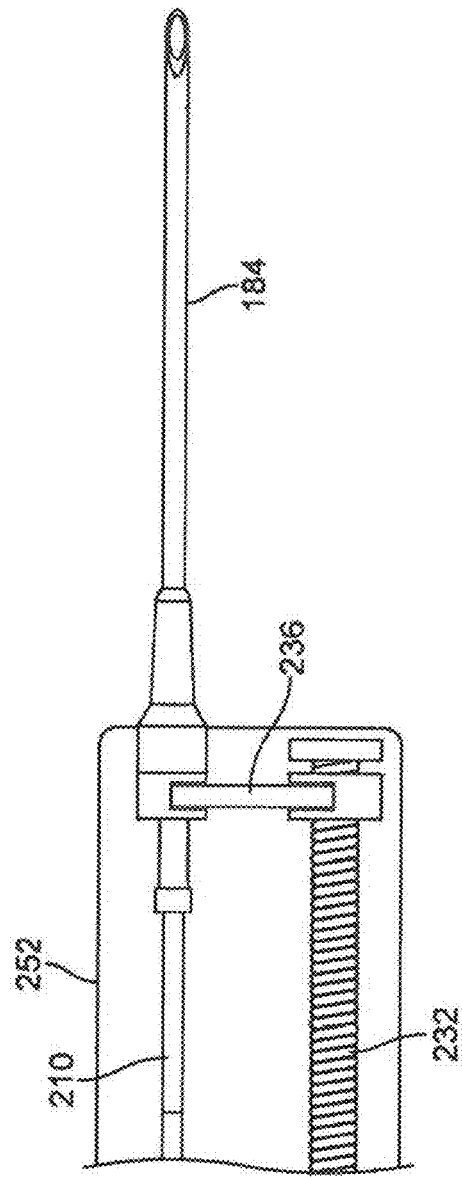
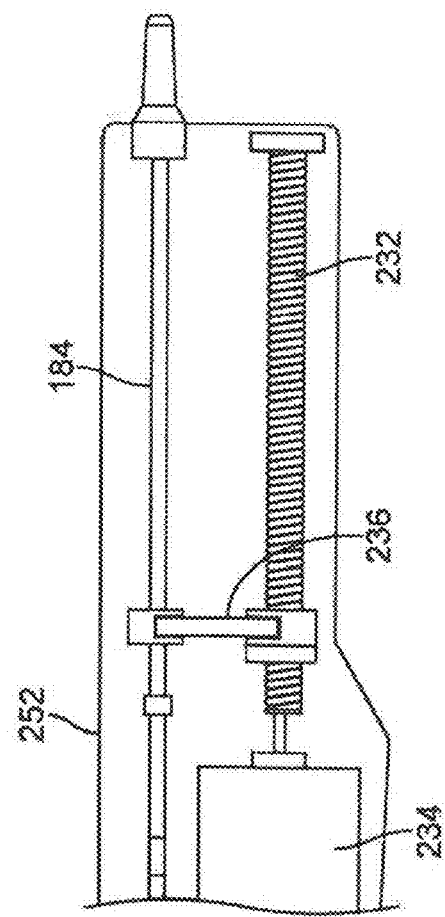
FIG. 25A
FIG. 25B

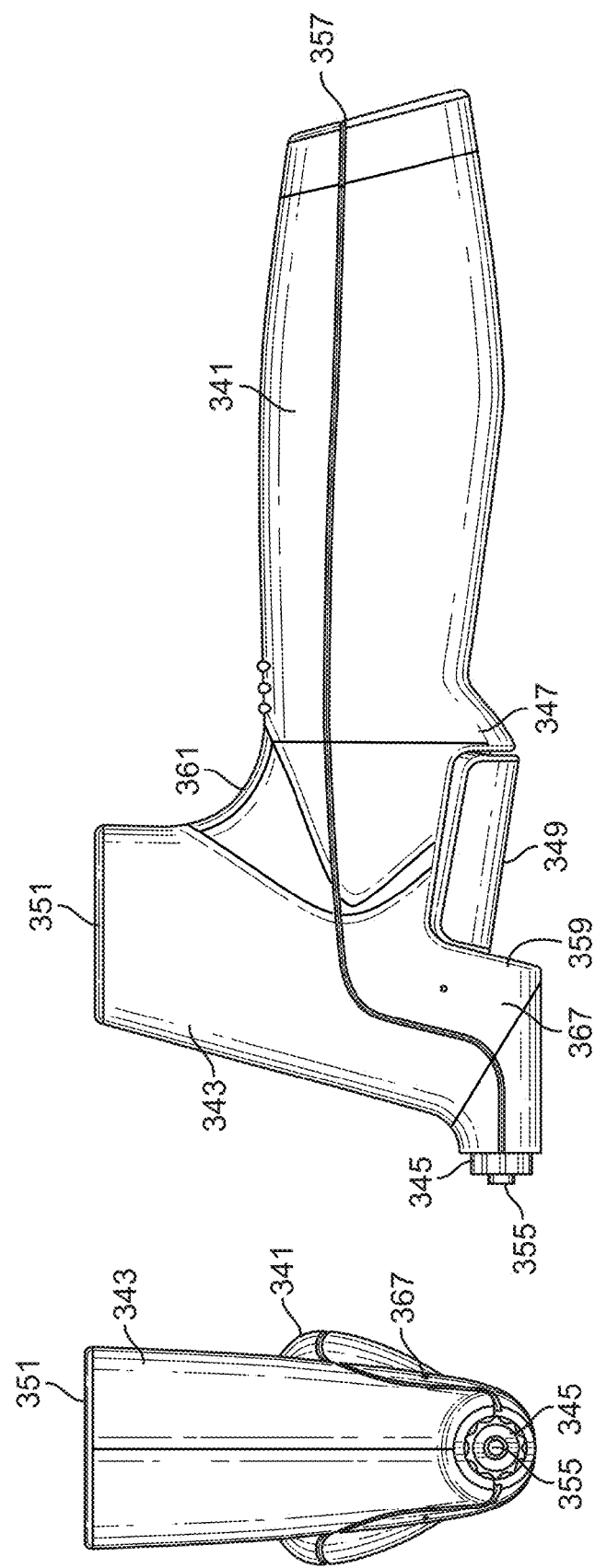

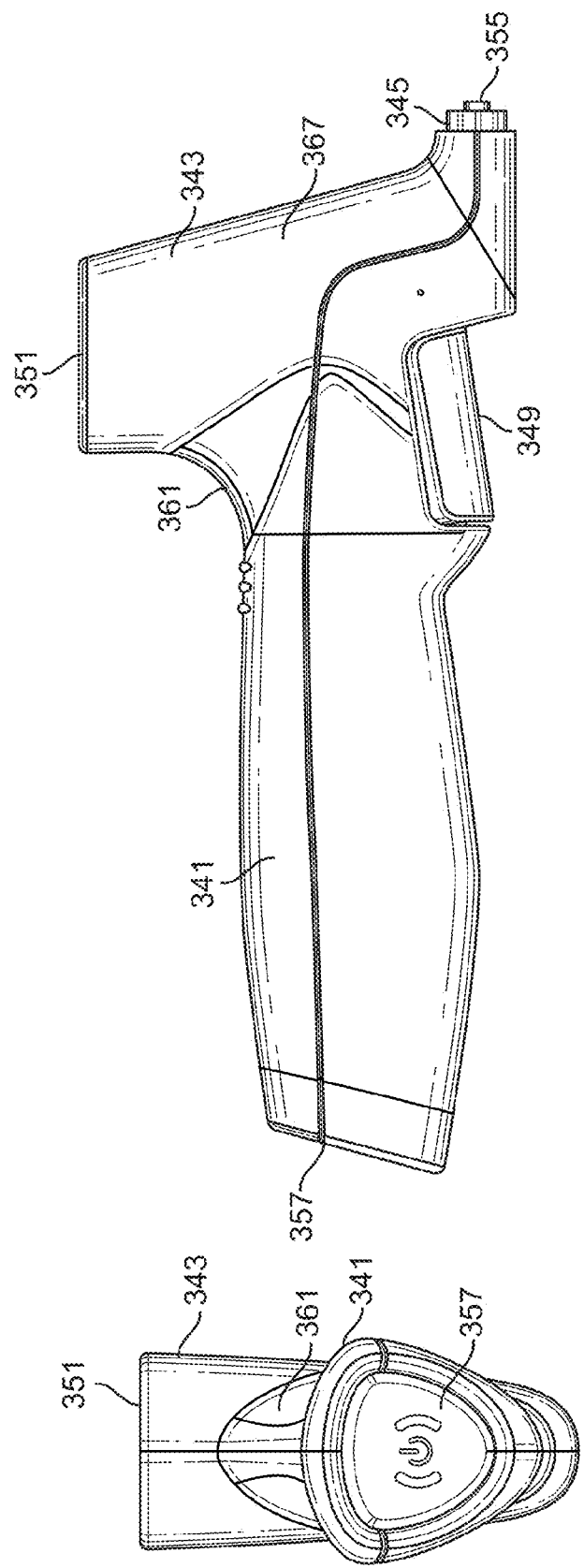

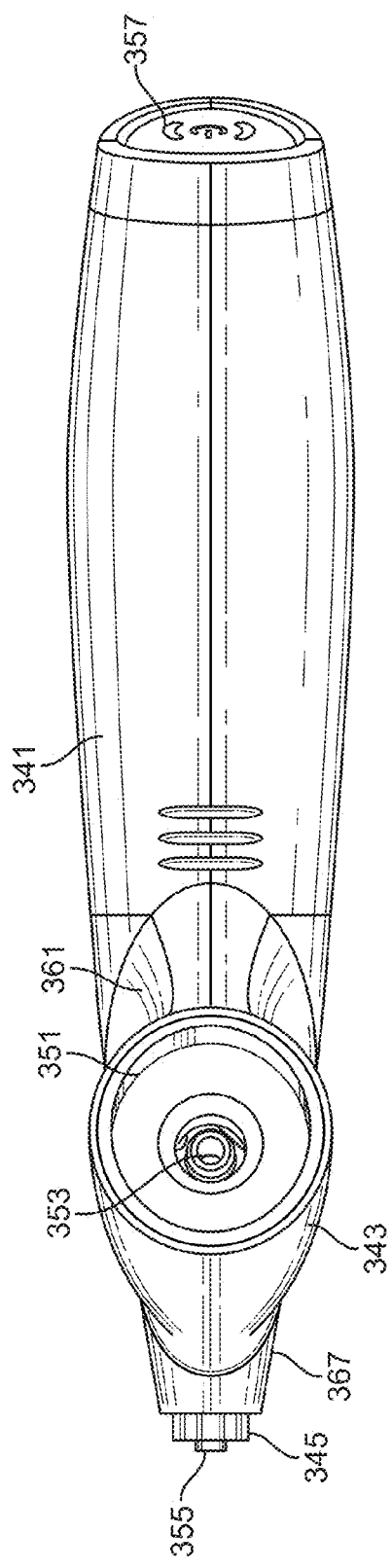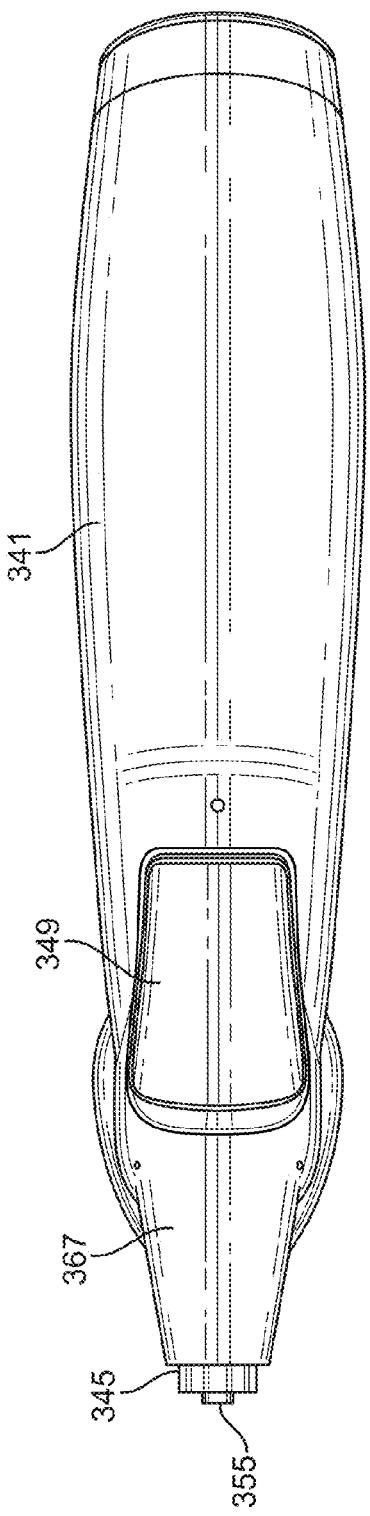

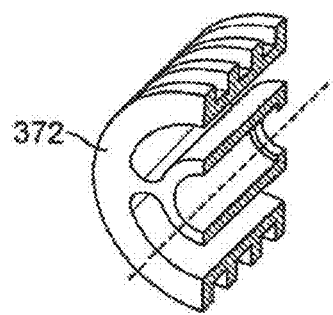
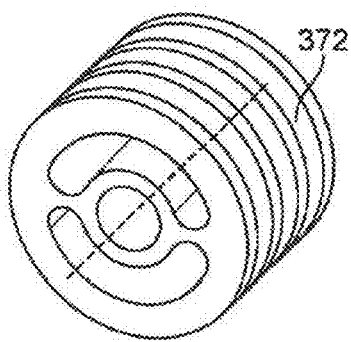
FIG. 42A    FIG. 42B
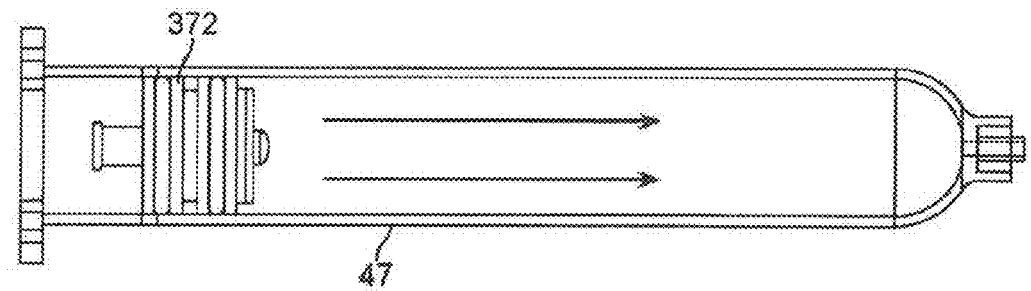
FIG. 43
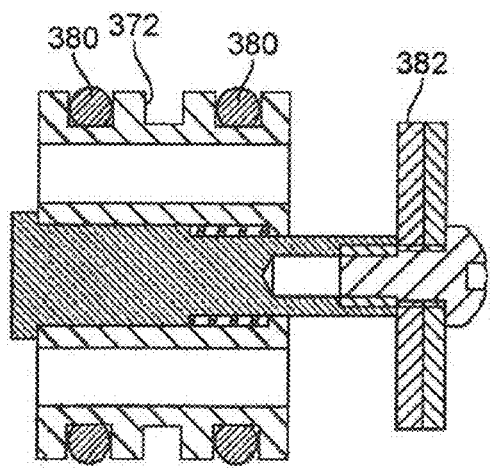
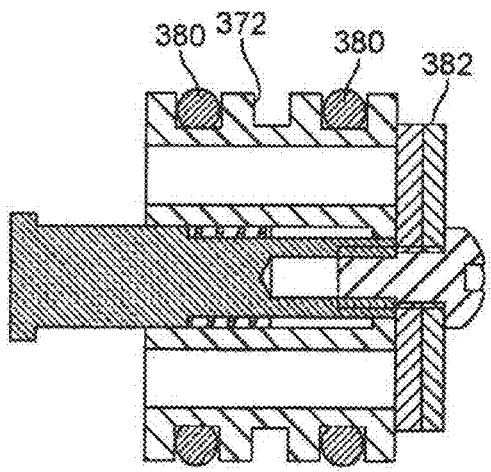
FIG. 44A    FIG. 44B

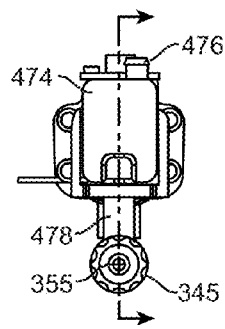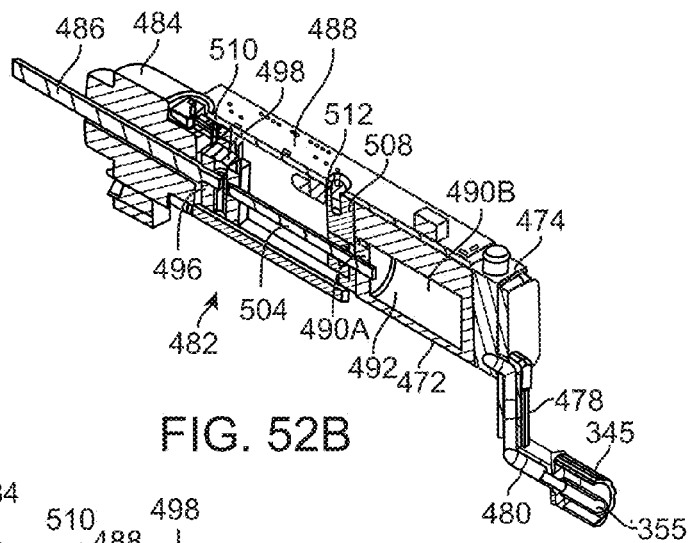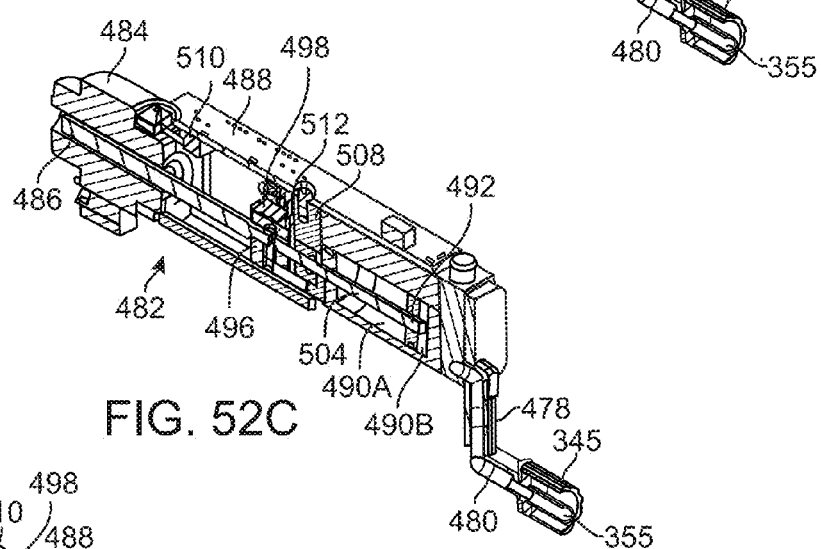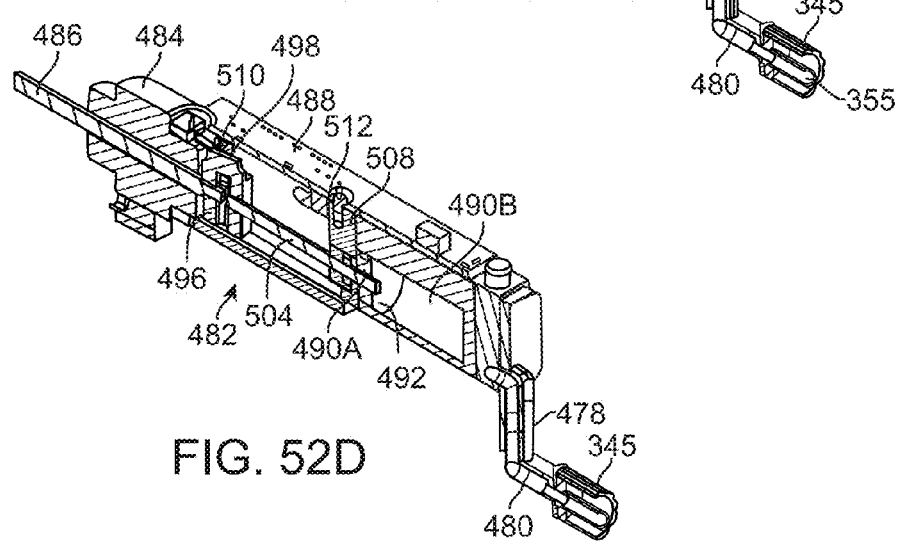

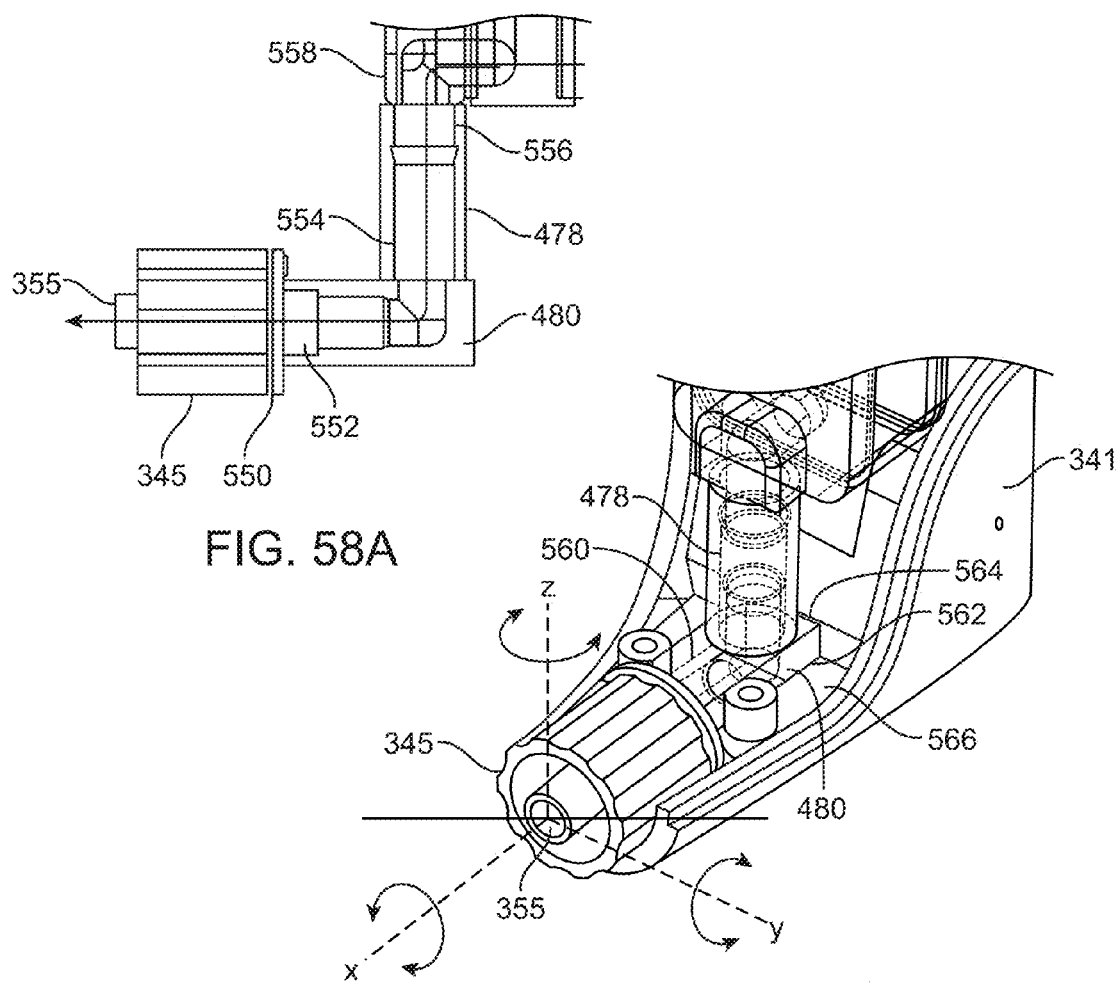
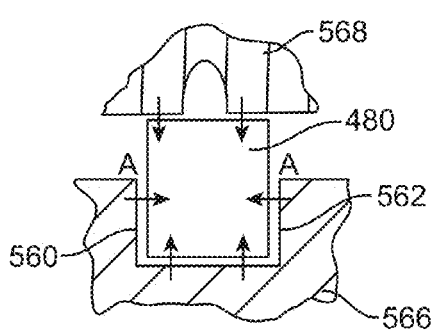
FIG. 58A
FIG. 58B
FIG. 58C

TISSUE TRANSFER SYSTEMS

CROSS-REFERENCE TO RELATED APPLICATIONS

This application is a continuation of U.S. patent application Ser. No. 13/664,925 filed Oct. 31, 2012, which is a continuation-in-part of U.S. patent application Ser. No. 13/371,270 filed Feb. 10, 2012 which claims the benefit of priority to U.S. Prov. App. Nos. 61/442,060 filed Feb. 11, 2011; 61/489,811 filed May 25, 2011; and 61/510,967 filed Jul. 22, 2011, each of which is incorporated herein by reference in its entirety.

FIELD OF THE INVENTION

The present invention relates generally to medical devices and methods used for transferring tissue into a region of the body. More particularly, the present invention relates to apparatus and methods for transferring fat tissue into a region of the body, such as a breast, in a selectively controlled manner.

BACKGROUND OF THE INVENTION

Lipomodeling is a procedure which is typically performed under general anesthesia. Adipose tissue or fat is usually harvested from one part of the body such as the abdomen, buttocks, thighs, etc., and purified to obtain the adipocytes. The purified adipocytes or fat is then injected directly into a targeted region of the subject's body, for example, to treat the face or breasts for augmentation or treatment of abnormalities. In treating the breasts, the fat is typically injected, e.g., a volume of 100-250 mL per breast, via 10-mL syringes directly into the breast and deposited along multiple micro-tunnels to build up or remodel the breast.

Examples of such procedures are described in *Fat Injection to the Breast: Technique, Results, and Indications Based on* 880 *Procedures Over* 10 *Years*, Delay, Emmanuel et al., Aesthetic Surgery Journal, vol. 29, no. 5, 360-376, September/October 2009; *Cell-Assisted Lipotransfer for Cosmetic Breast Augmentation: Supportive Use of Adipose-Derived Stem/Stromal Cells*, Yoshimura, Kotaro et al., Aesth. Plast. Surg., vol. 32, 48-55, September 2007; and *Fat Grafting to the Breast Revisited: Safety and Efficacy*, Coleman, Sydney et al., Plastic and Reconstructive Surgery, vol. 119, no. 3: 775-785, March 2007, each of which is incorporated herein by reference in its entirety.

During injection of the adipocyte material, the physician will typically inject small, discrete quantities into the patient body using a Byron-Coleman type re-usable injection cannula. However, this technique is subject to variability in physician technique potentially resulting in inconsistent results and is also subject to improper placement of the adipose tissue into undesirable regions within the breast.

The regions within the breast which are ideally avoided by the physician, such as the muscles or ducts of the breast, may be difficult to discern while the desirable locations for injecting the fat (located between the pectoral muscles and breast ducts) are also difficult to detect. Prior attempts to accurately position the cannula for injection into the ideal locations within the breasts have been made but they have faced difficulties in use and adoption. Examples are described in, e.g., *A New Technique to Assist Epidural Needle Placement*, Ting, Chien-Kun et al., Anesthesiology, vol. 112, no. 5: 1128-35, May 2010, which is incorporated herein by reference in its entirety.

There remains a need for the application of greater volumes implanted into the breast as well as improved instruments and methods to better enable fat harvesting, purification, and/or implantation of the fat. Additionally, there remains a need for instruments having improved guidance for the precision placement of viable adipocyte grafts in the breast relative to the surrounding breast tissue.

SUMMARY OF THE INVENTION

A cannula may be inserted into the breast of a subject at one of several points of entry. After insertion of the cannula into the breast, the cannula may be withdrawn from the breast while injecting the fat in multiple deposits of adipose tissue or fat such that the deposited fat remains within the tract formed by the withdrawn cannula. Multiple tracts of the deposited fat may be injected within the breast until the breast has been desirably remodeled and/or augmented.

To properly position the cannula within the breast for injection of the fat, an instrument assembly utilizing diffuse reflectance may be incorporated and may generally comprise a cannula optically coupled to a light source, e.g., laser, etc. via an optical transmission fiber which is positioned through or adjacent to the cannula. A distal end of the transmission fiber may emit a light from the distal end of the cannula such that any light reflected by tissue in proximity to the distal end may be detected by the distal end of an optical receiving fiber The receiving fiber may be optically coupled to a photo detector which may in turn by electrically coupled to a processor and a display for use by the physician.

By transmitting a light (such as laser light having a wavelength of between 600 to 1550 µm) via the transmission fiber onto the tissue, the backscattered reflected light may be detected by photo detector at a detection range matching that of the transmitted laser output. By having the processor differentiate between the different light scattering properties of the tissue, the physician can determine whether the cannula is located within or away from a particular anatomical structure for injecting or refraining from injecting the adipose tissue With the detection of tissue types utilizing diffuse reflectance, the assembly may be programmed by processor to automatically inject and/or cease injection of the fat from the cannula into the breast depending upon the type of tissue detected. By utilizing a closed-loop system, as the cannula is advanced or withdrawn from the breast, the different tissue types may be automatically detected by processor. When the present of fat is detected, cannula may automatically inject the fat from cannula in a controlled volume and injection rate.

Aside from tissue identification, the cannula assembly may also be used for harvesting of the fat as well as injection into the body. An optionally detachable harvesting cannula may be introduced into a region of the body containing fat to be harvested. The fat may be aspirated or otherwise drawn into the harvesting cannula and collected into a harvesting reservoir assembly having one or more individual cartridges. The collected fat may be processed individually or collectively and this processed fat may be fluidly coupled directly to the handle with yet another detachable injection cannula.

In addition to the detection of tissue types for facilitating the accurate injection of the fat, various instruments may be utilized within or in conjunction with the cannula for delivering precise volumes of the fat in a controlled manner. One example is a screw-type injection mechanism having a fluted shaft. The screw mechanism may be rotatably positioned within the cannula and it may have a distal opening for injecting the fat delivered through the cannula. As the screw mechanism rotates, any fat contained within a connected reservoir or within the cannula itself may be meted out through the distal opening. Starting or stopping the injection of the fat may be accurately controlled by starting or stopping rotation of the mechanism. An optional retractable cover located along the distal end of the cannula may be used as well.

An entry port may be positioned along the handle in proximity to the proximal end of screw mechanism such that fat for injection introduced into the handle may be taken up by the mechanism. The entry port may open into a chamber which is in fluid communication with the cannula and screw mechanism to minimize any clogging or obstruction which may occur due to the fat. Additionally and/or optionally, bristle stop members may be incorporated within the cannula lumen to further minimize or inhibit any clogging of the fat during injection into the patient.

In yet another variation, the injection assembly may optionally incorporate an impeller-stator assembly within the housing of the handle to help accelerate the fat to a speed sufficient for injection as well as to uniformly dispense the fat through the cannula for uniform injection into the breast. In use, as the impeller rotates via a drive shaft, the fat contained within the housing or reservoir may be propelled distally through the assembly past the blades of the stator which remains static. As the fat is urged through the assembly, the flow may be uniform as it is urged through the cannula for injection into the breast tissue.

Another variation may include a fat introduction chamber having a first diameter D1 from which the cannula extends having a second diameter D2 where the diameter of D1 is about twice the diameter of D2. In this variation, the chamber may optionally incorporate a plunger to pressurize the fat for injection through the cannula while the mechanism rotates to eject the fat.

In yet another variation, a plunger may be positioned within the housing to extend into a proximal portion of the cannula. With the cannula filled with a quantity of fat, the cannula may be advanced percutaneously into the breast while under guidance. Once a suitable location has been located within the breast, the housing and plunger may both be maintained in a static position relative to the breast while the cannula may be retracted into the housing through the opening in the housing relative to the breast proximally. Because the plunger remains static relative to the cannula, the fat contained within the cannula lumen may be forced out through the distal opening such that the ejected fat is deposited along the tract previously formed by the cannula within the tissue.

Other mechanisms may incorporate a pressure actuated system in which a piston is slidable through the housing by introducing a gas or fluid into a proximal or distal inlet to urge the piston proximally within the housing thereby retracting cannula or distally out of the housing.

Instead of utilizing a pressure driven assembly, another injection assembly variation may use a linear threaded member which is rotatably coupled to a motor positioned within a housing. Here, the motor may rotate the threaded member in either direction to urge a carriage which is threaded in a corresponding manner to move distally or proximally along the threaded member depending upon the direction of rotation by the threaded member. The carriage may be attached to a proximal end of the cannula such that as the carriage travels along the threaded member the cannula may be retracted or extended as desired.

BRIEF DESCRIPTION OF THE DRAWINGS

FIG. 2D shows a perspective view of an example of an injection cannula having the light transmission and light receiving fibers within the distal end for tissue characterization.

FIG. 3A shows an example of the variance in signal intensity upon encountering different tissue types for facilitating the selective deposition of adipose tissue.

FIG. 3B shows a cross-sectional side view of an instrument which may be guided via the signal variance for selectively depositing the adipose tissue.

FIG. 4D show side views of various harvesting cannulas.

FIGS. 12A to 12F show examples of various impeller configurations which may be used with the injection instrument.

FIGS. 25A and 25B show detail side views of the retractable needle cannula mechanism.

FIGS. 36A to 36J show various views of yet another variation of a handle assembly which may be configured as a portable and self-contained device.

FIGS. 42A and 42B show cross-sectional side and perspective views of one variation of a plunger defining one or more openings therethrough.

FIG. 43 shows a side view of a cartridge having a plunger and valve assembly incorporated.

FIGS. 44A and 44B show cross-sectional side views of a plunger and valve assembly illustrating an open and closed configuration.

FIG. 52A shows an end view of the pump assembly of FIG. 51A.

FIGS. 52B to 52D show the pump assembly of FIG. 51A with the handle housing removed for clarity.

FIGS. 58A and 58B show a detail side and perspective views of the angled channel and luer block within the handle assembly.

FIG. 58C shows an end view of the luer block contained within the handle assembly.

DETAILED DESCRIPTION OF THE INVENTION

Figure 1A:
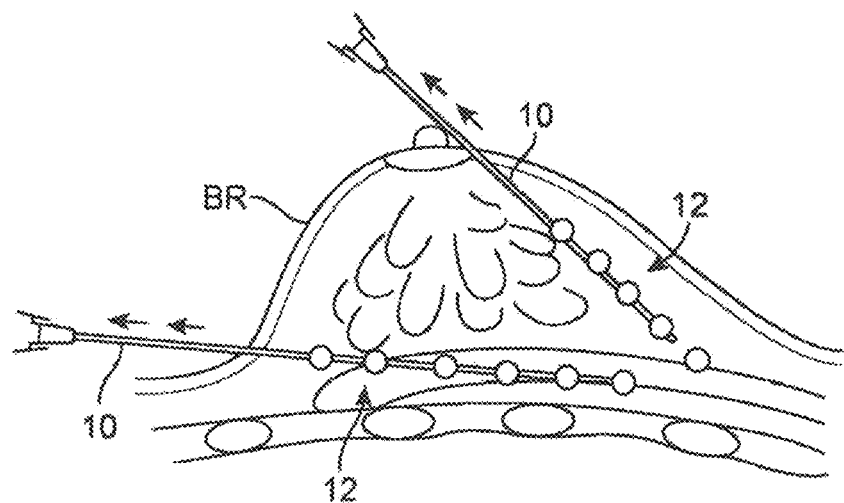
FIG. 1A shows a cross-sectional side view of a cannula inserted into a breast of a subject and depositing adipose tissue.
Figure 1B:
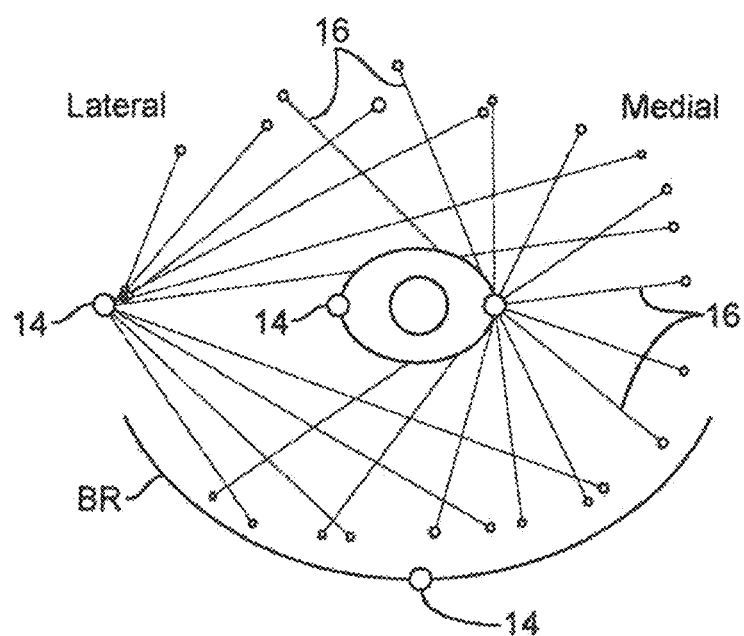
FIG. 1B shows an anterior view of a representative breast and possible percutaneous entry points and pathways for depositing adipose tissue.

As shown in the cross-sectional side view and anterior view of FIGS. 1A and 1B, a cannula 10 may be inserted into the breast BR of a subject at one of several points of entry 14 in proximity to the nipple and circumference of the breast BR. After insertion of the cannula 10 into the breast, the cannula 10 may be withdrawn from the breast BR while injecting the fat in multiple deposits of adipose tissue or fat 12 such that the deposited fat 12 remains within the tract 16 formed by the withdrawn cannula 10. Multiple tracts 16 of the deposited fat 12 may be injected within the breast utilizing the common entry points 14 until the breast has been desirably remodeled and/or augmented.

Figure 1C:
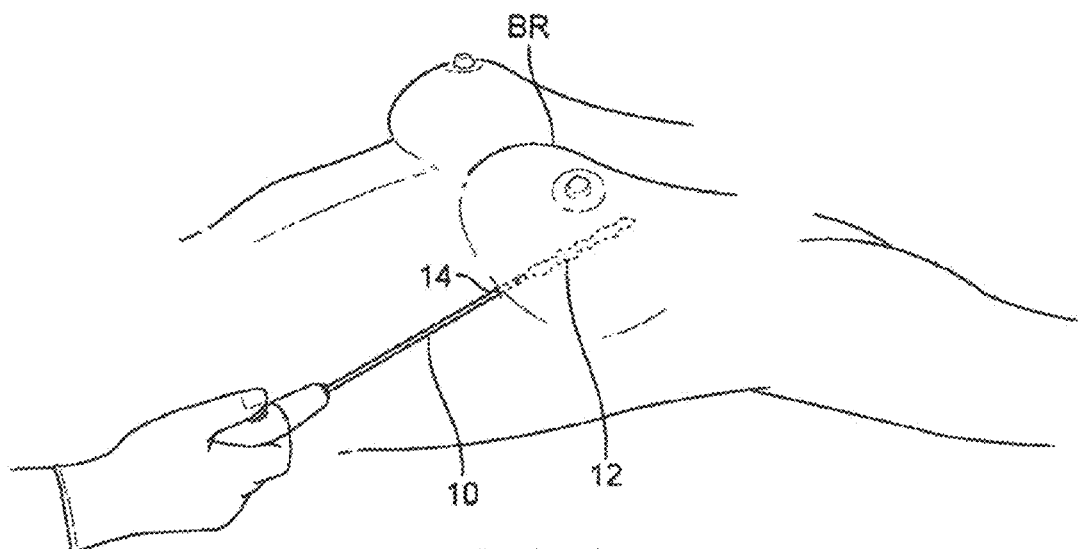
FIGS. 1C and 1D show examples of how the cannula may be inserted through a single entry point beneath a breast for remodeling the breast with deposited fat.
Figure 1D:
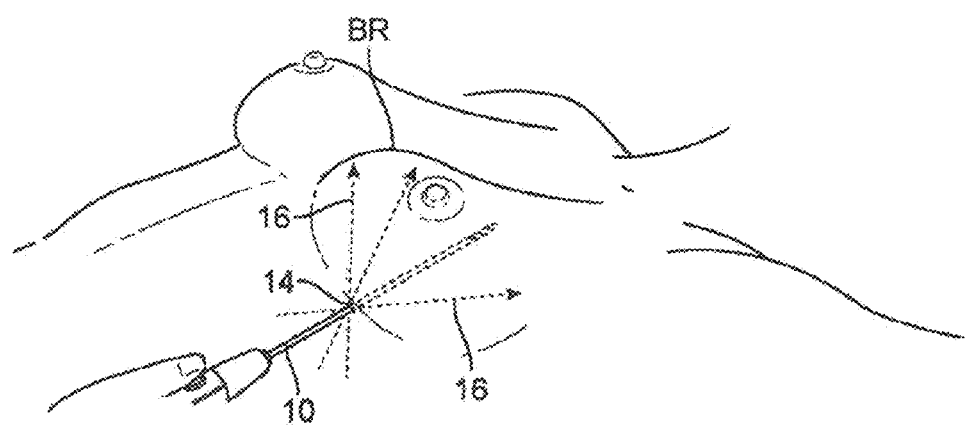

FIGS. 1C and 1D illustrate an example of how the cannula 10 may be inserted into a single entry point 14 beneath the breast BR and how the fat 12 may be deposited along a tract defined by the cannula 10. With the cannula 10 positioned through the entry point 14 within the breast BR, the cannula 10 may be repeatedly advanced and withdrawn along multiple tracts 16 through the common entry point 14 while depositing fat to remodel the breast BR accordingly.

Figure 1E:
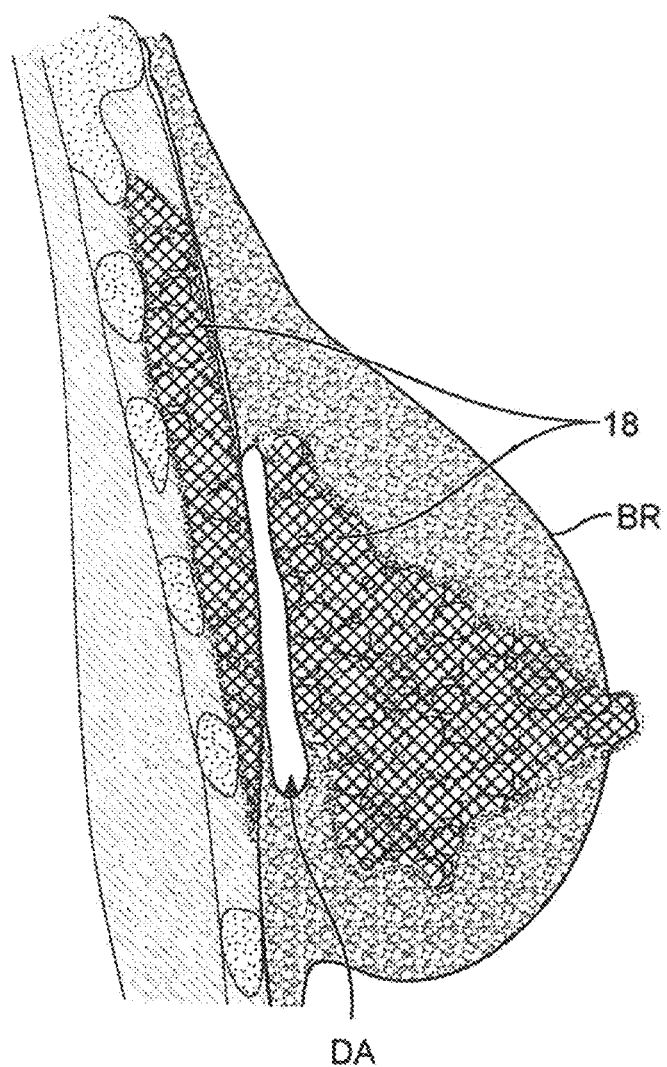
FIG. 1E shows a cross-sectional side view of a breast with areas of breast tissue which are typically to be avoided when depositing adipose tissue.

However, the physician may encounter difficulties discerning when and where the fat can be deposited within the breast BR. FIG. 1E shows a cross-sectional side view of breast BR illustrating areas of breast tissue to be avoided 18, such as within the underlying muscles or ducts, and the targeted deposit area DA which is typically within the subcutaneous fat layer within the breast BR located between the pectoral muscles and the ducts.

Figure 1F:
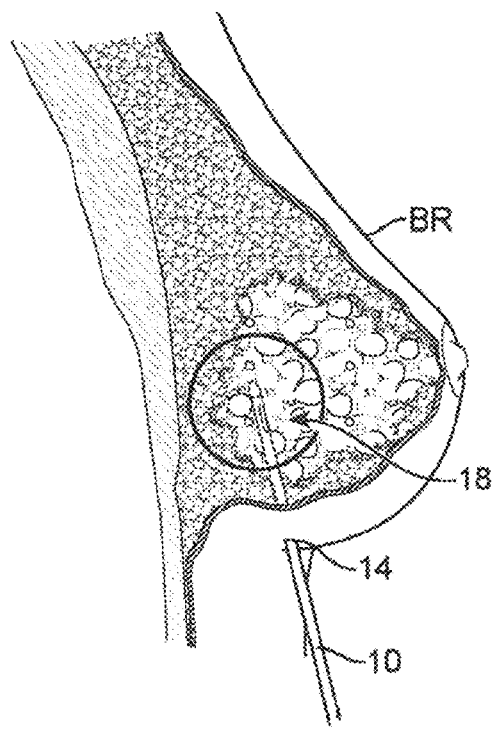
FIGS. 1F to 1H illustrate cross-sectional areas of a breast where an injection cannula has been advanced at varying angles and at different locations for potential fat deposition.
Figure 1G:
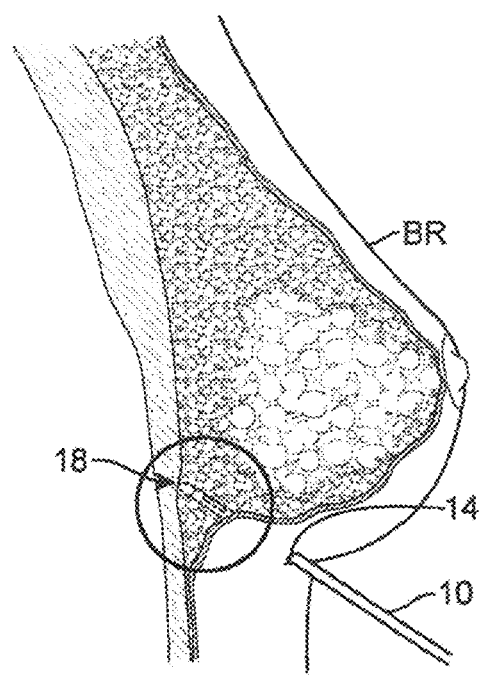
Figure 1H:
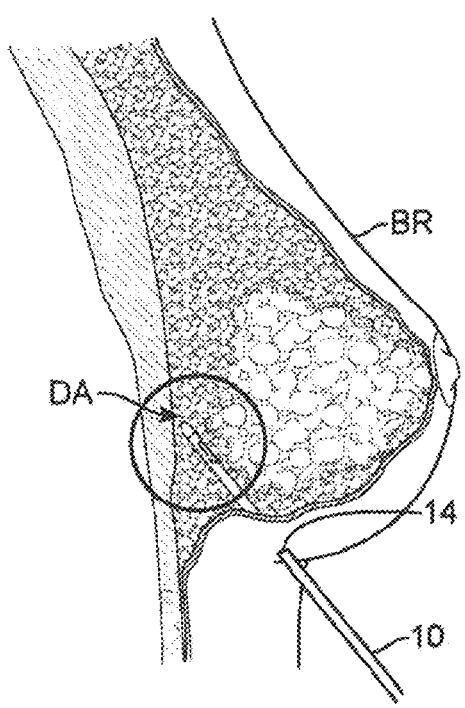

FIGS. 1F to 1H illustrate cross-sectional areas of a breast BR when the cannula 10 has been advanced at varying angles and at different locations where fat may or may not be deposited. For instance, FIGS. 1F and 1G illustrate how the cannula has been advanced into tissue regions to be avoided 18, the cannula 10 may detect the tissue type (as discussed further herein) and give an indication as to the desirability of the location for fat deposition. FIG. 1H illustrates an example of when the cannula 10 may be advanced into a desirable area within the breast BR for fat deposition.

Figure 2A:
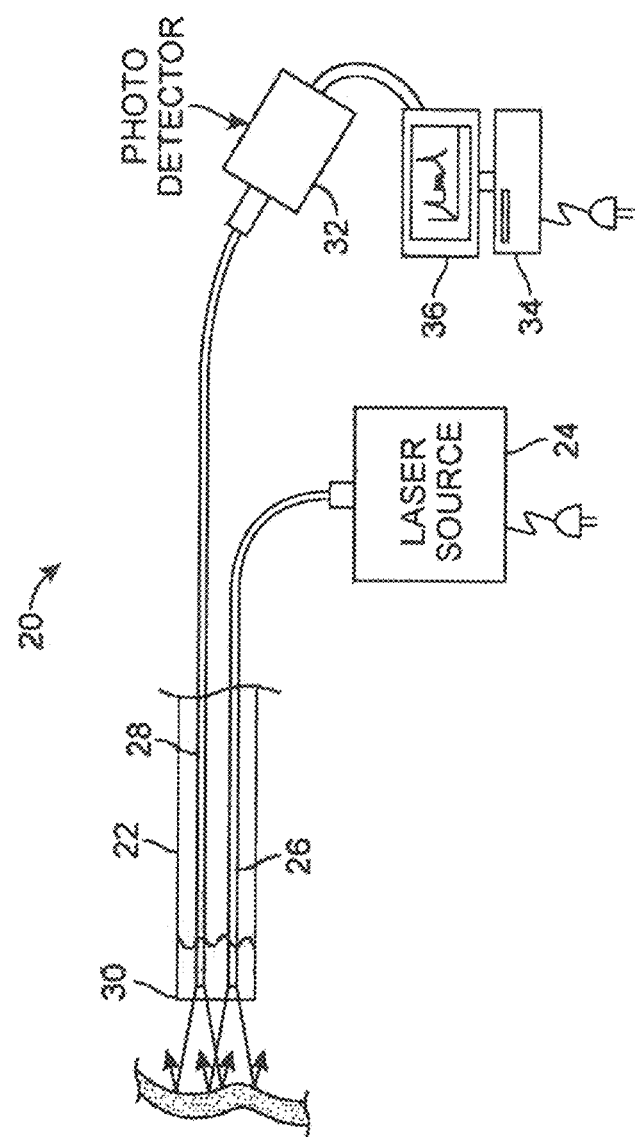
FIG. 2A shows a representative assembly in one variation of an implantation instrument which may be guided within the body by diffuse reflectance.

Thus, in properly positioning the cannula within the breast for injection of the fat, one example of an instrument assembly 20 utilizing diffuse reflectance is shown in the cross-sectional assembly view of FIG. 2A. As illustrated, assembly 20 may generally comprise a cannula 22 which may be optically coupled to a light source 24, e.g., laser, etc. via an optical transmission fiber 26 which is positioned through or adjacent to cannula 22. A distal end of the transmission fiber 26 may emit a light from the distal end 30 of the cannula such that any light reflected by tissue in proximity to the distal end 30 may be detected by the distal end of an optical receiving fiber 28. The receiving fiber 28 may be optically coupled to a photo detector 32 which may in turn by electrically coupled to a processor 34 and a display 36 for use by the physician.

By transmitting a light (such as laser light having a wavelength of between 600 to 1550 μm) via transmission fiber 26 onto the tissue, the backscattered reflected light may be detected by photo detector 32 at a detection range matching that of the transmitted laser output, e.g., ranging up to 50 mW or more. Other suitable wavelengths for the laser light may range, e.g., between 630 to 1450 nm, as many biological tissues have a low absorption window which is away from hemoglobin absorption. Also, such a range may avoid water absorption in the NIR range. Moreover, Rayleigh scattering and Mie scattering may allow for a diffuse reflectance of deep penetrating and back-scattered photons. Another suitable range may include, e.g., 920±10 nm or 1210±10 nm. Laser light wavelengths in such a range may help to differentiate against non-lipid containing tissues when combined with other wavelengths.

Various types of lasers may be used (e.g., superluminescent emitting diode (SLED) lasers, etc.) at multiple wavelengths to highlight the differences in tissue structures. The photo detector 32 may convert the input signal to an output voltage which is then transmitted to processor 34 which may be programmed to differentiate the physiologic structures based on the light scattering properties and light reflectance intensity at various wavelengths. The diffuse reflectance may be optionally utilized in combination with other detection modalities such as ultrasound, optical coherence reflectometry, etc.

Figure 2B:
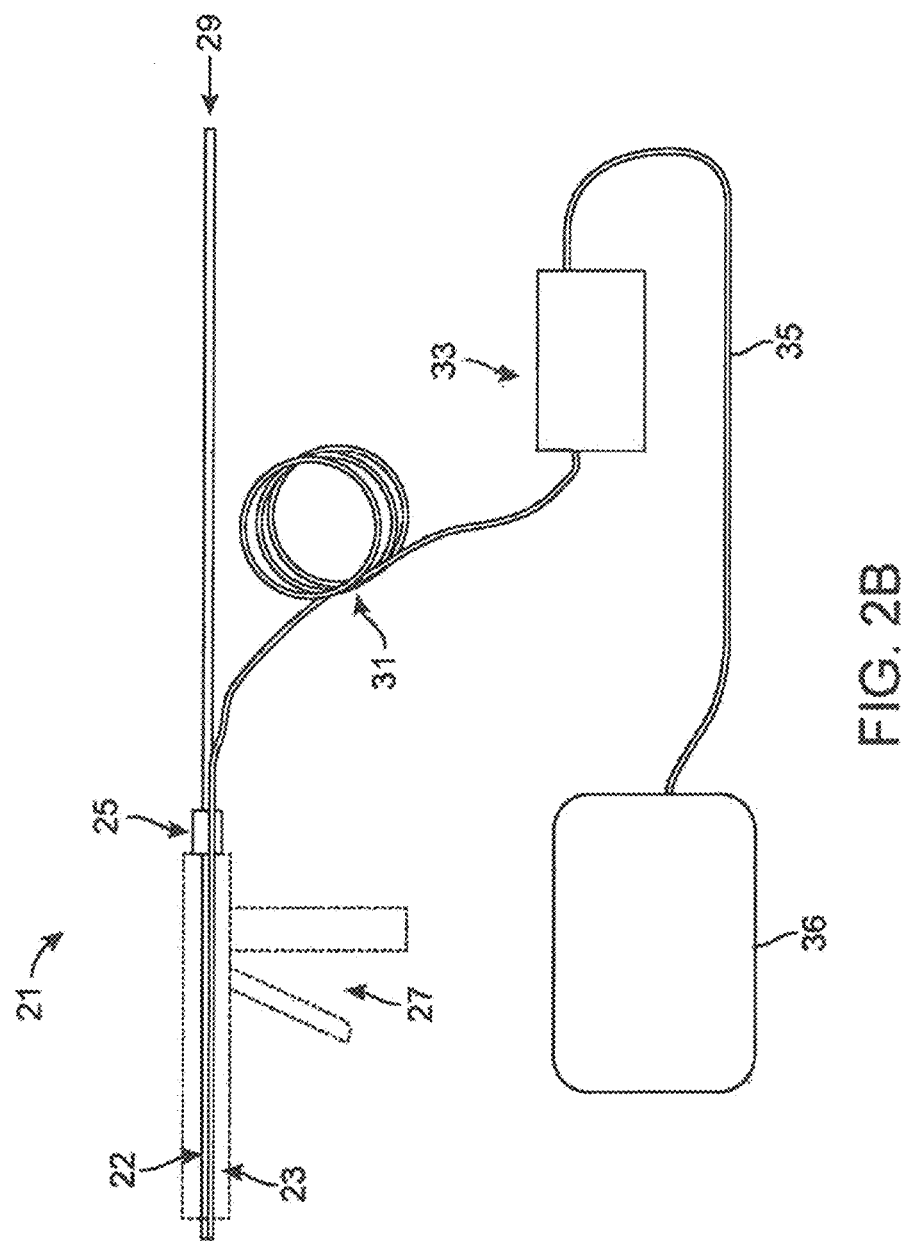
FIG. 2B shows another variation of a guidance assembly having an optical fiber probe.

FIG. 2B shows another variation of a guidance assembly 21 which may have a cannula 22 (for tissue harvesting or injection) through which the injection lumen 29, in this example, may be defined and an optical fiber probe 23, as described above. The assembly 21 may also include a flow sensor 25 as well as an actuator assembly 27 integrated into the assembly 21. An optical cable 31 may couple the optical fiber probe 23 to an optoelectronic (OE) module 33 containing the excitation source, e.g., laser source, as well as the detection electronics. A cable 35 may couple the OE module 33 with a display 36.

Figure 2C:
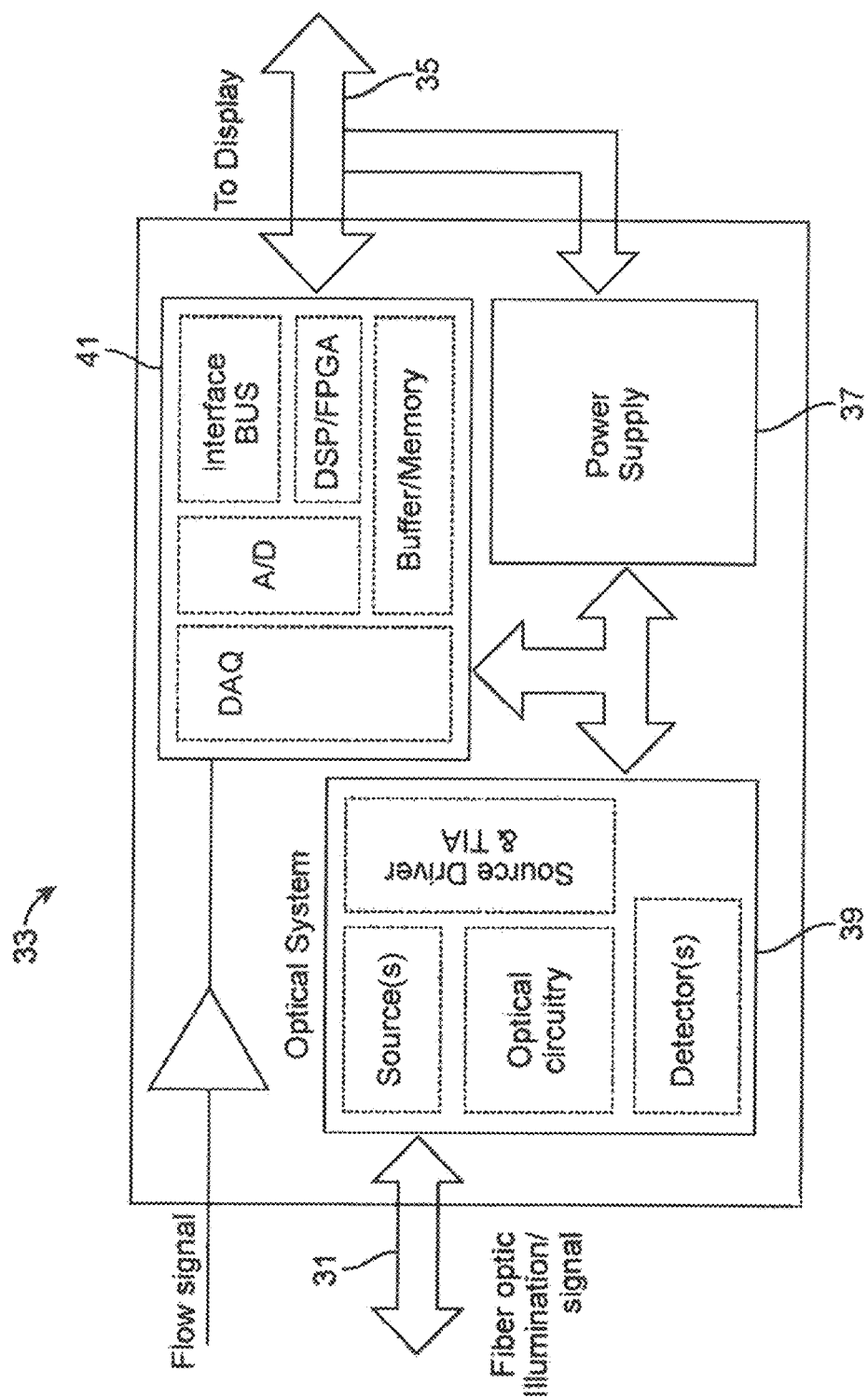
FIG. 2C shows an example of an optoelectronic module which may be integrated with the guidance assembly.

An example of an OE module 33 is shown schematically in FIG. 2C which illustrates the optical cable 31 connected to an optical system assembly 39 comprising the excitation source, optical circuitry, detector(s), source driver, etc. An electronics assembly 41 (e.g., interface bus, digital signal processor, buffer/memory, A/D converter, DAQ (digital acquisition) module, etc.) may communicate with the optical system assembly 39 and a power supply 37 may also be included. The cable 35 may be electrically coupled to the electronics assembly 41 leading to the display or another module. Additionally, the flow sensor 25 may also be seen in electrical communication with the electronics assembly 41 as well.

FIG. 2D illustrates a perspective view of an example of a cannula where the transmission fiber 26 may emit the light 27 onto the adjacent tissue region. The optical receiving fiber 28 is also shown within the cannula distal end 30 receiving the reflected light 29 with information indicative of the tissue type.

Figure 2E:
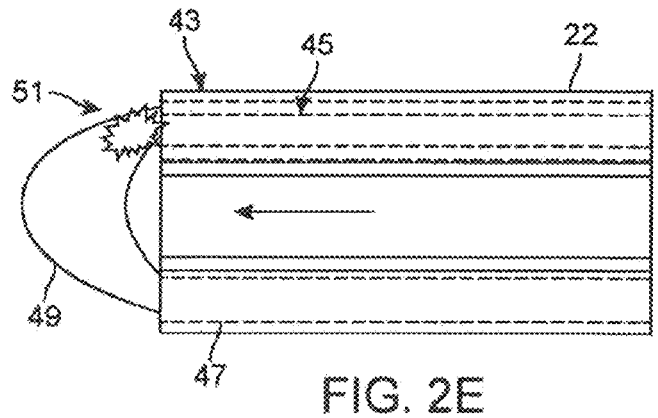
FIG. 2E shows a cross-sectional side view of another example of the cannula having the injection lumen passing through with one or more optical fibers positioned through the cannula.
Figure 2F:
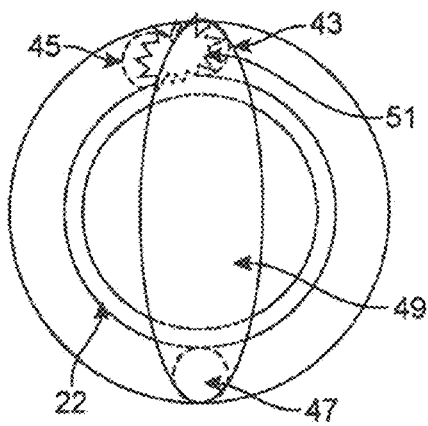
FIGS. 2F to 2I show end views of exemplary embodiments for positioning of the optical fibers for excitation as well as detection.

FIG. 2E shows a cross-sectional side view of another example of the cannula 22 having the injection lumen passing through with one or more optical fibers positioned through the cannula 22. FIGS. 2F to 2I show end views of exemplary embodiments for positioning of the optical fibers for excitation as well as detection. FIG. 2F shows one example where the excitation source fiber 43 may be positioned adjacent to the fluorescence emission sense fiber 45. A diffuse reflectance sense fiber 47 may be positioned in proximity to the excitation source fiber 43 for detecting the reflected diffused light 49 as well as any fluorescence 51 which may be excited from the illuminated tissue.

Figure 2G:
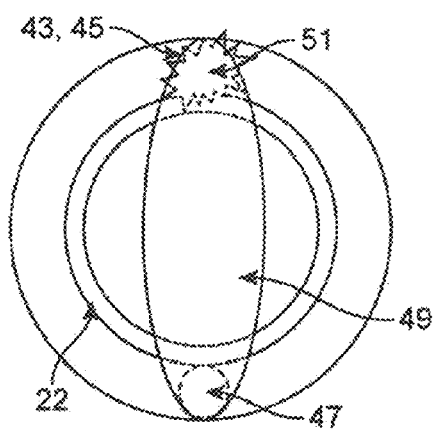
Figure 2H:
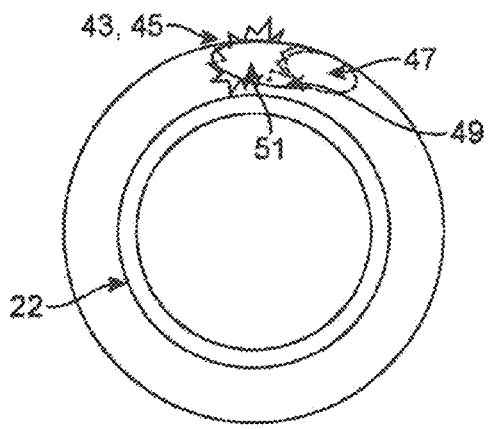
Figure 2I:
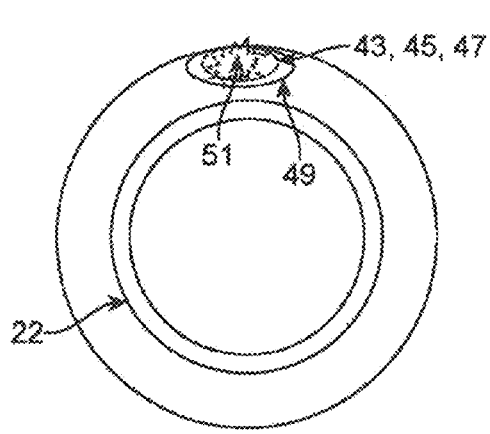

FIG. 2G shows another variation where the excitation source fiber 43 and fluorescence emission sense fiber 45 may be combined into a single optical fiber or fiber bundle. FIG. 2H shows yet another variation where the excitation source fiber 43 and fluorescence emission sense fiber 45 may be combined again but the reflectance sense fiber 47 may be positioned adjacent to the combined fiber or fiber bundle. FIG. 2I shows a similar variation where the excitation source fiber 43, fluorescence emission sense fiber 45, and reflectance sense fiber 47 may all be combined into a single fiber or fiber bundle.

Figure 2J:
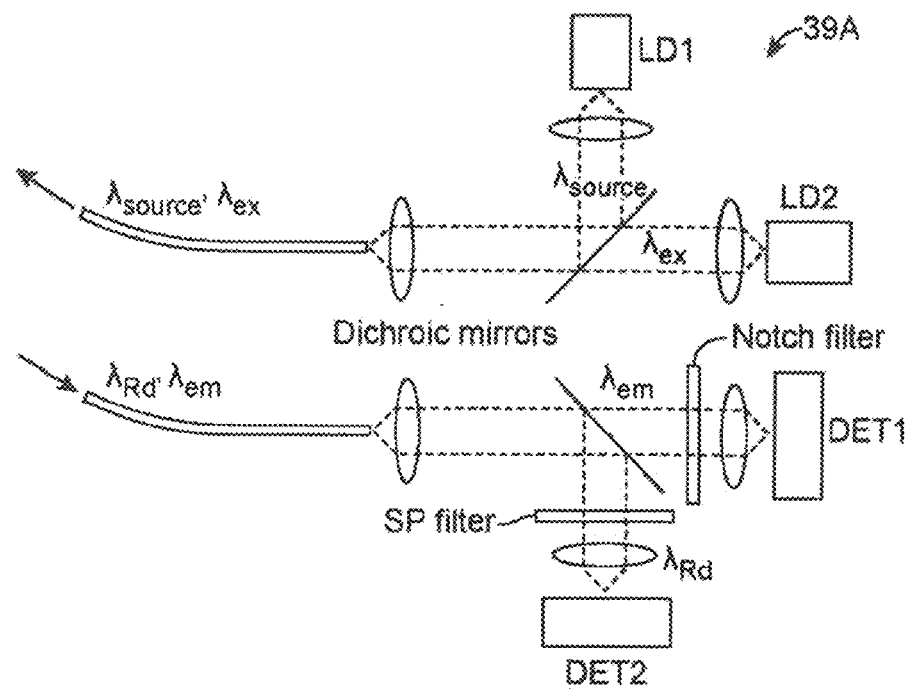
FIGS. 2J to 2N show various configurations for the excitation source and detection assembly which may be used with the guidance assembly.

Turning now to the optical system assembly 39, the excitation source and detection assembly may be positioned into various configurations. FIG. 2J shows one variation in optical system assembly 39A where the excitation source may be combined into a single signal including $\lambda_{source}$ (e.g., from a first laser source LD1) and $\lambda_{ex}$ (e.g., from a second laser source LD2). The diffuse reflectance $\lambda_{Rd}$ as well as the fluorescence emission $\lambda_{em}$ may be received back into the optical system assembly 39 where the signal may be split, e.g., via dichroic mirrors, for detection of the fluorescence emission $\lambda_{em}$ by a first detector DET1 and of the diffuse reflectance $\lambda_{Rd}$ by a second detector DET2 for processing by the electronics assembly 41.

Figure 2K:
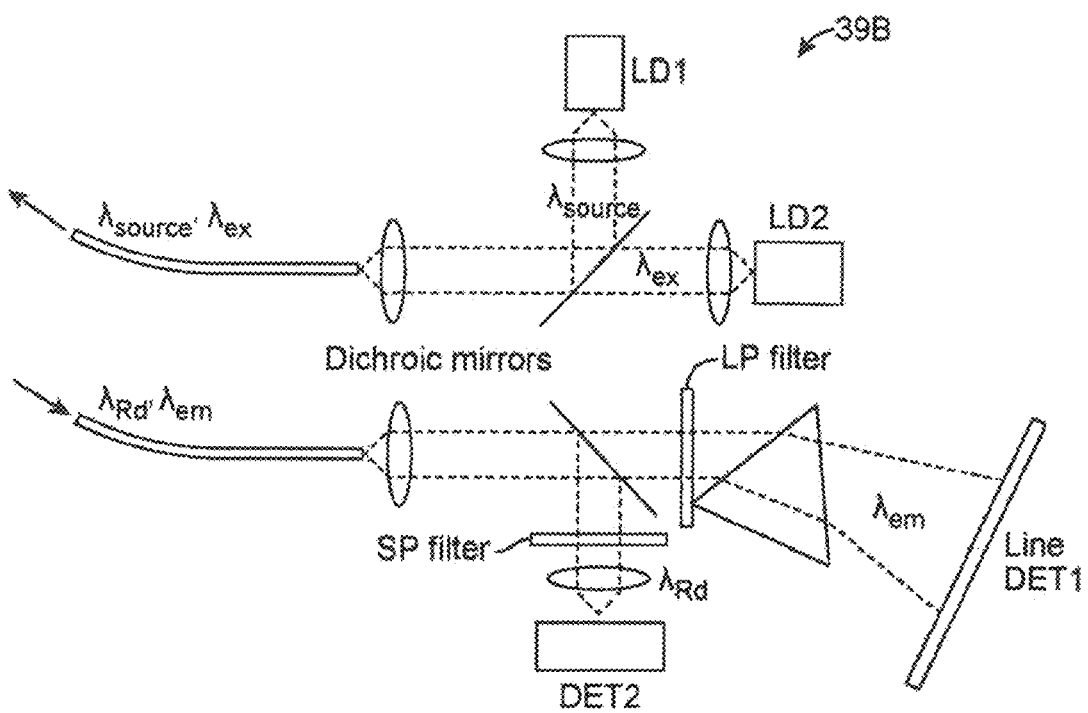
Figure 2L:
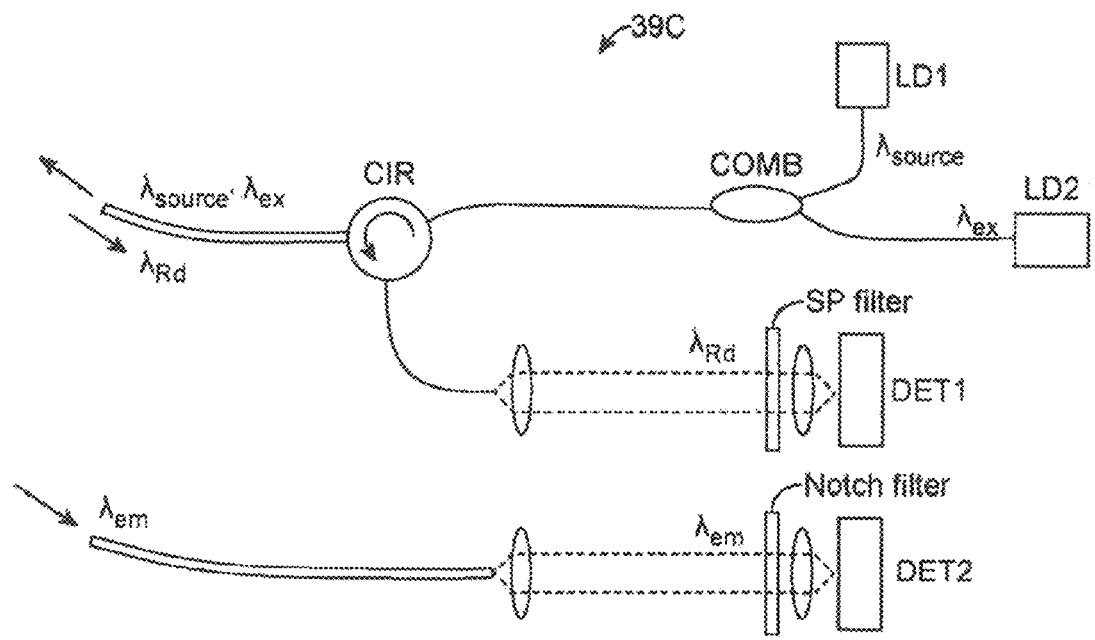
Figure 2M:
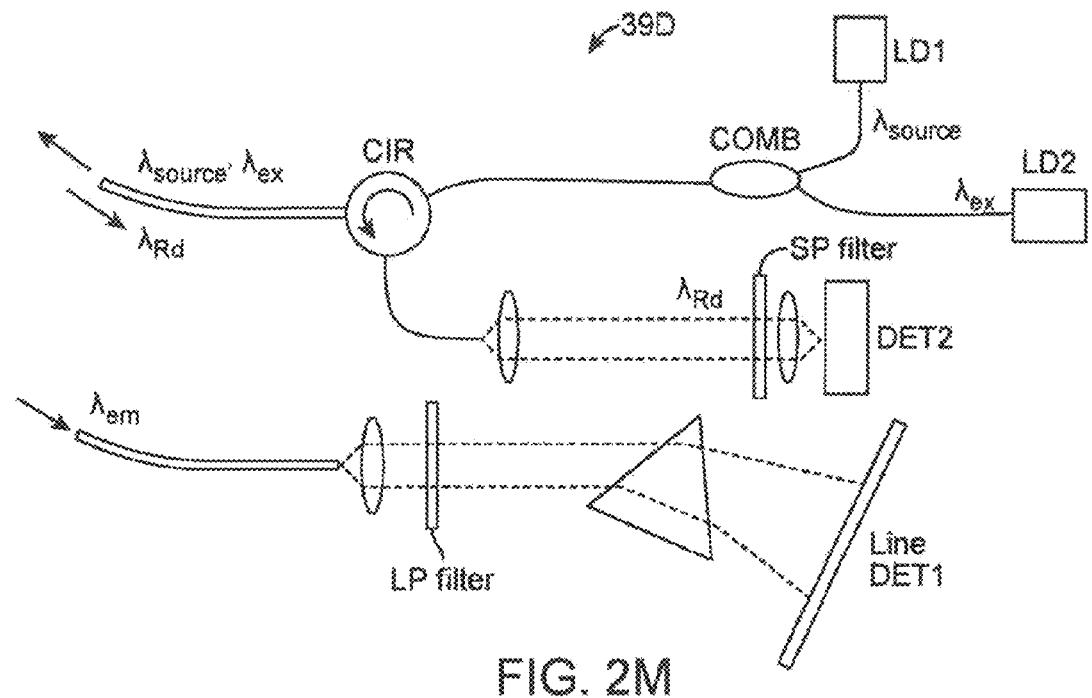
Figure 2N:
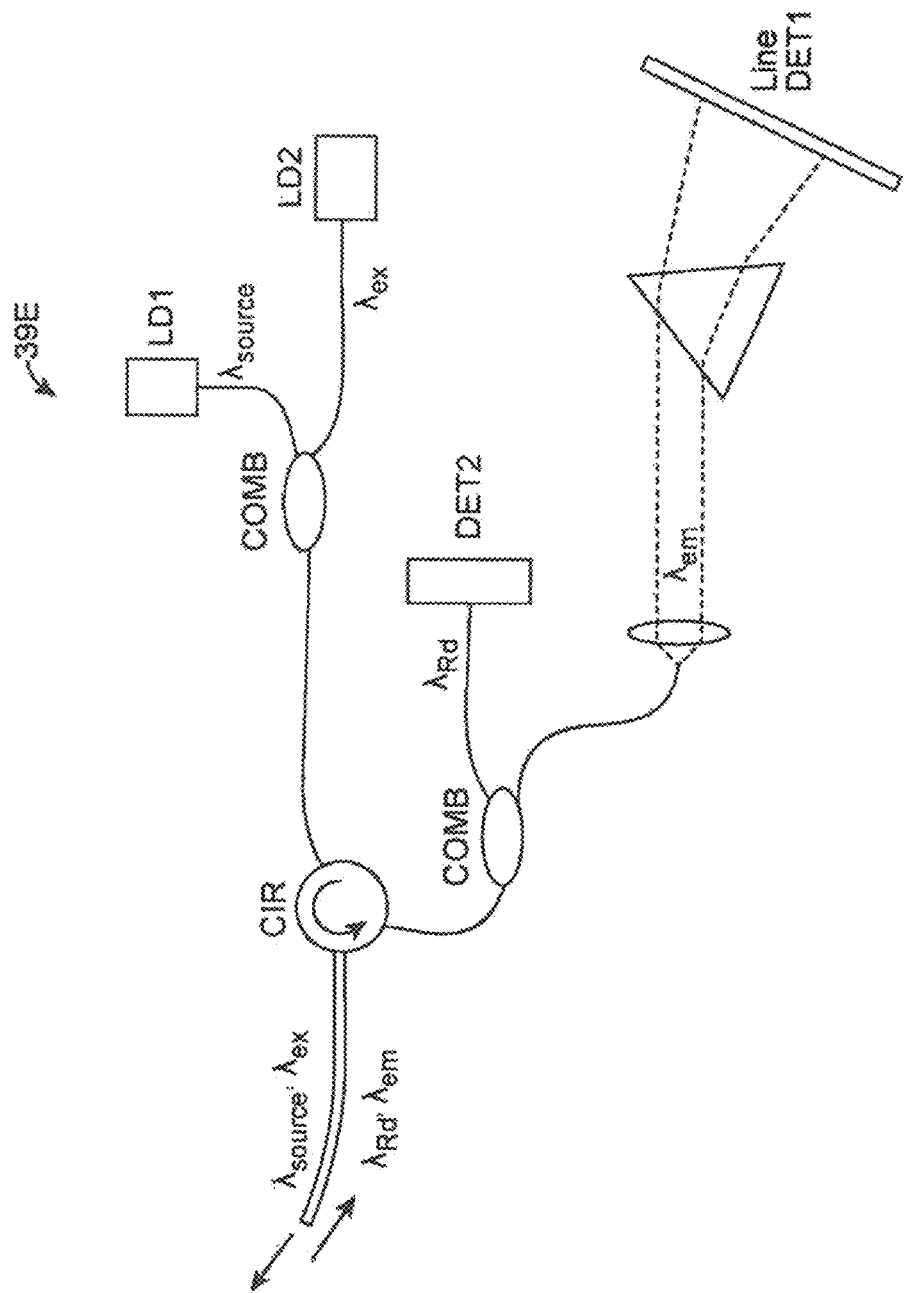

FIG. 2K shows another variation where the fluorescence emission $\lambda_{em}$ may be filtered and detected, e.g., by a line detector DET1. FIG. 2L shows another variation where the excitation source $\lambda_{source}$, $\lambda_{ex}$ may be combined into a single signal and where the same fiber or fiber bundle may be used to detect the diffuse reflectance $\lambda_{Rd}$ which may be filtered for detection by DET1 while the fluorescence emission $\lambda_{em}$ may be detected in a separate fiber or fiber bundle by second detector DET2. FIG. 2M shows yet another variation where the excitation source $\lambda_{source}$, $\lambda_{ex}$ and diffuse reflectance $\lambda_{Rd}$ may be detected via a single fiber or fiber bundle, as above, but where the fluorescence emission $\lambda_{em}$ may be detected in a manner similar to the configuration shown in FIG. 2K above. FIG. 2N shows yet another variation where the excitation source source $\lambda_{source}$, $\lambda_{ex}$ and detected diffuse reflectance $\lambda_{Rd}$ and fluorescence emission $\lambda_{em}$ may be combined into a single fiber or fiber bundle. The detected signal may be filtered for detection by DET1 and DET2 as shown.

The tissue guidance assemblies described may be integrated into any of the harvesting and/or injection cannulas described herein to help distinguish between different tissue types when harvesting tissue and/or injecting processed tissue into the body.

By having the processor 34 differentiate between the different light scattering properties of the tissue, the physician can determine whether the cannula 20 is located within or away from a particular anatomical structure for injecting or refraining from injecting the adipose tissue. An example is illustrated in the graphical interface of FIG. 3A which shows the reflectance intensity 40 of the tissue encountered by the cannula 22. Such a graph 40 may be displayed to the physician to provide a real time indication of cannula position during a procedure. In this example, as the cannula 22 approaches the skin surface, an initial noise floor 42 indicative of the presence of the cannula in air may be initially shown, as illustrated in FIG. 3B.

As the cannula 22 approaches and is inserted into the skin 1, the signal intensity may rise indicating to the physician that the cannula 22 has entered the skin 1. As the cannula 22 is advanced into the breast BR, the different layers of tissue may be detected and charted. For instance, as the cannula 22 enters adipose tissue or fat 2 within the breast, the signal intensity may drop to a level between the initial signal 42 and the signal sensed from the skin 1. This detected level may indicate to the physician that they are within a region of the breast BR where fat may be injected. Other tissue structures such as ligament 3 or muscle 4 may be reflected and charted accordingly where each different tissue type may generate its own level of signal intensity. In the event the cannula 22 detects tissue types other than fat 2, the processor 34 may be programmed to signal some visual or auditory alarm indicating that the cannula 22 may need repositioning. In the event that the signal drops to the noise floor 44, this may indicate that the cannula 22 has advanced between or has been withdrawn from the breast BR.

With the detection of tissue types utilizing diffuse reflectance, the assembly may be programmed by processor 34 to automatically inject and/or cease injection of the fat from the cannula 22 into the breast depending upon the type of tissue detected. By utilizing a closed-loop system, as the cannula 22 is advanced or withdrawn from the breast, the different tissue types may be automatically detected by processor 34. When the present of fat is detected, cannula 22 may automatically inject the fat from cannula 22 in a controlled volume and injection rate. In the event that the system detects a position of the cannula 22 in tissue types other than fat, such as muscle, the processor 34 may automatically cease the injection into the breast until the presence of fat is again detected within the breast in which case the processor 34 may automatically resume the injection of the fat. Alternatively, rather than utilizing an automated system, an alarm or indication may be indicated to the physician who may manually inject and/or cease the injection of the fat from the cannula into the breast.

Moreover, with a cannula having a size ranging anywhere from 16-10 gauge (or higher), a typical volume of fat ranging from, e.g., 10-20 cc, may be accomplished. With such a volume injectable per cannula, the amount of fat injected during an entire procedure within, e.g., a breast, may vary from, e.g., 100-1000 cc per breast, or an average of, e.g., 450 cc per breast.

While the cannula 22 may be traversed through the body at various rates, e.g., up to 10 cm/sec, the withdrawal rates for the cannula 22 may vary as well. For example, the cannula may be retracted at rates of, e.g., 2 mm/sec up to 5 cm/sec, and the cannulas may optionally incorporate a hydrophilic coating along its length to facilitate the advancement or withdrawal through the tissue. Moreover, the cannulas may optionally oscillate (automatically or manually) to facilitate injection of the fat.

The identification of tissue type may be used not only for fat injection into the body, but it may also be used in identifying desirable tissue regions for the harvesting of the fat from the body for processing prior to re-injection.

Figure 4A:
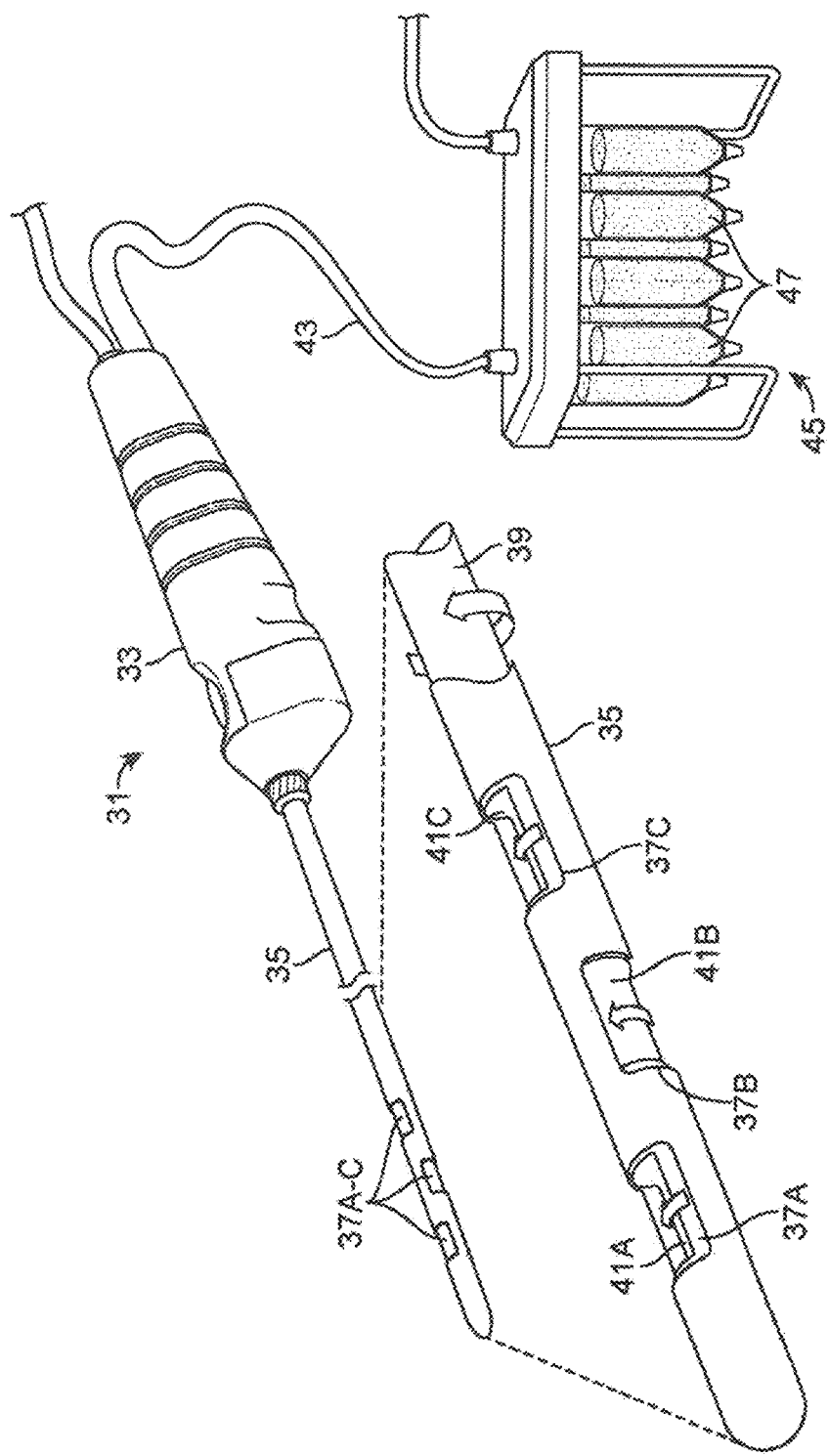
FIG. 4A shows a perspective assembly view of a cannula assembly which may be used for harvesting and collecting fat from within a body.

One variation is illustrated in the perspective assembly view of FIG. 4A showing cannula assembly 31 which illustrates a handle 33 for providing the harvesting of the fat from the body as well as the injection into the body. An optionally detachable harvesting cannula 35 is shown extending from the handle 33 and defining one or more openings or fenestrations 37A to 37C along the cannula 35 near the distal end. Each of the openings 37A to 37C may be staggered or uniform relative to one another. Moreover, although three openings are shown, this is merely exemplary and a fewer or greater number of openings may be defined along the cannula 35. A rotatable inner shaft 39 may be positioned within the cannula with a number of cutting windows 41A to 41C which correspond in position and size with respect to the openings 37A to 37C along the cannula 35.

In use, the inner shaft 39 may be rotated relative to a stationary cannula 35 such that the when the openings are aligned, adjacent fat may be introduced within the openings and then cut or shaved into the cannula 35 as the inner shaft 39 rotates and closes the openings onto the fat with respect to the cannula 35. The cut or shaved fat may be drawn through the cannula 35 and handle 33 and through a tubing 43 which is in fluid communication with a harvesting reservoir assembly 45 which may contain one or more individual reservoirs or cartridges 47. The individual cartridges 47 containing the collected fat and other tissue may be further processed and directly introduced into the patient's body, such as the breasts, for remodeling the body.

Figure 4B:
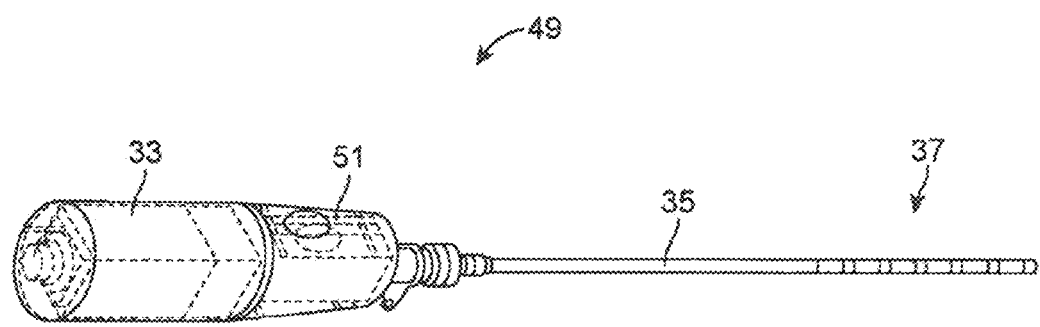
FIGS. 4B and 4C show perspective and cross-sectional side views of another variation of a cannula assembly used for harvesting and/or injection.
Figure 4C:
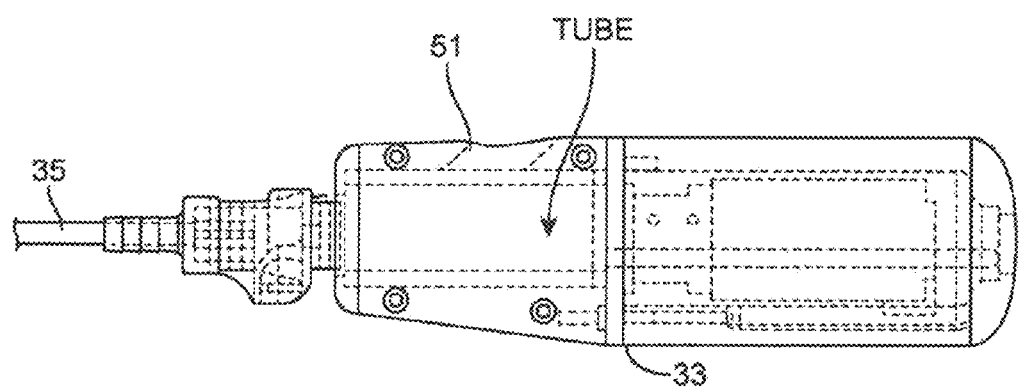

FIGS. 4B and 4C show perspective and partial cross-sectional side views of another variation of a cannula assembly 49 which may be used for harvesting and/or injection. The assembly 49 illustrates a harvesting cannula 35 with one or more openings 37 defined near the distal end of the cannula 35. The handle 33 in this variation further illustrates an opening 51 along the side of the handle 33 into which a reservoir or cartridge 47 or tubing may be fluidly coupled to transfer and/or collect the aspirated fat for further processing or re-injection.

FIG. 4D illustrate side views of various harvesting cannulas 35 which have a variable number of openings 53 for collecting the fat. As shown, the number of openings 53 may be varied from a few, e.g., three openings, to several openings 55, e.g., six openings.

Figure 4E:
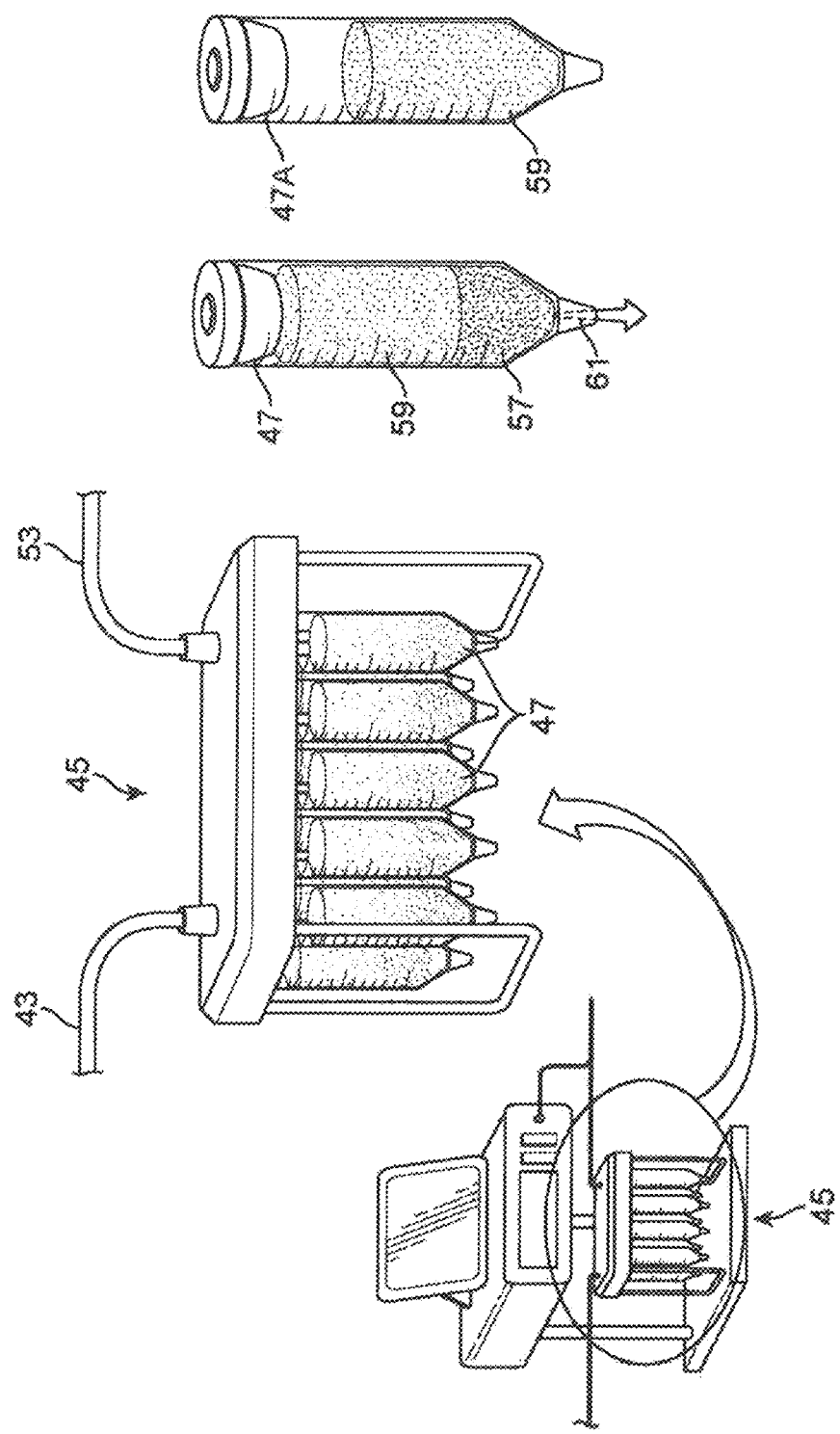
FIG. 4E shows an assembly view of a harvesting reservoir assembly having one or more individual reservoirs or cartridges.

An example of the harvesting reservoir assembly 45 is illustrated in the perspective view of FIG. 4E which shows assembly 45 fluidly coupled to a harvesting cannula. As described above, the reservoir assembly 45 may contain one or more individual reservoirs or cartridges 47 each fluidly coupled. The tubing 43 coupled to the harvesting cannula may draw in the collected fat 59 and other fluids or tissue 57 directly into the one or more cartridges 47 thus increasing the viability of the collected fat by reducing exposure to air and mechanical trauma as well as reducing the amount of time spent outside the patient's body.

The one or more cartridges 47 may be individually or collectively processed and the miscellaneous fluids or tissue 57 may be removed from the cartridge 47, e.g., via an opening 61 located along the cartridge 47. The resulting processed cartridge 47A may retain only the desired fat tissue 59 for direct injection into the patient body by utilizing the cartridge 47A directly with the injection assembly.

Figure 4F:
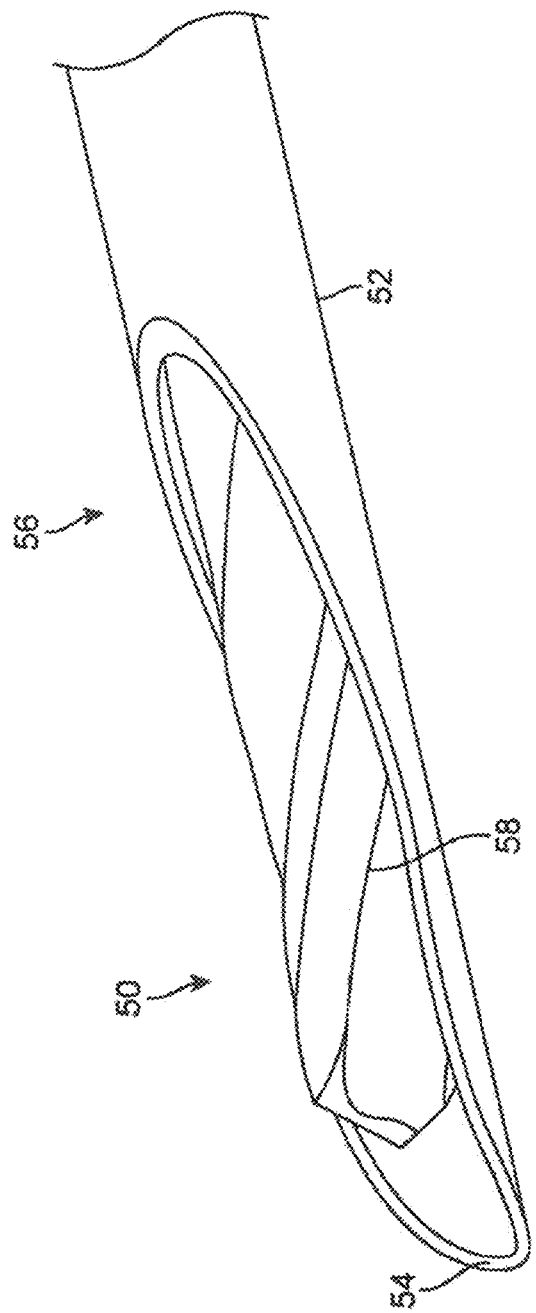
FIG. 4F shows a perspective view of one variation of an instrument having an internal screw-type mechanism for controlling the delivery of the tissue into the body.

In addition to the detection of tissue types for facilitating the accurate harvesting or injection of the fat, various instruments may be utilized within or in conjunction with the cannula for delivering precise volumes of the fat in a controlled manner. One example is shown in the perspective view of FIG. 4F which illustrates a screw-type injection mechanism 50, such as a screw mechanism 58 having a fluted shaft. The screw mechanism 58 may be rotatably positioned within cannula 52 which may also have a tapered piercing tip 54 and a distal opening 56 for injecting the fat delivered through the cannula 52. As the screw mechanism 58 rotates, any fat contained within a connected reservoir or within the cannula 52 itself may be metered out through the distal opening 56. Starting or stopping the injection of the fat may be accurately controlled by starting or stopping rotation of the mechanism 58.

Figure 5:
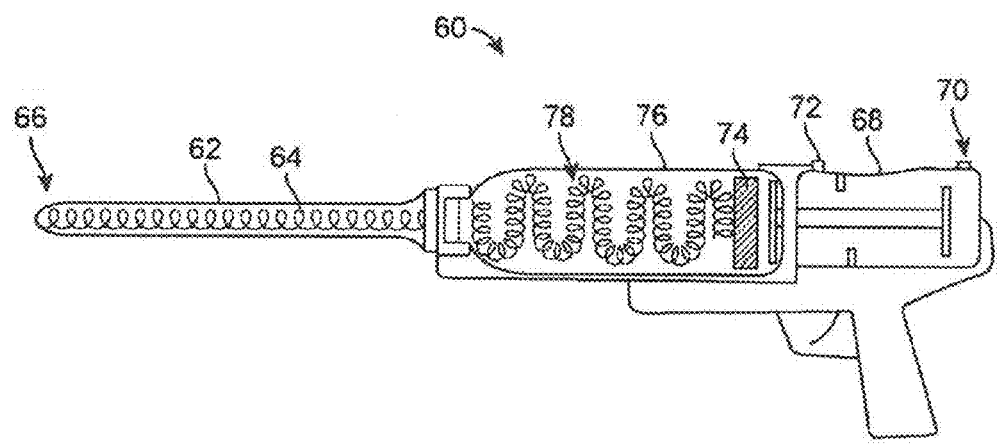
FIG. 5 shows a cross-sectional side view of another variation of an instrument having an internal screw-type mechanism coupled to a pressurizable reservoir.

Another variation is illustrated in the cross-sectional side view of injection instrument 60 shown in FIG. 5. In this variation, an outer sheath or cannula 62, e.g., 20 gauge, which may range from, e.g., 6-12 inches in length, may be operatively connected to a handle 68 and may also be in fluid communication with a reservoir 76 containing a volume of the adipose tissue or fat 78. A fluted mechanism 64 may be rotatably positioned within a lumen defined through the cannula 62 and a piston 74 may also be incorporated into the reservoir 76 for optionally pressurizing the fat 78 for facilitate injection through the cannula 62. An air inlet port 70 and an air outlet port 72 may also be optionally included along handle 68 for controlling the air within the device as piston 74 is actuated.

Figure 6:
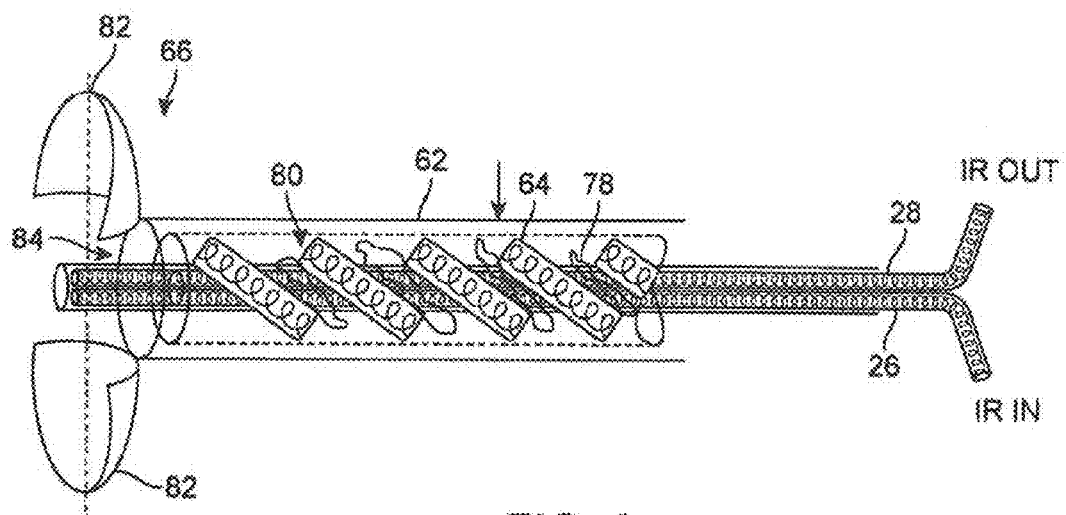
FIG. 6 shows a cross-sectional side view of an instrument shaft having a retractable distal tip.

FIG. 6 shows a detailed cross-sectional side view of the cannula 62 from FIG. 5 with an optional retractable cover 82 located along the distal end 66 of the cannula 62. In use, once the cannula 62 has been advanced and desirably positioned within the breast BR for fat injection using the transmission fiber 26 and receiving fiber 28 described above, the piston 74 may be optionally actuated and the fluted mechanism 64 may be actuated to rotate such that the fat 78 is advanced distally through the lumen 80 of cannula 62. The one or more members of optional cover 82 (if present) may be retracted, as shown, to reveal the distal opening 84 of lumen 80 allowing for the injection of the fat 78 into the breast tissue.

Figure 7A:
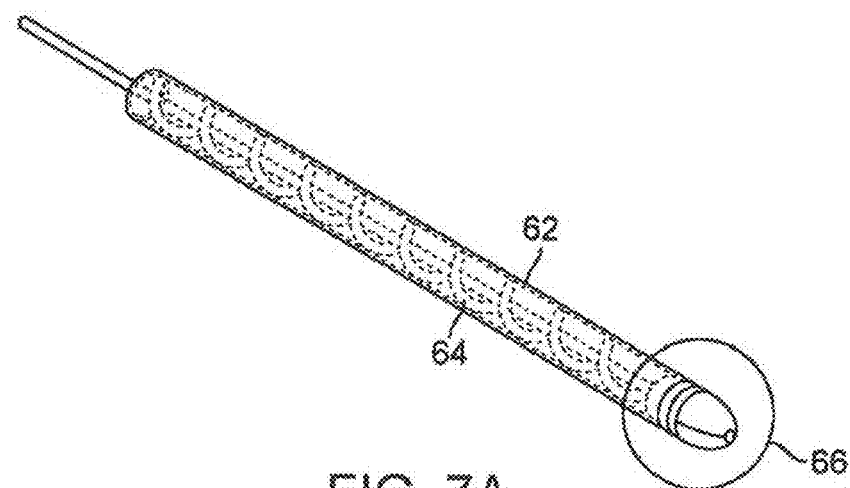
FIGS. 7A to 7C show perspective views of the instrument shaft, handle, and tip, respectively, having a screw-type mechanism.
Figure 7B:
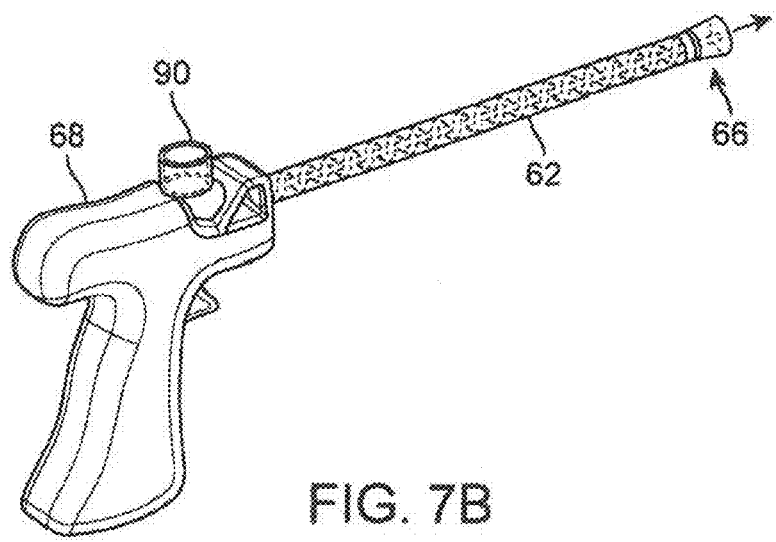
Figure 7C:
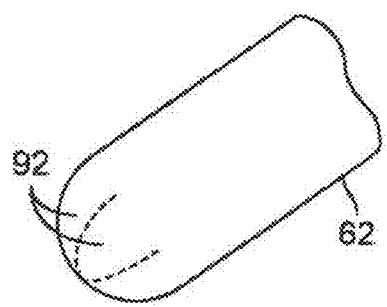

Another example of an injection assembly is shown in the perspective views of FIGS. 7A to 7C. Cannula 62 is shown with fluted mechanism 64 rotatably positioned within. Distal end 66 is shown having optionally retractable members 92 which form an atraumatic rounded tip when closed for advancement through tissue. However, when fat is ejected from cannula 62, the retractable members 92 may open to allow for the injection of the fat. An entry port 90 for introducing adipose tissue into the handle 68 is also shown where the entry port 90 may be located in proximity to a proximal end of the fluted mechanism 64.

Figure 8A:
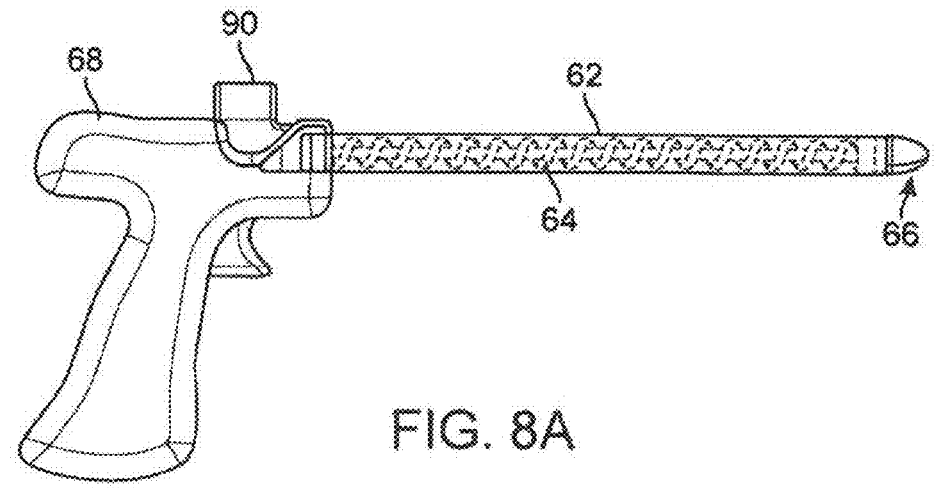
FIGS. 8A to 8C show side views and detailed perspective views of an instrument having a screw-type mechanism.
Figure 8B:
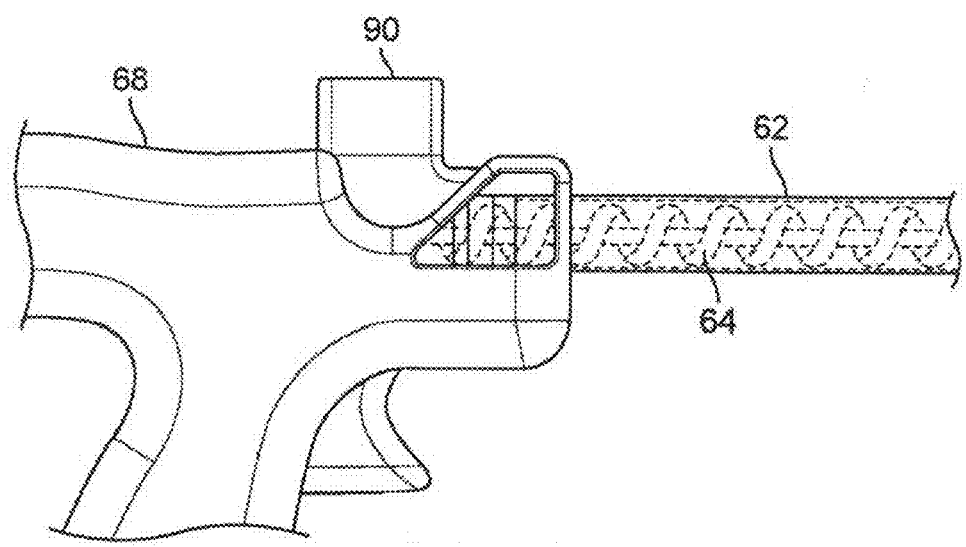
Figure 8C:
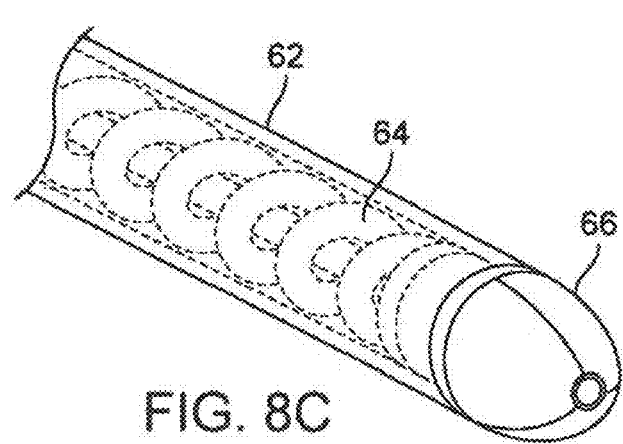

As illustrated in the side and perspective views of FIGS. 8A to 8C, the entry port 90 may be positioned along the handle 68 in proximity to the proximal end of mechanism 64 such that fat for injection introduced into the handle 68 may be taken up by the mechanism 64. The entry port 90 may open into a chamber which is in fluid communication with the cannula 62 and mechanism 64 to minimize any clogging or obstruction which may occur due to the fat.

Figure 9A:
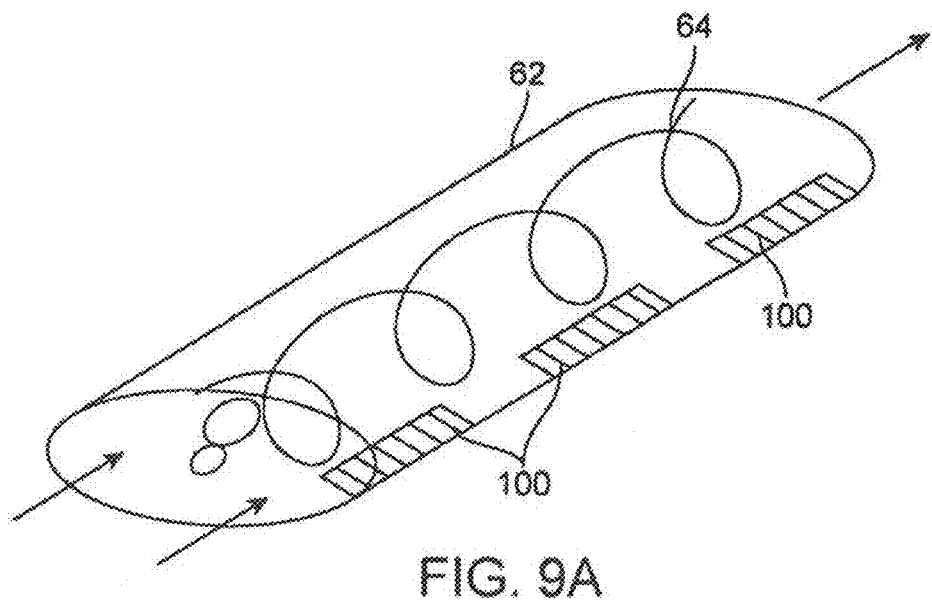
FIGS. 9A to 9C show perspective detailed views of an instrument shaft incorporating projections, such as bristles, within the cannula shaft for functioning as a stop mechanism to the adipose material and to facilitate the linear movement of the material through the shaft lumen.
Figure 9B:
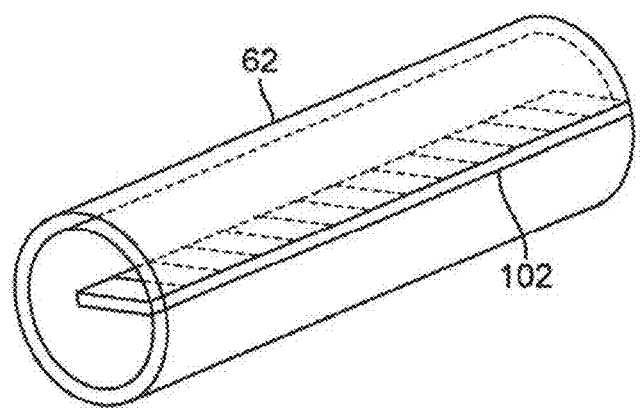
Figure 9C:
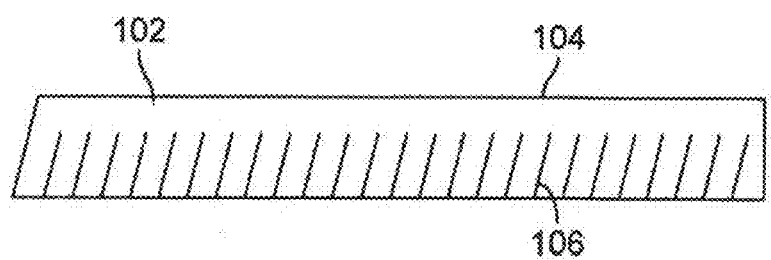

To further minimize or inhibit any clogging of the fat during injection into the patient, FIGS. 9A to 9C show perspective and side views of one or more bristle stop members 100 which may be positioned attached along the lumen of cannula 62. The bristle stop members 100 may generally comprise bristles or projections 106 which are attached along an attachment length 104 along the lumen and extend into the lumen and act as a stop for fat reducing radial travel and may function to increase the translational linear movement of the fat through the cannula 62 without inhibiting the rotational movement of the mechanism 64 adjacent to the bristles 106. The bristles 106 may extend along the lumen in discrete segments, as shown in FIG. 9A, or as a continuous bristle member 102, as shown in FIG. 9B.

Figure 10:
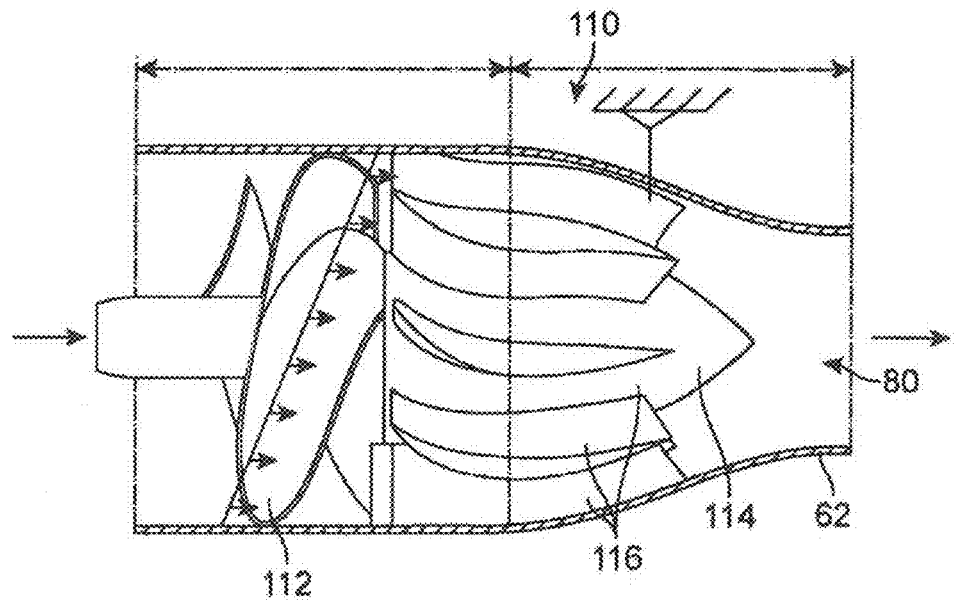
FIG. 10 shows a side view of one variation of an impeller and stator mechanism for facilitating adipose tissue movement within the instrument as well as uniformly dispensing the tissue material from the cannula.

In yet another variation, the injection assembly may optionally incorporate an impeller-stator assembly 110, as shown in the partial cross-sectional side view of FIG. 10, within the housing of the handle to help accelerate the fat to a speed sufficient for injection as well as to uniformly dispense the fat through the cannula 62 for uniform injection into the breast. Generally, an impeller-stator assembly 110 may have an impeller 112 which has one or more blades extending radially from a hub and is rotatable relative to the cannula 62. A stator 114 which remain static relative to the assembly may be located distal to the impeller 112 and may also have one or more stator blades 116 which extend radially from its hub to facilitate the uniform distribution of the fat passing through the assembly 110.

Figure 11:
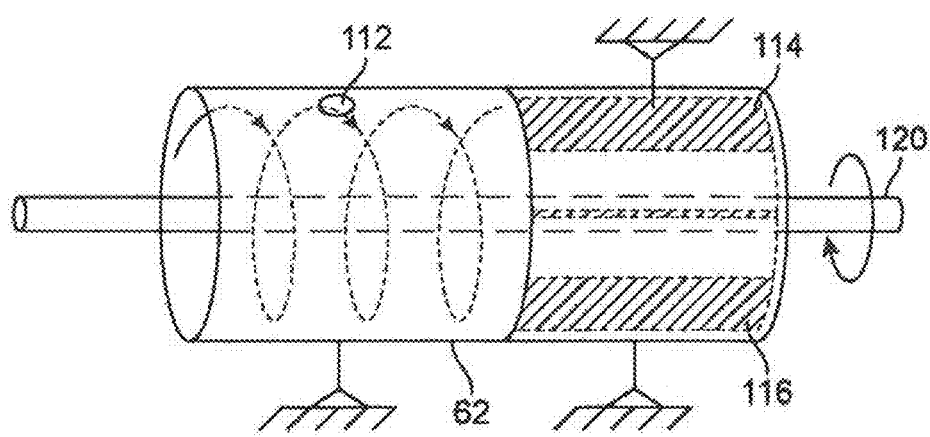
FIG. 11 shows a side view of another variation of an impeller and stator mechanism.

In use, as shown in the example of FIG. 11, as the impeller 112 rotates via a drive shaft 120, the fat contained within the housing or reservoir may be propelled distally through the assembly past the blades 116 of the stator 114 which remains static. As the fat is urged through the assembly, the flow may be uniform as it is urged through the cannula 62 for injection into the breast tissue. FIGS. 12A to 12F show examples of various impeller configurations 132, 134, 136, 138, 140 which may be used in the impeller-stator assembly 110.

Figure 13:
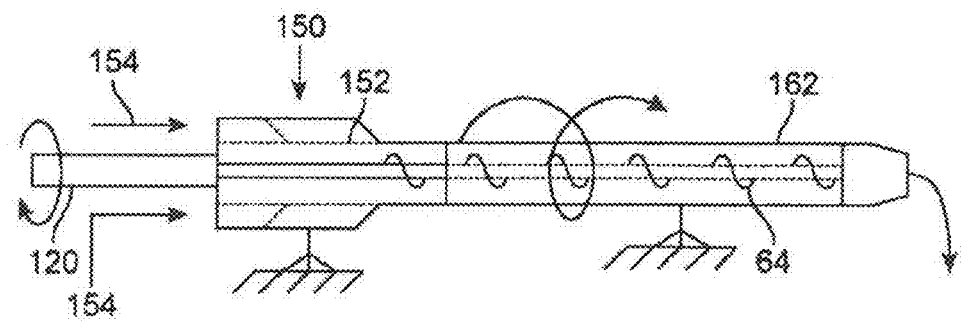
FIG. 13 shows a representative example of another variation of an instrument having an introduction chamber for receiving the adipose tissue for injection.
Figure 14:
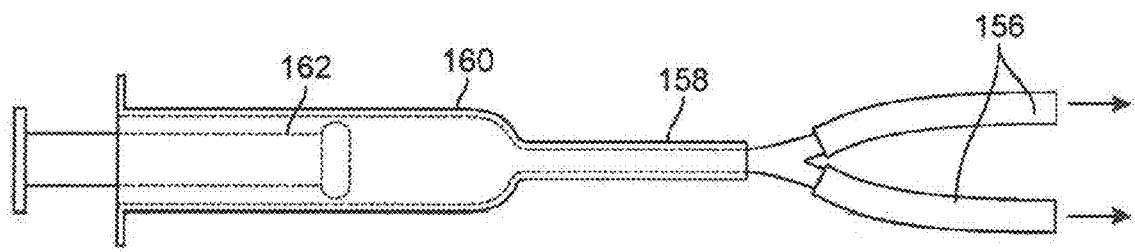
FIG. 14 shows one variation of a reservoir which may be used to introduce the adipose material into an injection instrument.
Figure 15:
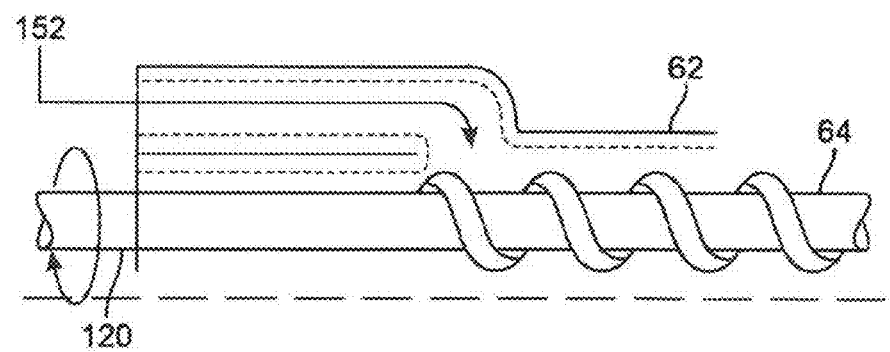
FIG. 15 shows a detailed cross-sectional side view of an inlet port for receiving the adipose material into the cannula for injection.

FIG. 13 shows yet another variation of an injection assembly incorporating a fat introduction chamber 150 within the housing of the handle. The introduction chamber 150 may be positioned proximally of the cannula 62 with an entry port 152 which opens above a proximal end of the fluted mechanism 64 when the assembly is held upright. One or more introduction lumens 154 may open into the introduction chamber 150 for receiving the fat from a reservoir 160, as shown in the side view of FIG. 14. The reservoir 160 may be optionally pressurized via, e.g., a plunger 162, and fluidly coupled to the introduction chamber 150 via tube 158 which may optionally divide into one or more transfer lumens 156. As the mechanism 64 is actuated by drive shaft 120 (which may be automatically controlled by processor 34, as previously described), fat may be urged from the pressurized reservoir 160 to transfer into the introduction chamber 150 and then into contact with the proximal end of mechanism 64 through entry port 152, as shown in the detail cross-sectional side view of FIG. 15, for injection into the subject's breast.

Figure 16A:
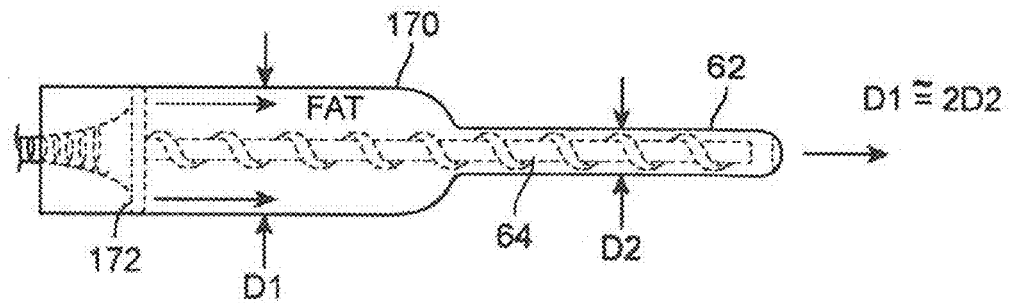
FIG. 16A shows a cross-sectional side view of another variation of an injection instrument having at least two sections with differing diameters as well as a pressurizing mechanism, such as a piston, to inhibit clogging of the adipose material during injection.
Figure 16B:
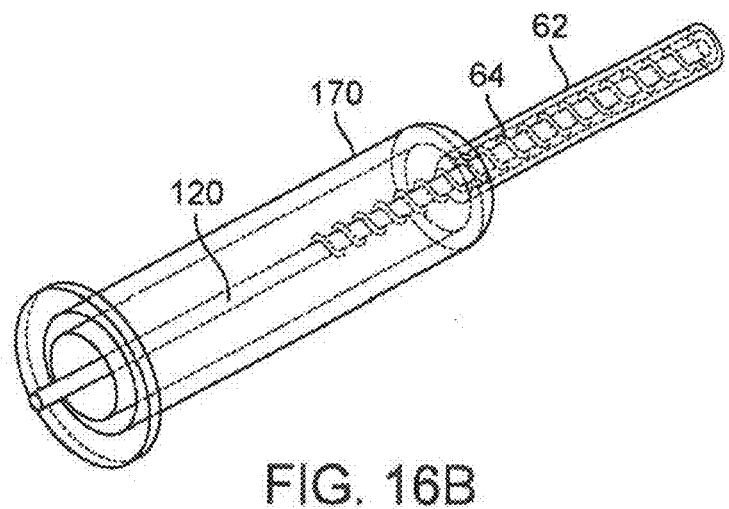
FIG. 16B shows a perspective view of a dual-diameter injection instrument.
Figure 16C:
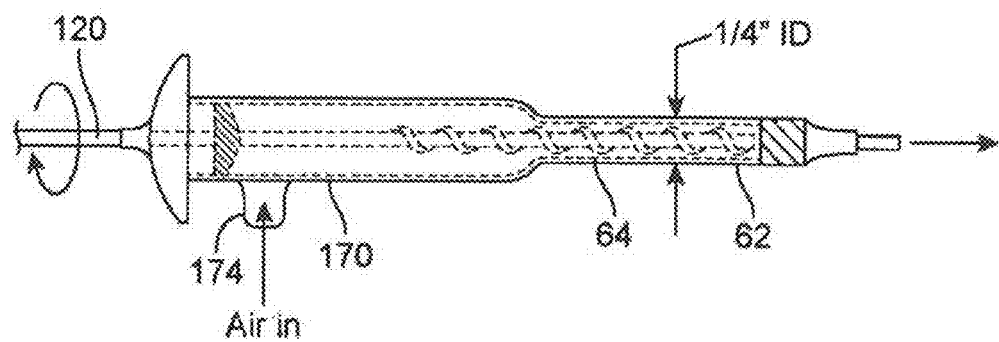
FIG. 16C shows a cross-sectional side view of another variation of a dual diameter injection instrument.

Another variation is shown in the partial cross-sectional side view of FIG. 16A, which shows a fat introduction chamber 170 having a first diameter D1 from which cannula 62 extends having a second diameter D2 where the diameter of D1 is about twice the diameter of D2. In this variation, chamber 170 may optionally incorporate a plunger 172 to pressurize the fat for injection through the cannula 62 while mechanism 64 rotates to eject the fat. FIG. 16B shows a perspective view of the assembly and FIG. 16C shows another variation in the partial cross-sectional side view which incorporates an optional port 174 for allowing air to enter or exit during pressurization of the fat within chamber 170.

Figure 17A:
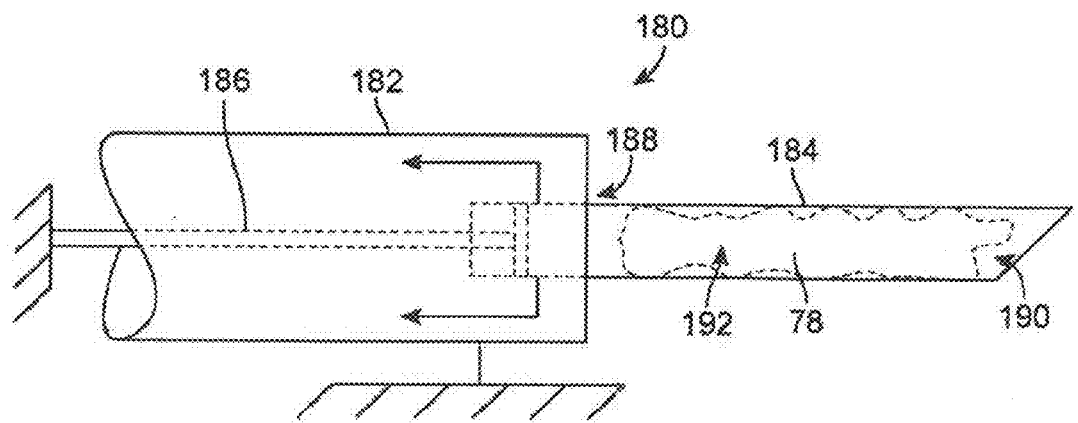
FIGS. 17A and 17B show side views of another variation of an injection instrument having a retractable cannula.
Figure 17B:
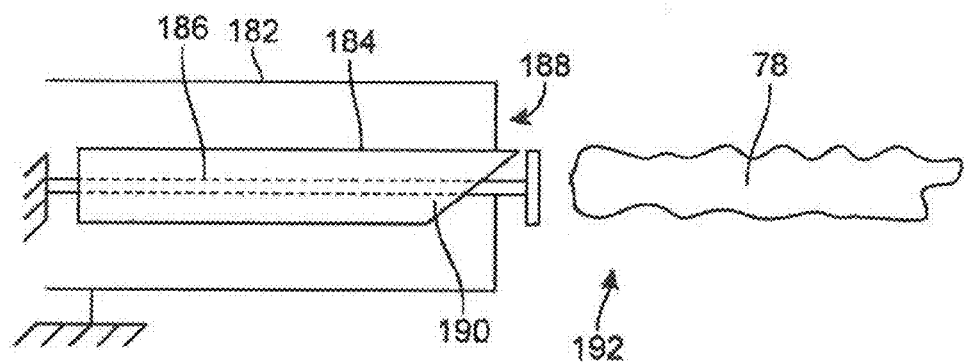

In yet another variation, FIGS. 17 and 17B show representative partial cross-sectional side views of an injection assembly 180 having a housing 182 with a retractable cannula 184 which may be withdrawn partially or entirely into the housing 182 during fat injection. A plunger 186 may be positioned within housing 182 to extend into a proximal portion of cannula 184. With cannula 184 filled with a quantity of fat 78, cannula 184 may be advanced percutaneously into the breast while under guidance (as previously described). Once a suitable location has been located within the breast, housing 182 and plunger 186 may both be maintained in a static position relative to the breast while cannula 184 may be retracted into the housing 182 through opening 188 in housing 182 relative to the breast proximally. Because the plunger 186 remains static relative to the cannula 184, the fat 78 contained within the cannula lumen 192 may be forced out through the distal opening 190 such that the ejected fat 78 is deposited along the tract previously formed by the cannula 184 within the tissue.

Figure 18A:
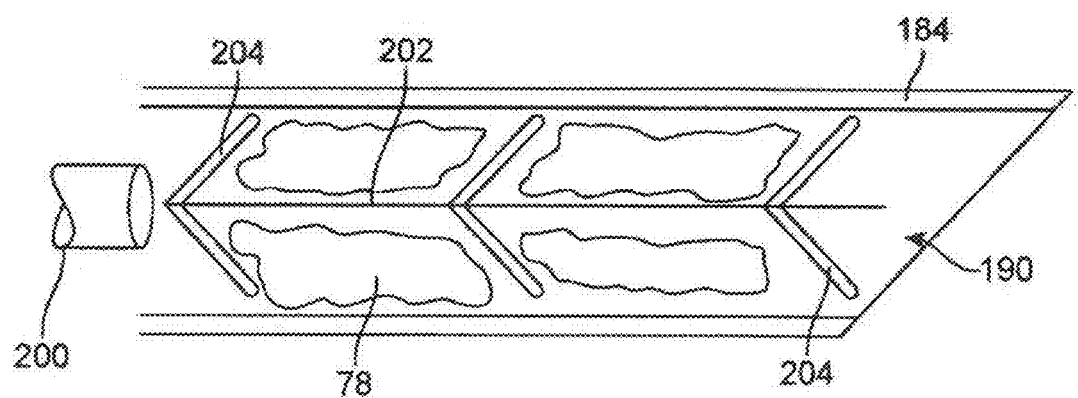
FIG. 18A shows a cross-sectional side view of another variation of an injection instrument having a collapsible inner sheath within a cannula.
Figure 18B:
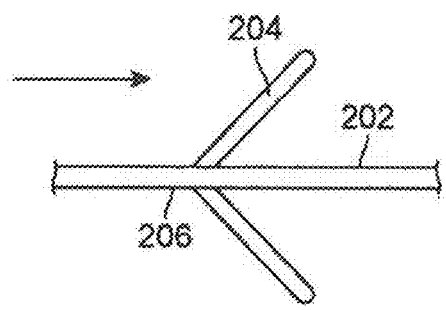
FIGS. 18B and 18C show side views of a retraction mechanism reconfigurable within the cannula.
Figure 18C:
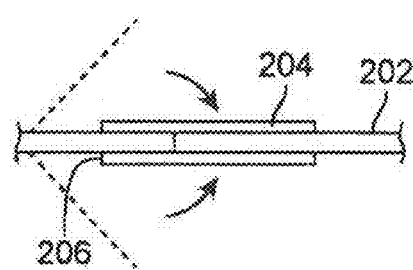

FIG. 18A shows another variation of the retractable cannula 184 having an actuation shaft 200 positioned within the cannula lumen. The actuation shaft 200 may have a support shaft 202 which extends through the cannula with one or more collapsible barbs 204 extending radially from the shaft 202. Boluses of fat 78 may be positioned between each of the barbs 204 which may help to compact the fat within the cannula 184 and prevent any buildup or introduction of air within the fat 78. FIGS. 18B and 18C show detail side views of one variation of the barbs 204 which may project at an acute angle relative to the shaft 202 such that the barbs 204 are angled to extend distally along the cannula 184. When shaft 202 is retracted proximally, each of the barbs 204 may pivot via a pivoting attachment 206 to collapse against shaft 202 to allow for the injection of the compacted fat 78 from distal opening 190 into the breast tissue.

Figure 19A:
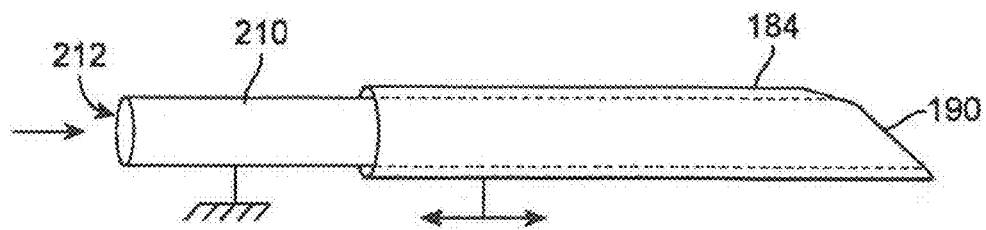
FIG. 19A shows a side view of another example of a needle cannula having a piston assembly.
Figure 19B:
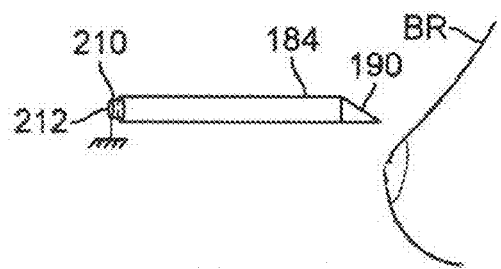
FIGS. 19B to 19D show side views of the needle cannula retracting relative to a breast to deposit a tract of adipose tissue within the breast.
Figure 19C:
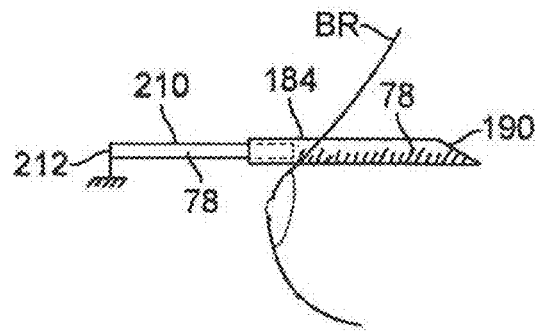
Figure 19D:
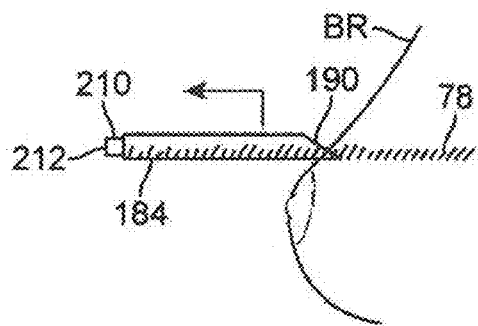

In yet another variation, FIG. 19A shows a representative side of a retractable cannula 184 (e.g., a 10 gauge needle cannula) having an inner piston shaft 210 which is translatable relative to the cannula 184. Piston shaft 210 may define a lumen 212 therethrough within which a volume of fat 78 may be placed. An example of use is shown in the side views of FIGS. 19B to 19D which illustrate how the needle cannula 184 may be retracted relative to the piston shaft 210 prior to percutaneous insertion into the breast BR, as shown in FIG. 19B. Prior to, during, or after the cannula 184 has been advanced into the breast BR and desirably positioned for injection (e.g., using the guidance devices and methods described herein), cannula 184 may be extended relative to the shaft 210 and a volume of fat 78 may be introduced into the cannula 184 through the lumen 212 of shaft 210, as shown in FIG. 19C. Once the volume of fat 78 is ready for injection into the breast BR, the cannula 184 may be retracted from the breast BR while maintaining a position of the shaft 210 relative to the breast BR such that a volume of fat 78 is injected into the breast BR along the tract formed by the withdrawn cannula 184, as shown in FIG. 19D.

Figure 20A:
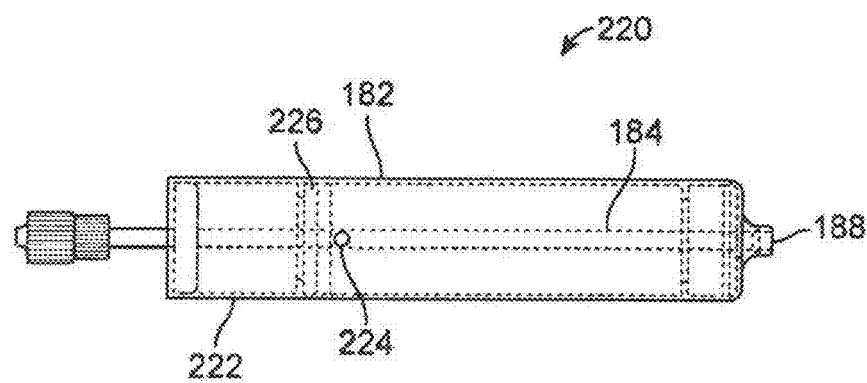
FIGS. 20A and 20B show side views of another variation of an injection instrument which may be pressure actuated.
Figure 20B:
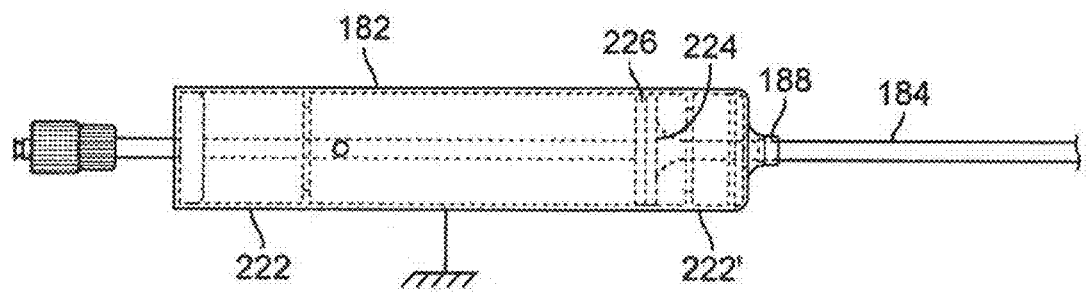

FIGS. 20A and 20B show side views of another variation of an injection assembly 220 which comprise a pressure actuated system. In this variation, cannula 184 may be attached at a cannula attachment 224 to a movable piston 226 which is slidable through the housing 182. A volume of fat may be introduced into the cannula 184 in its extended configuration which may be extended by introducing a gas or fluid into the proximal inlet 222, as shown in FIG. 20B. Once the cannula 184 has been desirably positioned within the breast BR, the cannula 184 may be retracted proximally into the housing 182 by introducing a gas or fluid into the distal inlet 222' to urge the piston 226 proximally within the housing 182 thereby retracting cannula 184, as shown in FIG. 20B.

Figure 21A:
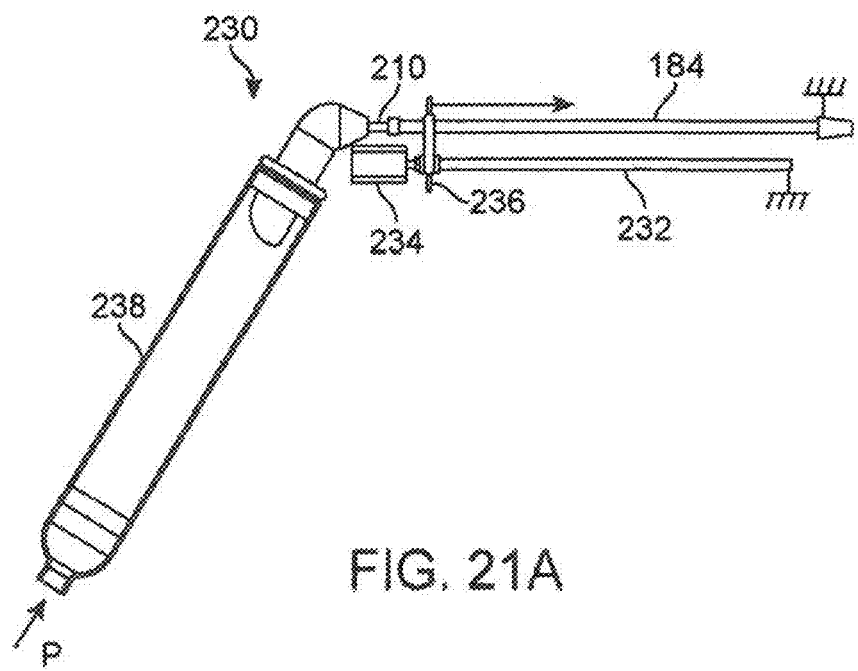
FIGS. 21A and 21B show side views of another variation where the injection instrument may be driven by a lead screw-type mechanism.
Figure 21B:
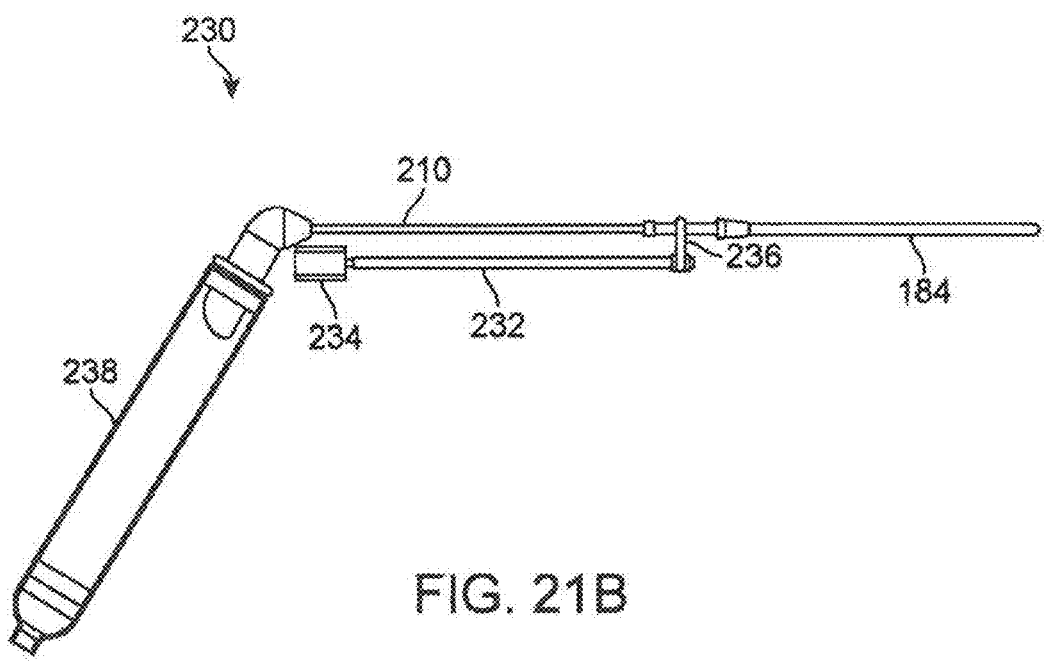

Instead of utilizing a pressure driven assembly, another injection assembly 230 variation shown in the side views of FIGS. 21A and 21B may use a linear threaded member 232 which is rotatably coupled to a motor 234 positioned within a housing. Here, the motor 234 may rotate the threaded member 232 in either direction to urge a carriage 236 which is threaded in a corresponding manner to move distally or proximally along the threaded member 232 depending upon the direction of rotation by the threaded member 232. Carriage 236 may be attached to a proximal end of cannula 184 such that as the carriage 236 travels along the threaded member 232 the cannula 184 may be retracted, as shown in FIG. 21A, or extended, as shown in FIG. 21B, as desired. A reservoir 238 (which may be pressurized) may be fluidly coupled to a proximal end of the cannula 184 so as to provide a volume of fat for injection through the cannula 184.

Figure 22:
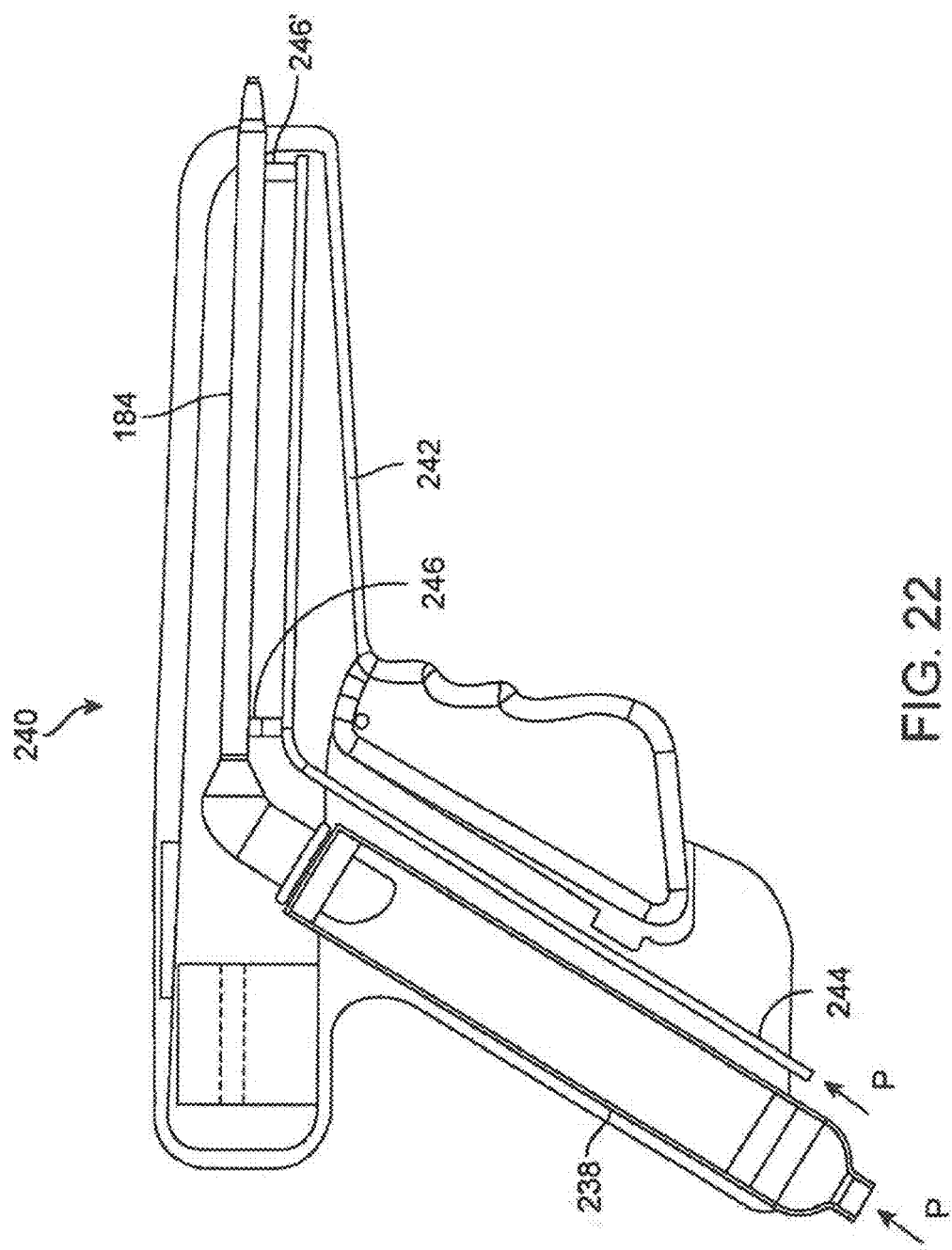
FIG. 22 shows another variation of an injection instrument using a pressurized mechanism.

FIG. 22 shows a partial cross-sectional side view of another injection assembly 240 variation which utilizes a pressurized cannula actuation system. Handle housing 242 may comprise a pressurizable line 244 which may be pressured at either a proximal inlet 246 or at a distal inlet 246' to actuate a piston attached to the cannula 184. Depending upon which inlet 246, 246' is pressurized, the cannula 184 may be retracted or extended for advancement into the breast and injection of fat accordingly.

Figure 23A:
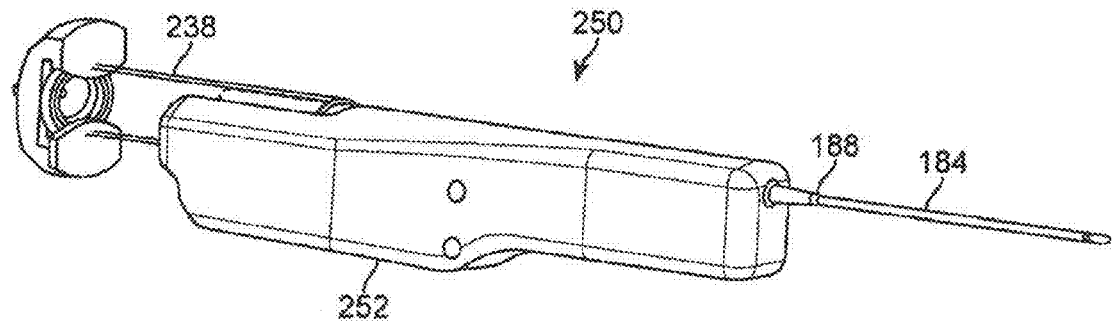
FIGS. 23A to 23C show perspective and side views of another variation using a lead screw-type mechanism with a retractable needle cannula.
Figure 23B:
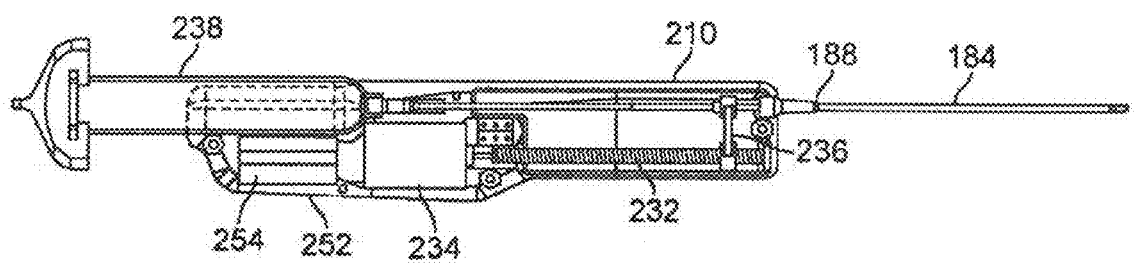
Figure 23C:
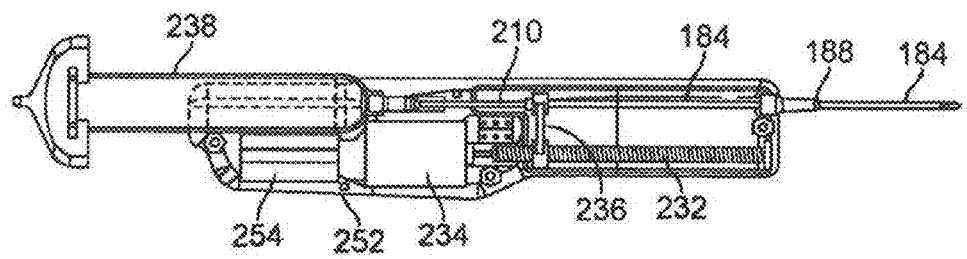
Figure 24A:
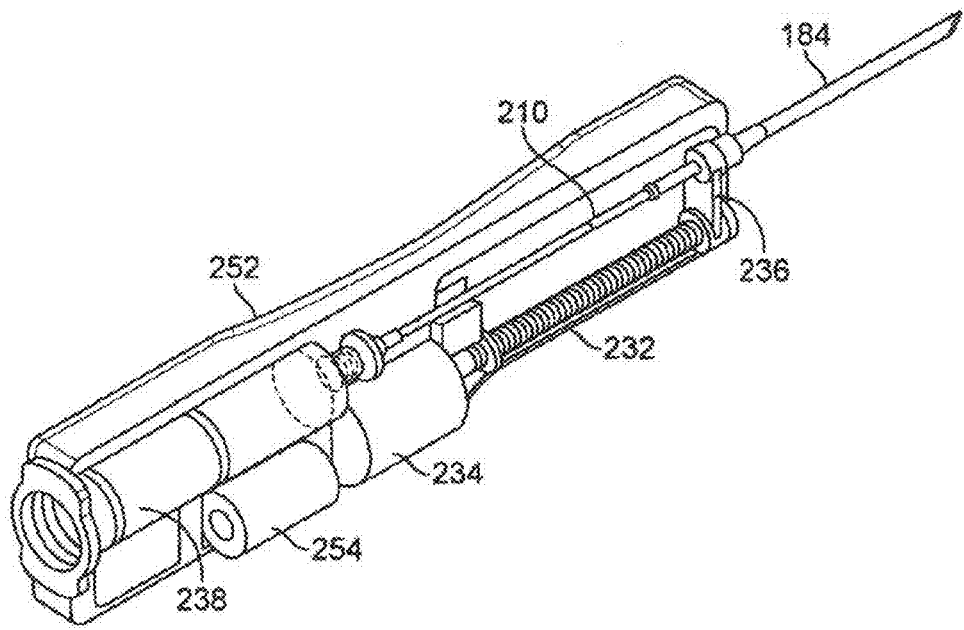
FIGS. 24A and 24B show perspective views of the instrument having a retractable needle cannula.
Figure 24B:
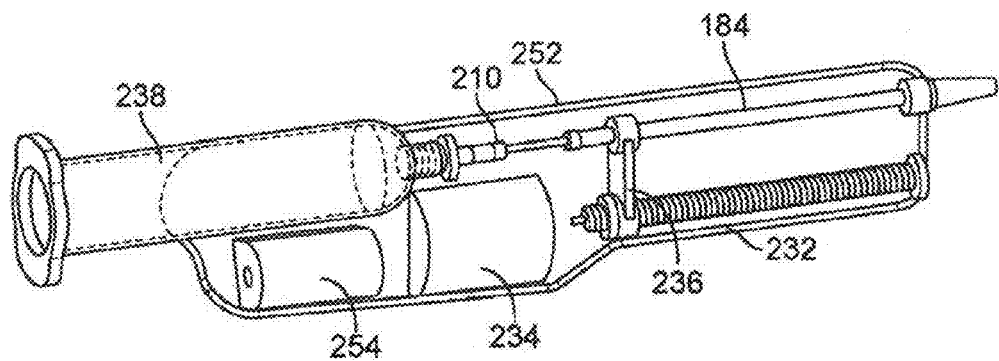

In yet another variation, FIGS. 23A to 23C show perspective and side views of an injection assembly 250 variation which utilizes a rotatable lead screw 232 to advance or retract a carriage 236 attached to a proximal end of cannula 184, similar to the variation described above in FIGS. 21A and 21B. In this example, handle housing 252 may contain a power supply 254 for driving the motor 234 to rotate the lead screw 232. FIGS. 24A and 24B show perspective views of the assembly 250 and FIGS. 25A and 25B show detail side views of the extension and retraction, respectively, of the carriage 236 to extend and retract the cannula 184 within housing 252 for injecting the fat. The retractable cannula may be utilized in any number of various cannula embodiments as described herein.

Figure 26A:
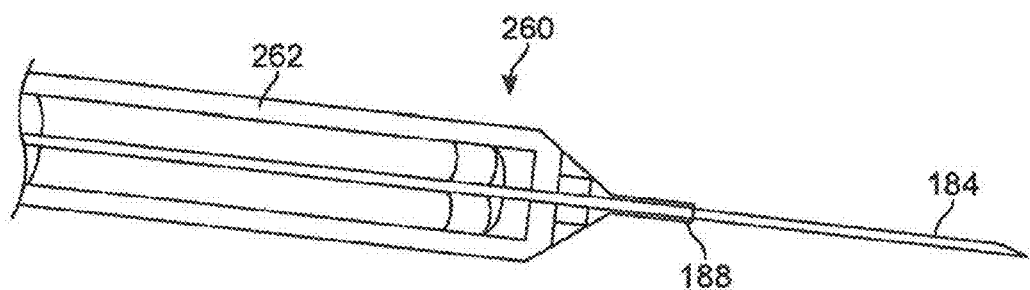
FIGS. 26A to 26C show perspective views of another variation where the retractable needle may be refilled once retracted.
Figure 26B:
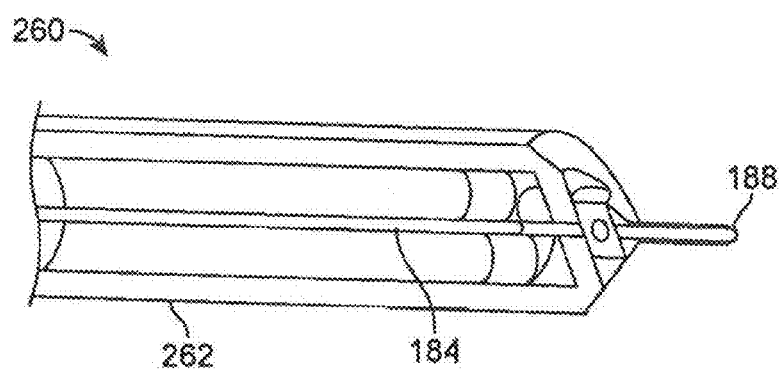
Figure 26C:
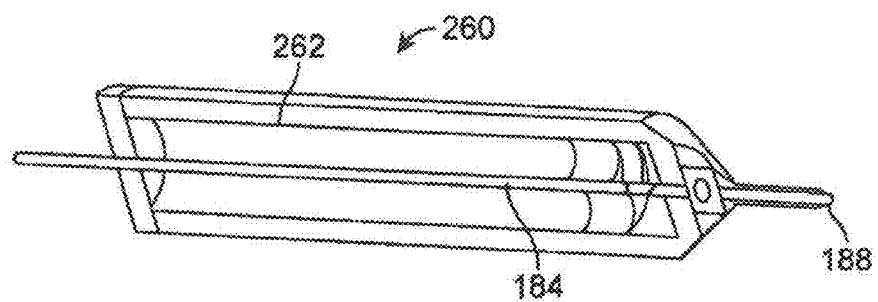

FIGS. 26A to 26C show perspective views of another variation of an injection assembly 260 which may comprise a handle housing 262 into which cannula 184 may be retracted using any of the mechanisms described herein. Housing 262 may incorporate a valve proximal to the opening 188 which may close once the cannula 184 has been retracted into housing 262, as shown in FIG. 26B, to allow the cannula 184 to be refilled with fat. Once the cannula 184 is ready to be retracted once again, the valve may be opened and the cannula 184 extended. In this as well as any of the injection instrument embodiments described herein, the tissue detection assemblies may be incorporated as desired.

As previously mentioned, fat may be harvested from a first site of the patient (e.g., periumbilical, lumbar, trochanteric, thigh, medial knee and arm, etc.) and this harvested fat may be purified prior to injection back into the patient. When harvesting the fat, the patient may be anesthetized and the lipoaspiration procedure may be performed.

While extraction may be performed using an aspiration cannula (e.g., 3-4 mm Mercedes or 14 gauge needle connected to a syringe), aspiration may be performed alternatively using a cannula, such as cannula 184, optionally having an alternative tip configuration depending upon the desired configuration for harvesting. The cannula 184 may be removed and/or replaced with another cannula for implantation, as previously described.

Additionally and/or alternatively, a cannula 184 incorporating the tissue detection assembly described herein may be used to facilitate the harvesting and extraction of the adipose tissue. In use, the cannula 184 may be advanced into the patient's body and the detection system as previously described may be used to detect for the presence of fat for extraction.

Once the fat has been harvested, it may then be purified by extracting viable adipocytes from the lipoaspirate material. Typically, the lipoaspirate material may undergo centrifugation to separate the adipocytes from the blood, serum, damaged cells, tumescent fluids, oil, etc. and the extracted adipose graft material may be transferred to standard syringes. Systems such as a VIAFILL™ (Lipose Corp., Maitland, Fla.) countertop centrifuge may be used to centrifuge and extract the adipocytes. A syringe, such as a short, broad 20 cc harvest syringe may be used to manually extract the viable adipocytes where the plunger arm may be removed for centrifugation and the extracted fat may be transferred directly to any of the reservoirs described herein, such as reservoir 238, for direct implantation using any of the devices described herein.

Figure 27:
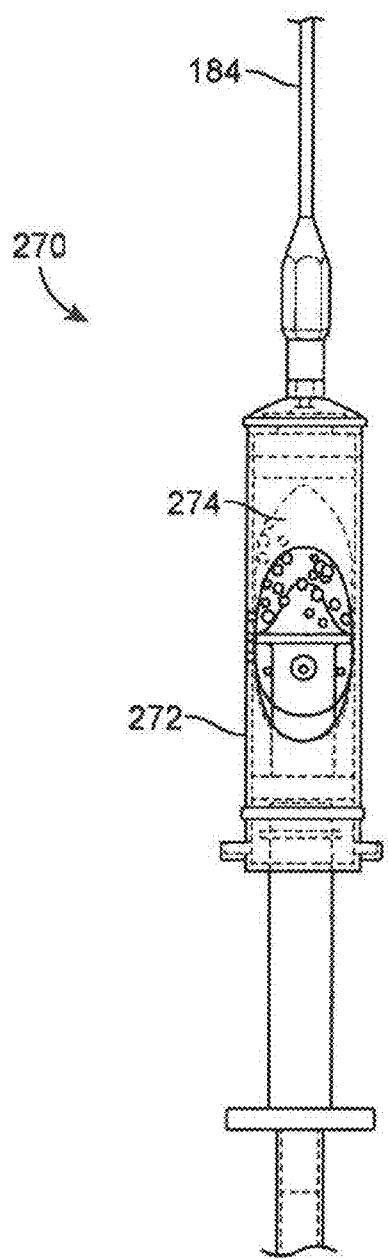
FIG. 27 shows a cross-sectional side view of an in-line filtration system which may be integrated with an injection instrument.

Moreover, an optionally disposable in-line filtration device such as LIPIVAGE™ (Genesis Biosystems, Lewisville, Tex.) may be used to harvest the fat. Such a device may be incorporated into the injection assembly to extract and purify the extracted material, e.g., 20-25 cc of fat, by automatically separating and washing the fat during the harvesting process utilizing internal filters. An example is shown in the side view of FIG. 27 illustrating an in-line filtration device 270 having an extraction reservoir 272 which one or more filters 274 integrated into the reservoir 272. The extracted material may be drawn into the device from the patient and through cannula 184 where it may be separated and washed. The purified fat contained within the reservoir 272 may then be removed from the device 270 for implantation using the devices and methods above or it may simply be injected directly into the patient using the filtration device 270 incorporated into the sensing and injection assemblies described above.

Further examples of in-line filtration devices and methods which may be incorporated into the injection assemblies herein are further shown and described in, e.g., U.S. Pat. Nos. 4,753,634; 6,258,054; 7,588,732; 7,780,649; and 7,794,449, each of which is incorporated herein by reference in its entirety.

Figure 28A:
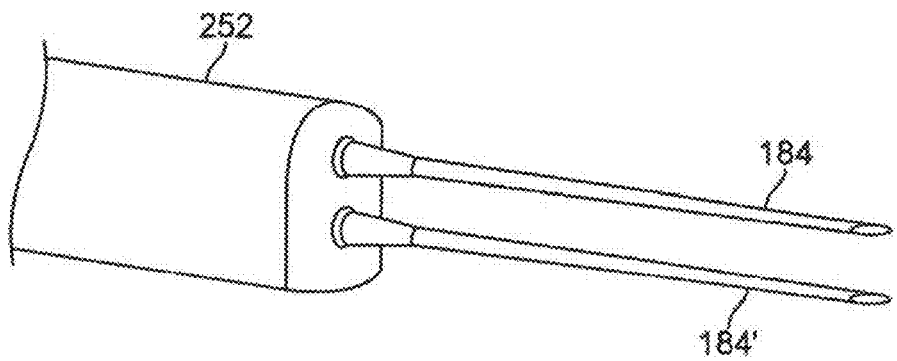
FIGS. 28A to 28C show perspective views of alternative variations injection instruments configured to have multiple cannulas and/or interchangeable cannulas.
Figure 28B:
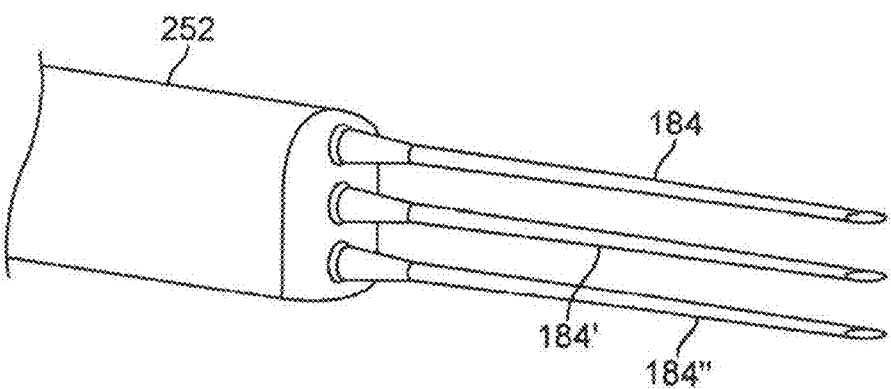

Additionally and/or optionally, any of the injection assemblies described herein may use multiple injection needles or cannulas, e.g., two or more, extending from a single housing to increase the volume and/or number of tracts per pass to increase the injected volume-per-surface ratio. These multiple cannulas may be arranged in various configurations (e.g., adjacent in a planar arrangement) and may use multiple cannulas as practicable. An example is illustrated in the perspective view of FIG. 28A which shows two cannulas 184, 184' projection from handle 252 adjacent to one another. FIG. 28B shows another example of three cannulas 184, 184', 184" projecting from handle 252. Additional cannulas may be incorporated as desired and practicable. In each of the examples, the cannulas may be configured to be retractable within the handle 252 and/or may incorporate a movable piston within each cannula as described herein for facilitate fat injection into the body.

Figure 28C:
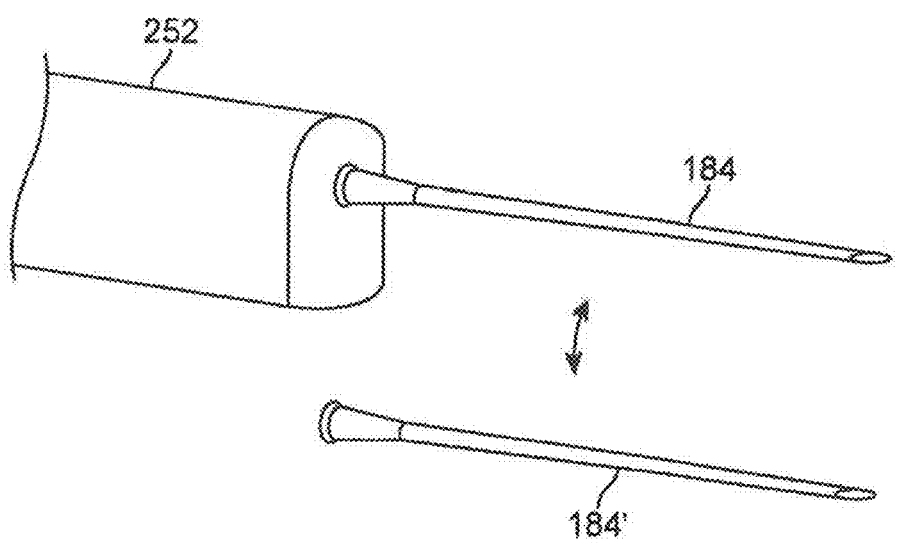

Another alternative variation is shown in the perspective view of FIG. 28C which illustrates an injection instrument having a cannula 184 which is interchangeable with a second cannula 184'.

Figure 29A:
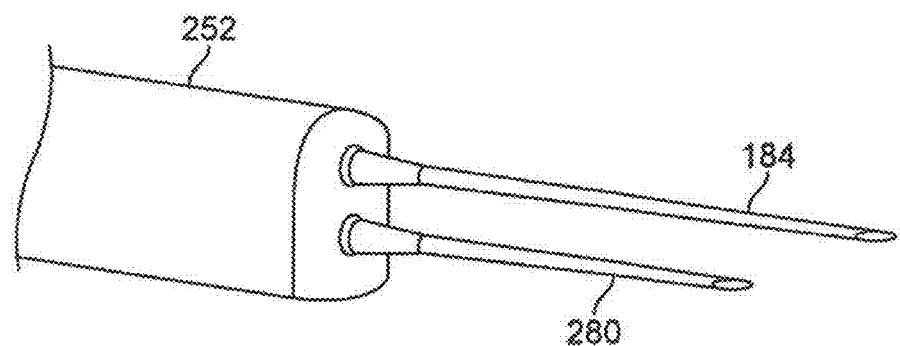
FIGS. 29A and 29B show perspective views of yet another variation having multiple cannulas where each successive cannula may have a length which is shorter to facilitate injection within a contoured body region such as a breast.
Figure 29B:
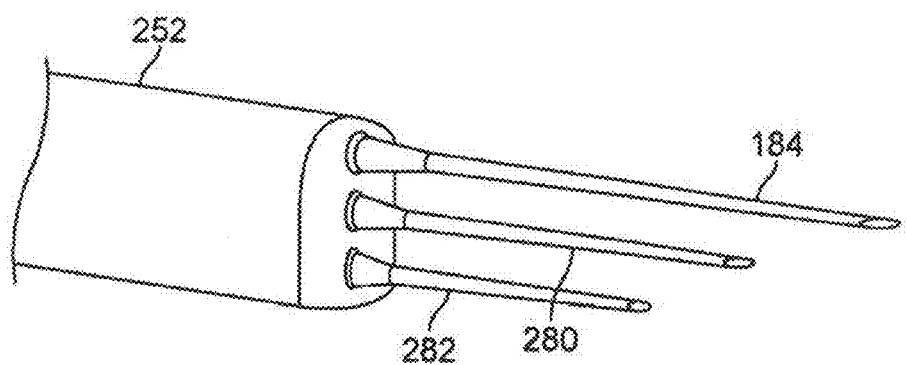

FIGS. 29A and 29B show perspective views of yet another variation having multiple cannulas where each successive cannula may have a length which is shorter to facilitate injection within a contoured body region such as a breast. In this manner, a single insertion and injection may be accomplished along curved regions of the breast without piercing through entirely. For example, FIG. 29A shows an instrument assembly having a first cannula 184 with a first length and an adjacent cannula 280 having a second length which is shorter than the first length. FIG. 29B shows another variation incorporating a third cannula 282 which has a third length which is yet shorter than the second length of the second cannula 280. Each length may be varied depending upon the desired lengths and/or anatomy of the body portion or breast to be injected. Moreover, each of these variations may incorporate retractable cannulas and/or movable pistons within the cannulas as described above.

Figure 30A:
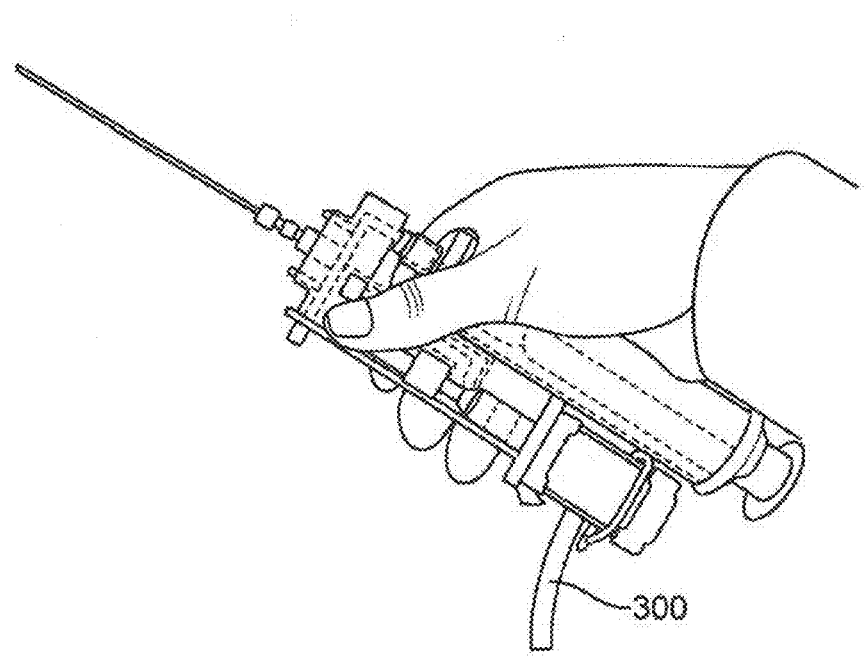
FIGS. 30A and 30B show perspective views of yet another variation where the fiber optic connection may be detachable from the system and reconnected in an axial arrangement.
Figure 30B:
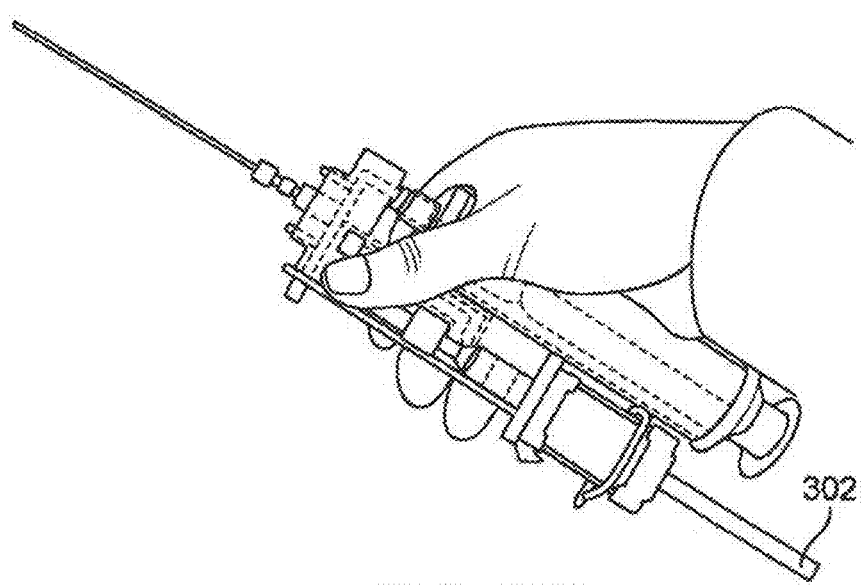

FIGS. 30A and 30B show perspective views of yet another variation where the harvesting instrument assembly may incorporate a reconfigurable fiber optic attachment. In this example, the fiber optic assembly positionable through the instrument may have a connection which is attachable to a cable assembly 300 at a first configuration, e.g., extending from a side of the instrument. The cable assembly 300 may be detached from the instrument and re-coupled into an axial configuration 302. In this manner, the fiber optic assembly within the instrument may be maintained as a modular system since cable assembly 302 may reconnect to the fiber optic assembly within the instrument.

Figure 31:
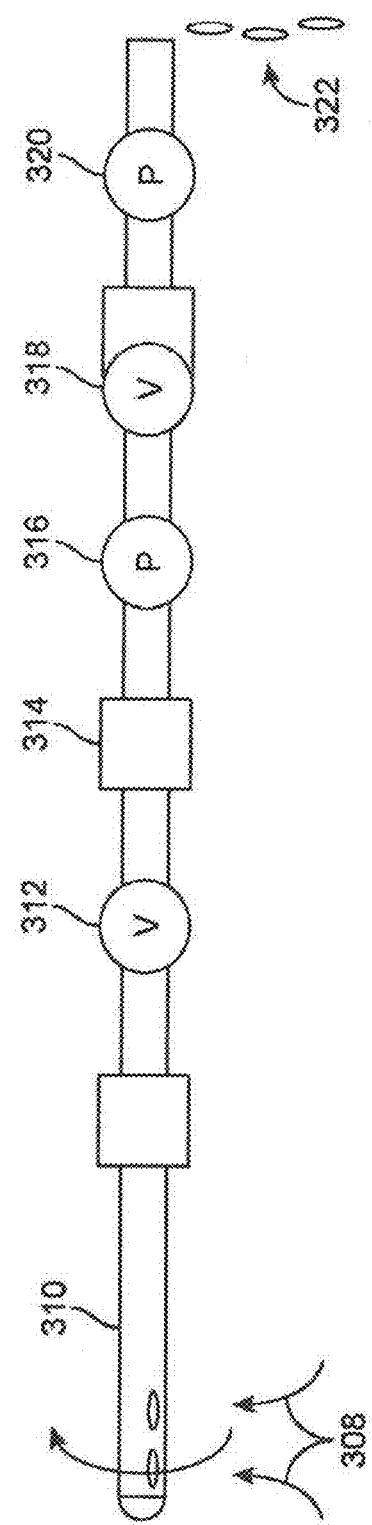
FIG. 31 shows a schematic illustration of an example of a complete harvesting, processing, and injection system which is coupled to one another such that a consistent and relatively low pressure may be maintained throughout the entire process and system.

In yet another variation, FIG. 31 shows a schematic illustration of a complete fat harvesting, processing, and injection system which is coupled to one another in a manner which provides a consistent and relatively low pressure (e.g., a maximum pressure of 700 mmHg) throughout the entire harvesting, processing, and injection procedure. As shown, the fat 308 may be initially harvested via the instrument 310 described herein. The harvested fat 308 may be drawn via a gentle vacuum 312 and introduced into a pressurized processing reservoir 314. With the fat collected and processed within the reservoir 314, a pressure 316 and a vacuum 318 may be simultaneously imparted upon the fat 308 contained within the system such that the net force experienced by the processed fat is low or close to zero. The low pressure imparted on the fat helps to maintain viability of the tissue.

With the fat drawn through the system, the processed fat may then be pressurized 320 for introduction 322 back into the selected region of the body. Accordingly, the entire procedure for harvesting, processing, and injection may be contained within a common closed system which imparts a relatively low pressure to maintain tissue viability as well as providing for a complete system which reduces or eliminates several steps. Additionally, the overall system further prevents the exposure of the adipose tissue to ambient air and to the environment to further reduce or minimize any additional trauma to the tissue. Moreover, the system may measure the pressure within the cannula, handle, or any of the other components during harvesting and/or injection, e.g., via any of the processors or controllers described herein, to ensure that any trauma upon the tissue is minimized. In the event that the monitored pressure exceeds a predetermined level, the processor or controller may be programmed to reduce the pressure, cease activity, or alert the user with a visual and/or audio indicator.

Figure 32:
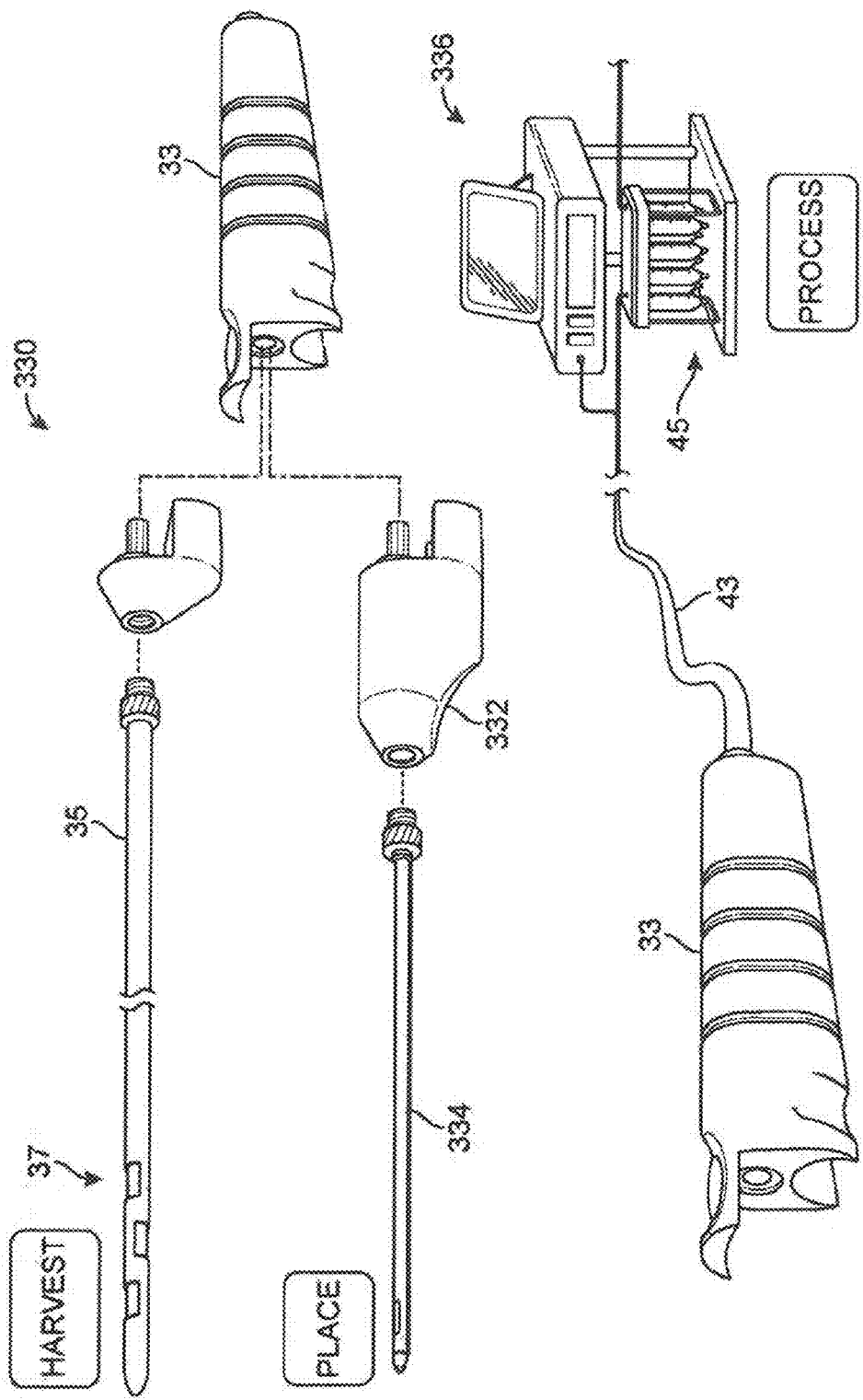
FIG. 32 shows an assembly view of a combined fat harvesting and injection assembly utilizing a single handle and controller.

Further examples of a combined fat harvesting and injection assembly are shown in the assembly view of FIG. 32. In this variation, a single handle 33 may be used with either a harvesting cannula 35 having the one or more openings 37 and/or with a fat injection cannula 334 which may be detachably removable via interface 332 to handle 33. The handle 33 may be fluidly coupled via tube 43 to the harvesting reservoir 45 described above and the process may be controlled and/or monitored via a processor 336 which may control the harvesting rates, pressures, flow rates, etc. as well as the injection parameters such as tissue identification, injection rates, etc.

Additionally and/or alternatively, in this and other variations the detachable injection cannula 334 may be variously configured. For example the injection cannula 334 may be configured to have an integrated plunger within a lumen of the cannula 334 and a retractable cannula which may be translated proximally relative to the handle 33 to deposit a known quantity of fat into the body along a tract formed by the cannula itself. Examples of such a mechanism are described above, e.g., in FIGS. 23A to 23C.

Figure 33:
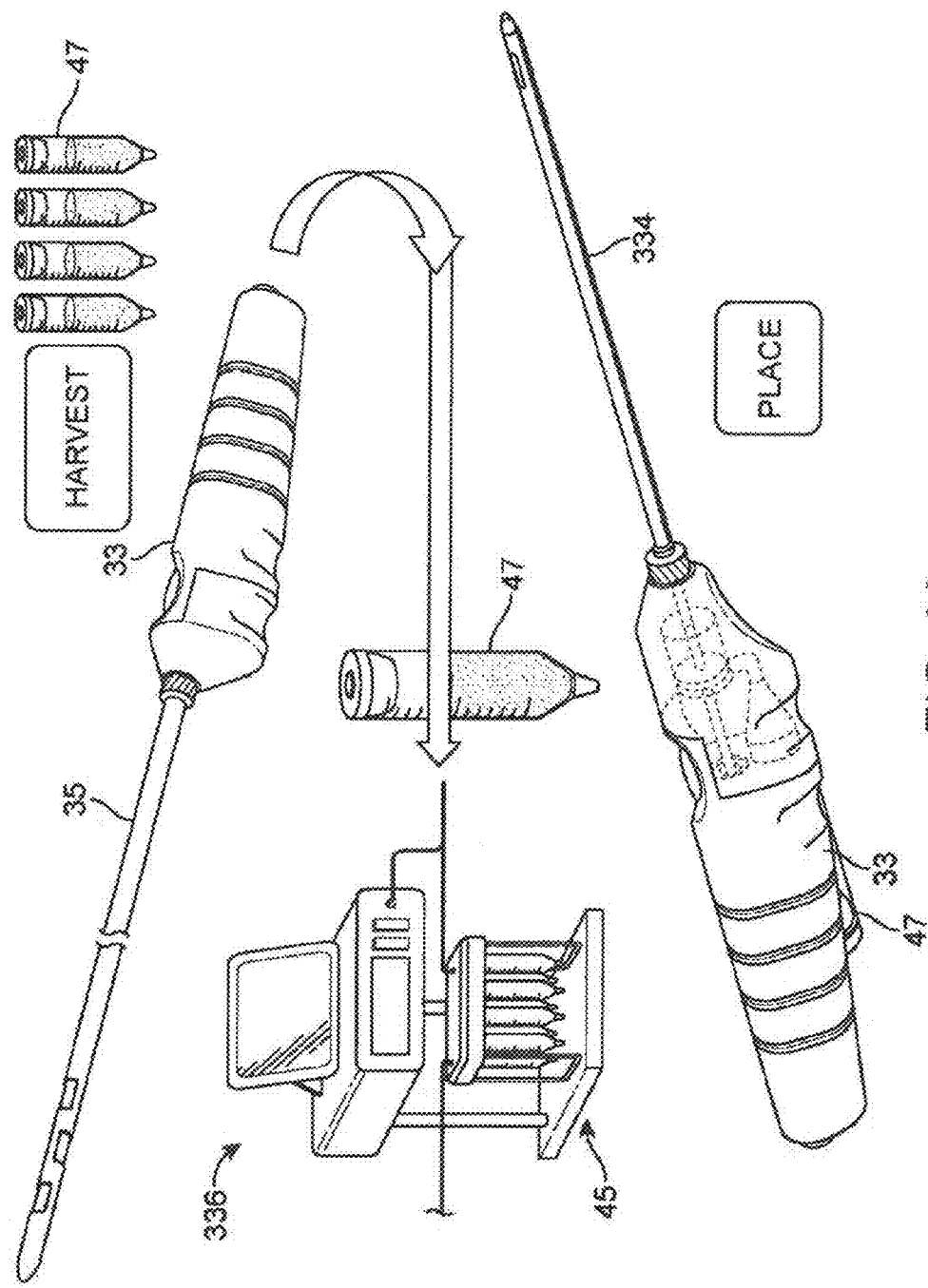
FIG. 33 shows an assembly view of another example illustrating how the handle with a detachable harvesting cannula may be used for harvesting the fat for processing and then used also for injection into the patient body with a detachable injection cannula.

Another example is shown in the assembly view of FIG. 33 which illustrates how the handle 33 with the harvesting cannula 35 may be used to harvest one or more cartridges 47 of fat and tissue from the patient body. This harvested fat may be collected via the reservoir assembly 45 and controlled by the processor 336. Once the fat has been desirably processed, the cartridge 47 may be fluidly connected to the same handle 33 or to a different handle and introduced into the patient body using an injection cannula 334, as described above.

Figure 34:
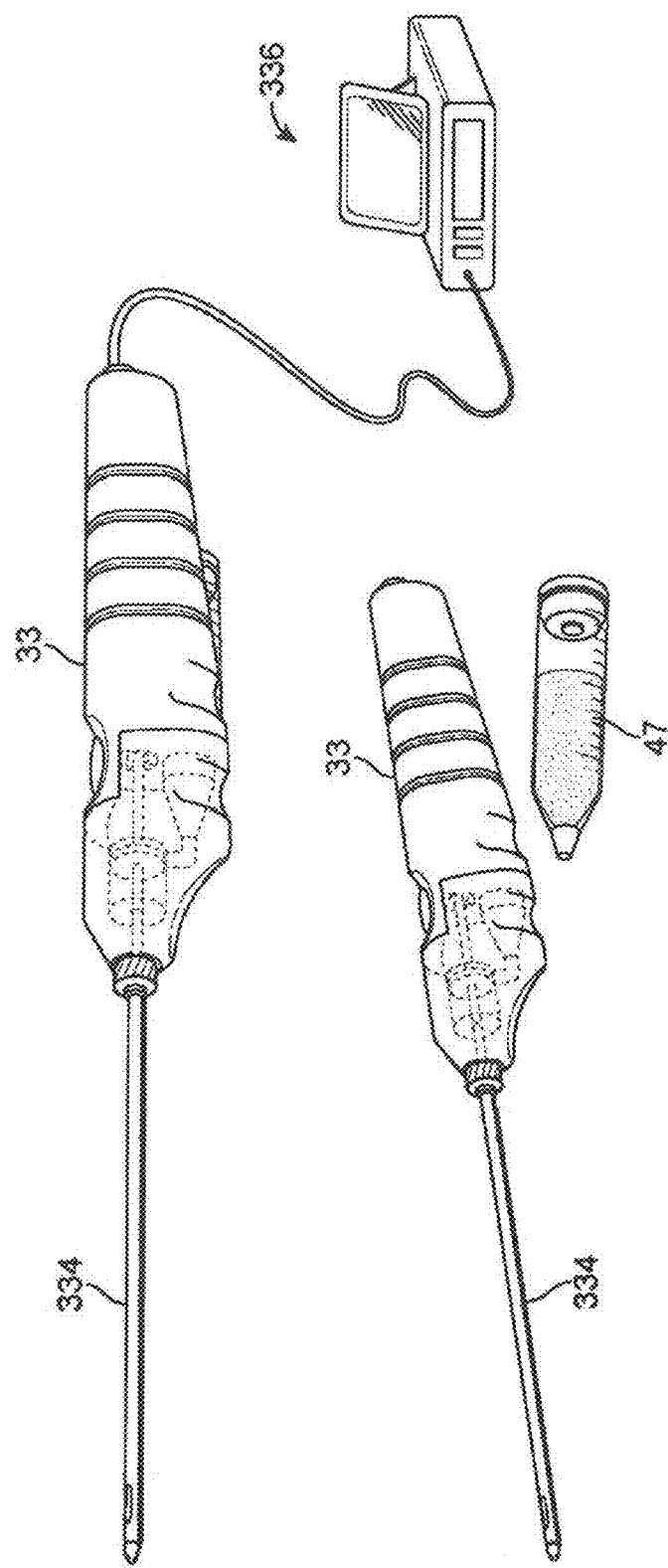
FIG. 34 shows an assembly view of another example of how an individual cartridge having processed fat may be coupled directly into the handle for injection into the body.
Figure 35A:
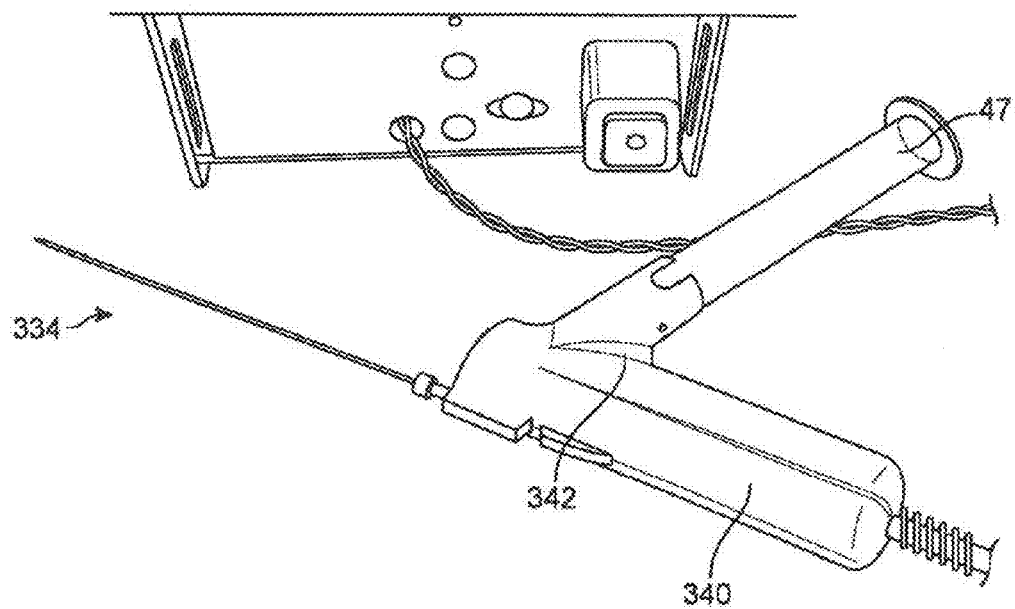
FIGS. 35A and 35B show perspective views of another variation of a handle assembly attached to an injection cannula and further having an angled receiving section for receiving an individual cartridge having processed fat for injection.
Figure 35B:
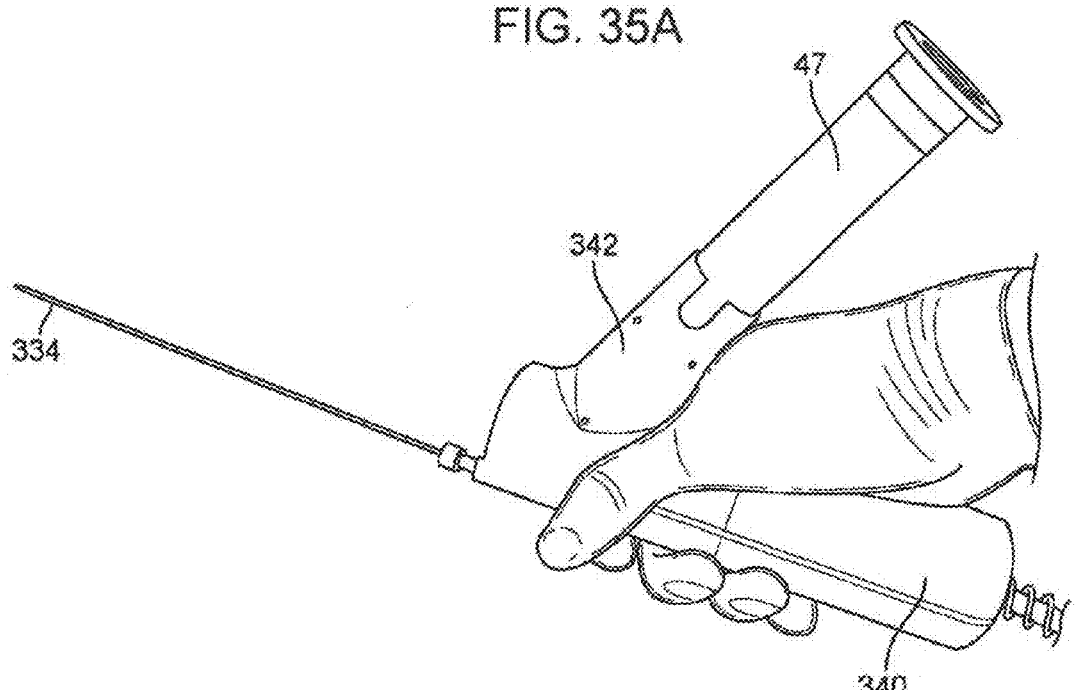
Figure 36A:
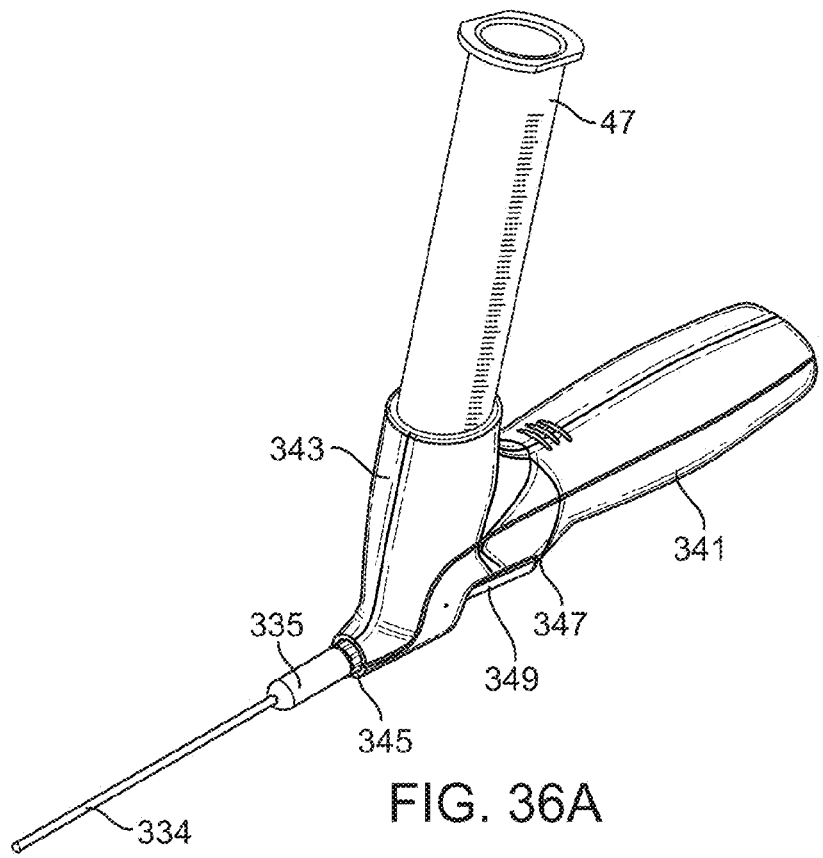
Figure 36B:
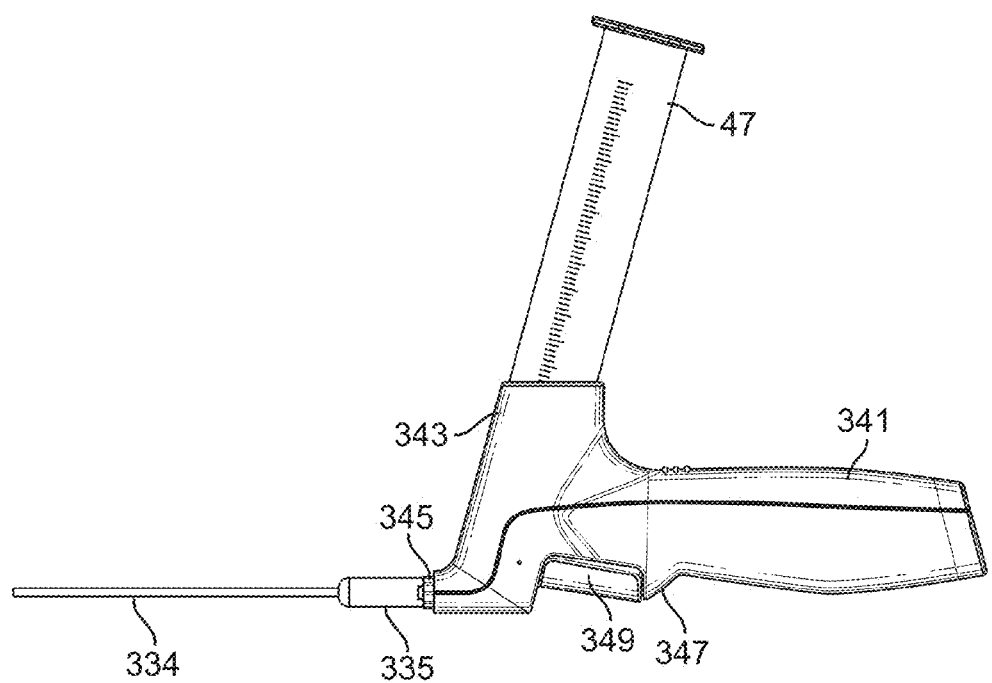
Figure 36C:
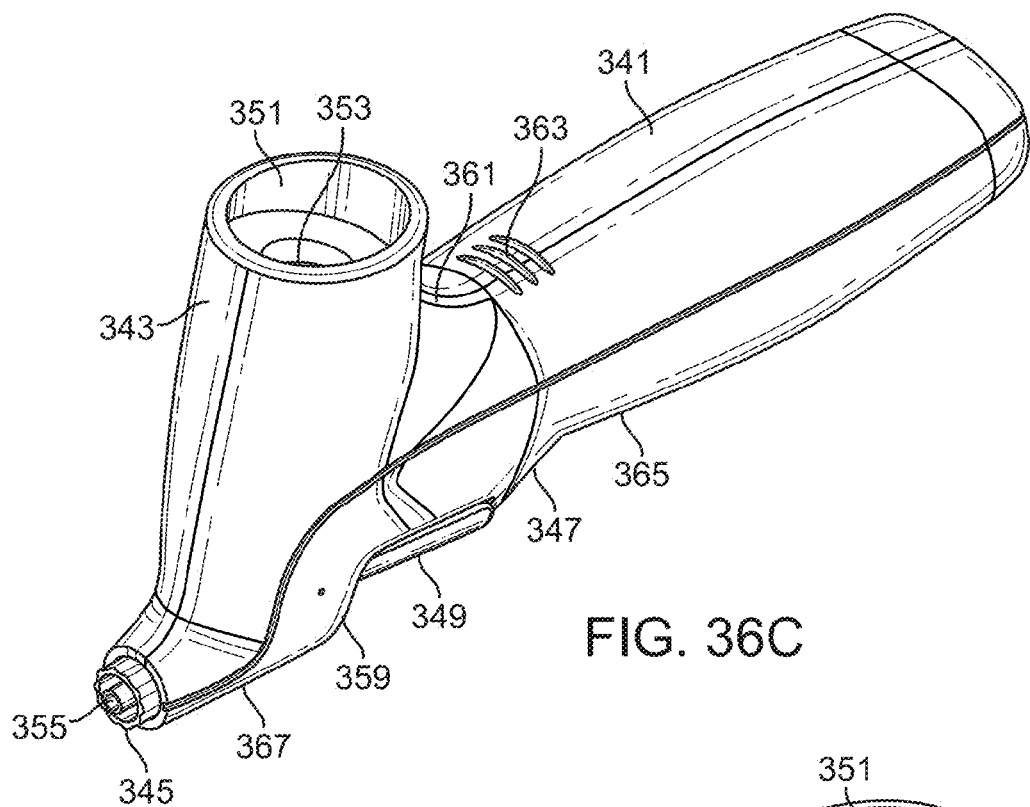
Figure 36D:
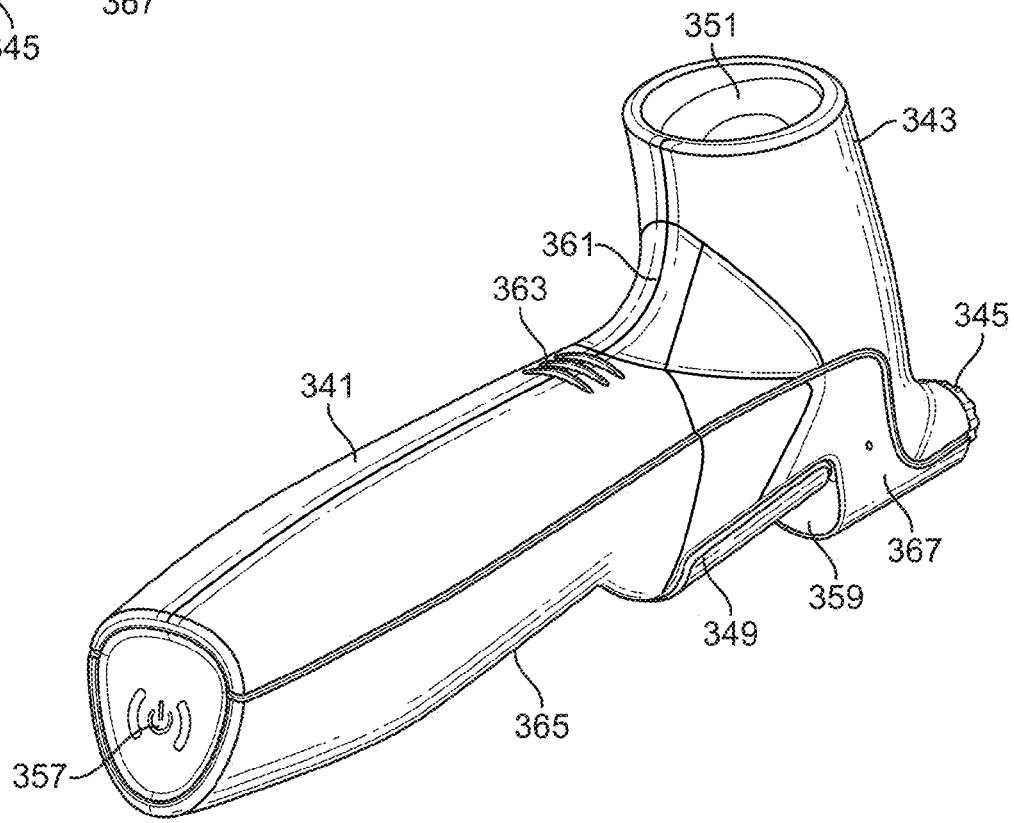

An example of a variation of the handle 33 is illustrated in the assembly view of FIG. 34, which shows handle 33 with cartridge 47 coupled directly into the handle for introducing the fat into the patient body. FIGS. 35A and 35B show perspective views of another variation of a handle assembly 340 attached to an injection cannula 334 and further having an angled receiving section 342 for receiving an individual cartridge 47 having processed fat for injection. The angled section 342 may orient the cartridge 47 at an angle relative to the handle 340 to facilitate the manipulation of the handle 340 as well as to facilitate the introduction and removal of the cartridge 47 from the handle 340.

Yet another variation of a handle assembly 341 having an angled receiving section 343 for receiving a cartridge 47 or reservoir, e.g., syringe, is shown in the FIGS. 36A to 36J. In this variation, the handle assembly 341 may be configured as a portable and self-contained device which may be used, in this example, to take the fat tissue contained within cartridge 47 and inject it into a patient body through the attachable injection cannula 334. Cartridge 47 may remain exposed relative to the handle assembly 341 to provide immediate and unobstructed visual feedback to the user with respect to the tissue volume remaining within the cartridge 47, as shown in the perspective and side views of FIGS. 36A and 36B, particularly during use for injection into the patient body.

The cannula 334 may be coupled via cannula attachment 335 to cannula coupler 345 which may extend from the angled receiving section 343 to present a relatively small surface area at its outlet so as to maintain minimal patient contact. When cannula 334 is attached to handle assembly 341, cannula 334 may project distally while off-set at a distance relative to handle assembly 341. Moreover, the handle assembly 341 may incorporate the receiving section 343 which may be angled relative to the handle. The receiving section 343 may define a cartridge receiving channel 351 which also defines a cartridge opening 353 which may be configured as a universal interface for receiving any number of cartridge configurations, as shown in the perspective views of FIGS. 36C and 36D. Cartridge receiving channel 351 and opening 353 may be optionally interchangeable to receive any number of different cartridge configurations if so desired.

Because the cannula 334 and cannula coupler 345 may be off-set relative to the handle assembly 341, the receiving section 343 may continue to an off-set attachment assembly 367 which may also define a control surface 359 along a proximal portion for pressing one or more fingers against to provide for leverage in pushing the assembly 341 in a distal direction, if needed, as shown in the side view of FIG. 36F. The cannula opening 355 may also be seen in the end view of FIG. 36E for passing the fat tissue through from the cartridge 47 and into and through the cannula 334.

Additional control surfaces may be provided over the handle assembly 341 for facilitating manipulation of the handle assembly during use. For instance, a trigger guard 347 which may project at an angle from handle assembly 341 may prevent inadvertent depression of the actuation trigger 349 and may also help to guide the user's fingers to the trigger 349 as well as provides for a rest position for the user's fingers as well. The actuation trigger 349 may be sized to provide space for one or more fingers of the user for pressing against to deliver the fat tissue through the cannula 334.

The handle assembly 341 may also define additional control surfaces such as control surface 361 which may be curved between the interface of the handle assembly 341 and angled receiving section 343 for providing a surface for the webbing between the user's thumb and fore finger. Control surface 365 may also be angled relative to the handle assembly 341 and trigger guard 347 to provide for a manipulation surface by the user's fingers. Additionally, one or more projections 363 may also be provided along the handle assembly 363 to increase the gripping strength of the user's hand against the handle assembly 341.

Additionally, the handle assembly 341 may also incorporate a controller 357 (optionally lighted or able to be illuminated) which may be recessed relative to the handle 341 to prevent inadvertent actuation. The controller 357, as shown in the end and side views of FIGS. 36G and 36H, may be pressed to turn the assembly on or off as well as to control any number of aliquot delivery parameters, as described in further detail below. FIGS. 36I and 36J further illustrate top and bottom view of the handle assembly 341.

Figure 37A:
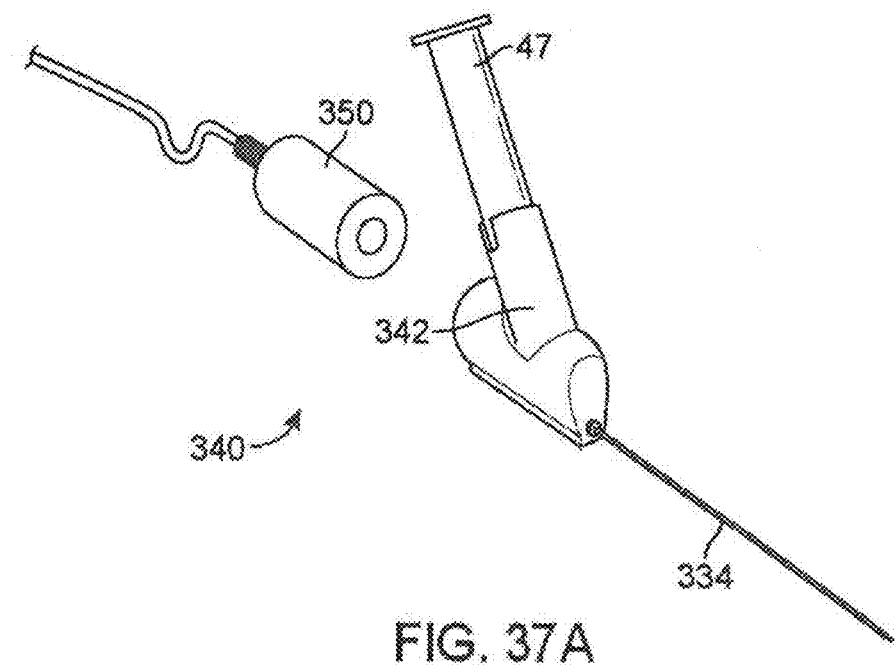
FIGS. 37A and 37B show perspective views of another variation of the handle assembly illustrating how the handle may be separated into at least two components.
Figure 37B:
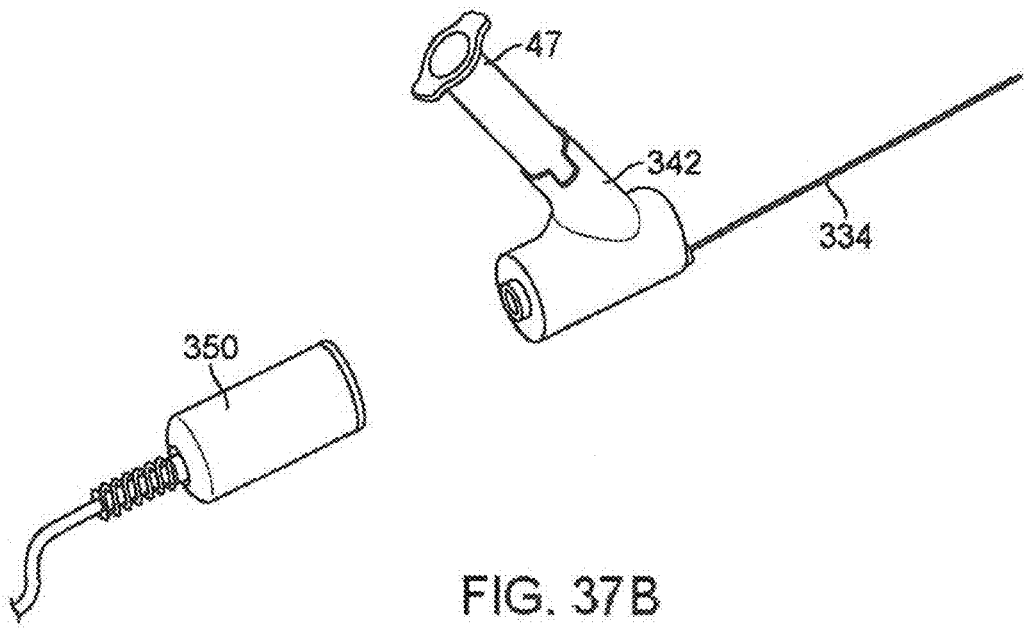

FIGS. 37A and 37B show perspective views of another variation of the handle assembly 340 illustrating how the handle may be separated into at least two components. A resusable component 350 may contain the pumping mechanism, electronics, controller, etc. and may be detachable coupled to a disposable portion containing the angled section 342 as well as the cartridge 47 and/or cannula 334.

Figure 38A:
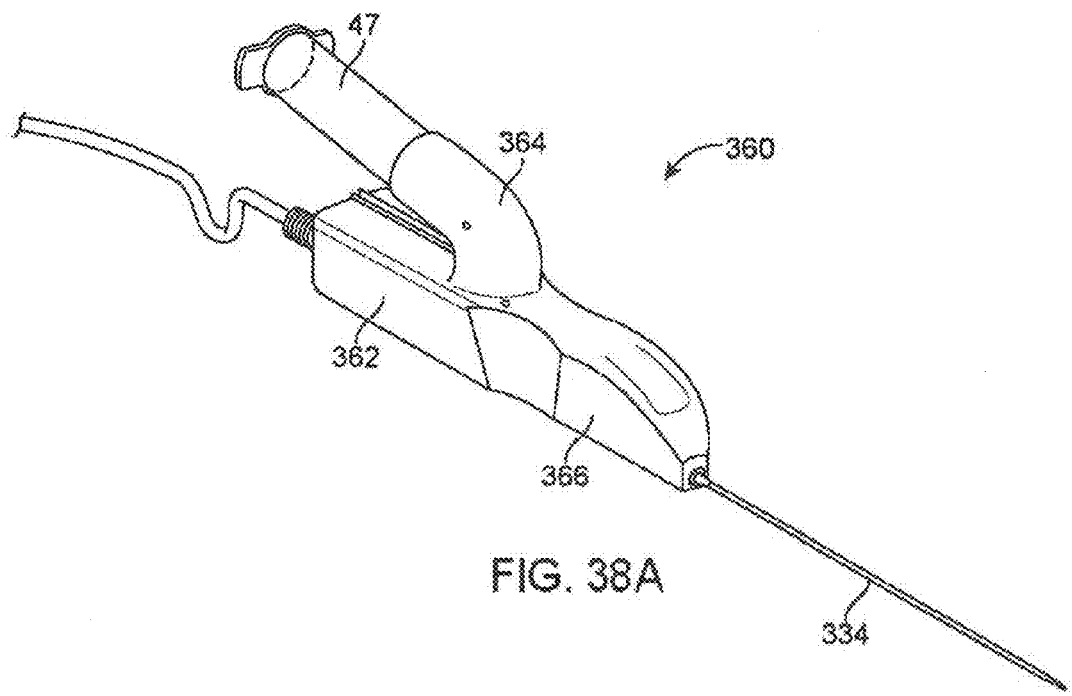
FIGS. 38A and 38B illustrate perspective views of another variation of a handle assembly which may also comprise a resusable component as well as a disposable component having an angled section.
Figure 38B:
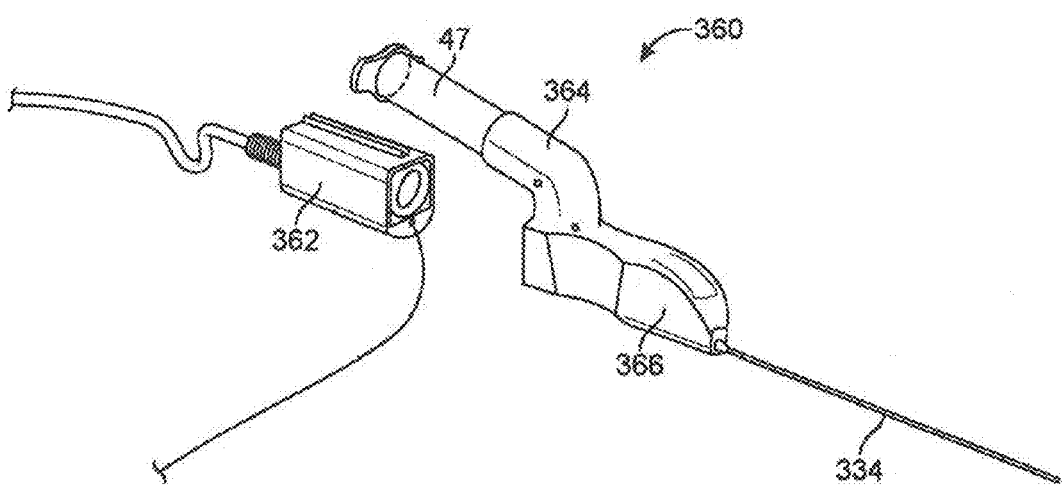

FIGS. 38A and 38B illustrate perspective views of another variation of a handle assembly 360 which may also comprise a resusable component 362 as well as a disposable component 366 having an angled section 364 which may hold the cartridge 47 at a more acute angle relative to the handle 360.

Figure 39A:
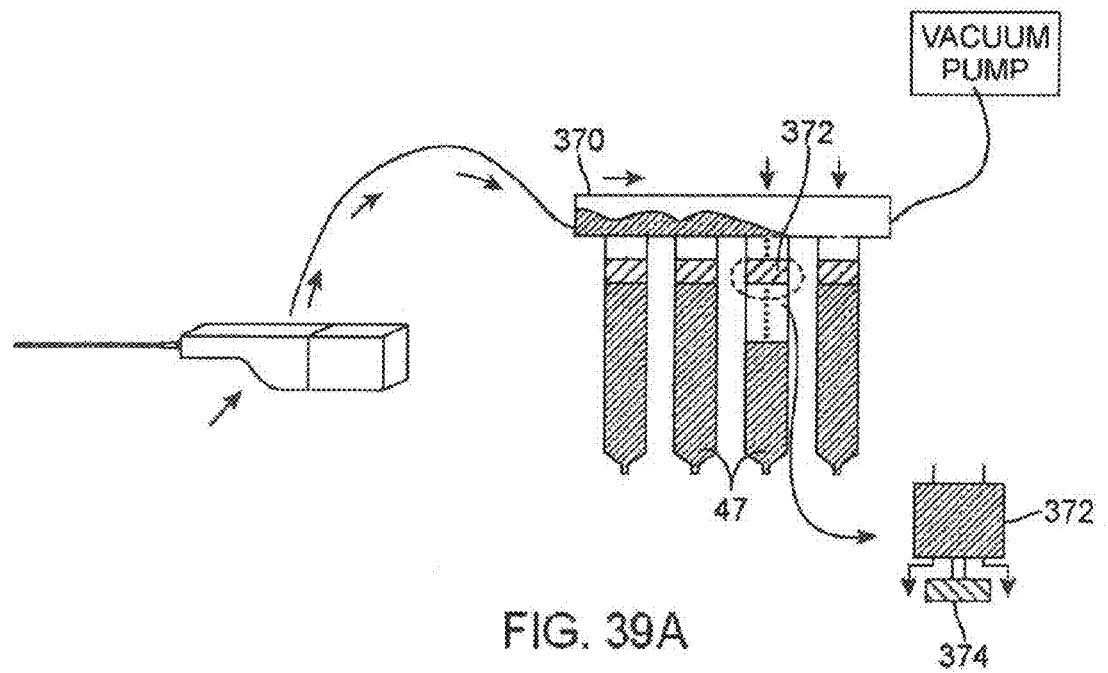
FIG. 39A schematically illustrates one example of how the individual cartridges may be filled with the harvested fat collected from the harvesting cannula.

FIG. 39A schematically illustrates one example of how the individual cartridges 47 may be filled with the harvested fat collected from the harvesting cannula. As previously described, the harvesting assembly may utilize one or more individual cartridges 47 which are fluidly open to receiving the harvested material, as shown. Each of the cartridges 47 may be detachable coupled to a base dock 370 and each cartridge 47 may incorporate a valve 374 with a plunger 372 which remains in an open position for receiving the harvested material introduced through the base dock 370.

The individual cartridges 47 may generally comprise conventional syringes arranged in a consecutive fashion. The system may contain the base dock 370 with several ports that allow each of the cartridges 47 connected to fill with the fat. As the individual cartridges fill, they may each close their respective plunger 372 to shut off the valve 374.

Figure 39B:
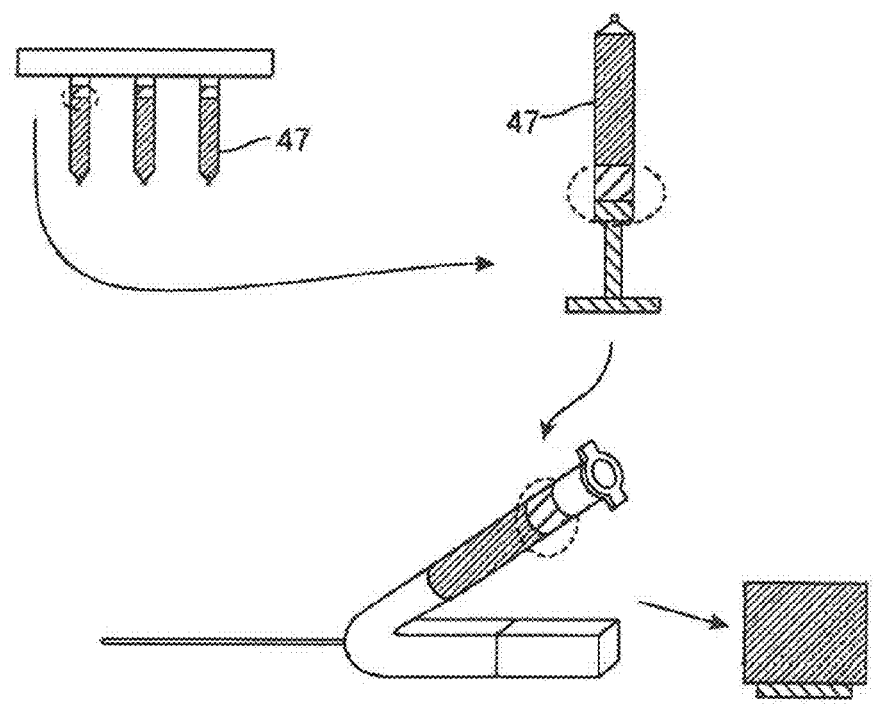
FIG. 39B schematically illustrates an example of how the individual cartridges may be purged of air or other material and incorporated into the injection assembly.
Figure 40:
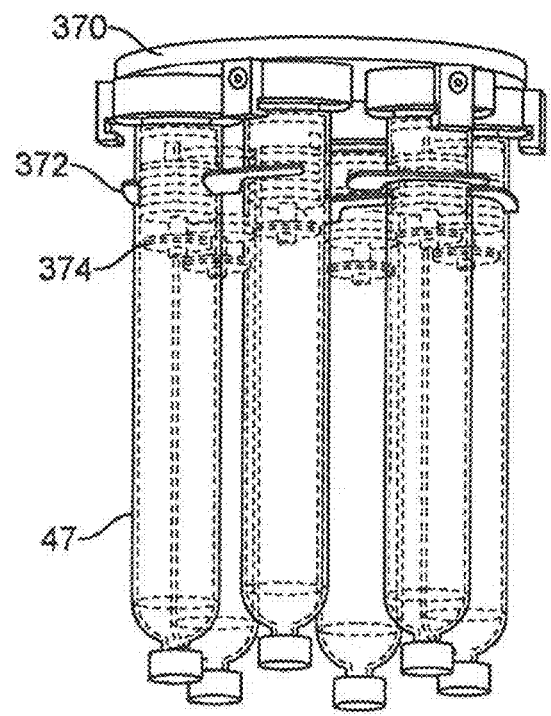
FIG. 40 shows a perspective view of one configuration of cartridges coupled to a base dock.

Fat may be transported into the cartridges 47 through the use of a vacuum that is hooked into the base dock 370. The ports may be placed in series allowing the fill of each consecutive syringe before moving on to the next. Configuration of the cartridges 47 can be placed in line or in a circular fashion, so long as it is in series, as shown in the perspective assembly view of FIG. 40. When the harvesting procedure is finished, cartridges 47 may have its respective fat fill. The user can then remove the fat filled cartridges 47 and purge the air, as shown in FIG. 39B.

Figure 41:
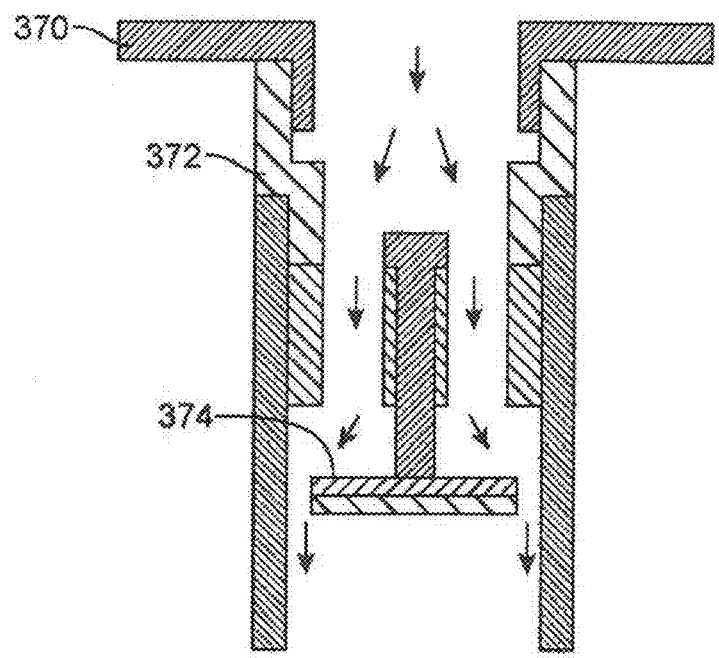
FIG. 41 shows a cross-sectional side view illustrating one configuration for a valve and plunger assembly incorporated into a cartridge.

Each cartridge 47 may integrate its own plunger 372 throughout the life the device. The plunger 372 may allow for fat fill when the cartridge 47 is engaged into the port adapter of the base dock 370. The fat may flow through the plunger 372 and around the valve 374, as shown in the cross-sectional side view of FIG. 41. Another variation is shown in the cross-sectional and perspective views of FIGS. 42A and 42B which illustrate a plunger 372 defining one or more openings therethrough which may provide adequate space with a cross sectional area between, e.g., 0.15 to 0.20 $in^2$ for the fat to flow through, while maintaining the integrity as a plunger.

The plunger 372 may also be used as a vacuum plunger when the device is placed into the injection device. As the injection device draws the fat, the plunger 372 may move according to the vacuum rate, as shown in the side view of FIG. 43. The plunger 372 may incorporate O-rings 380 that allow a dynamic seal, the ability to move while sealing against the mating surface. With the vacuum pull of the injection device operating less than 20 in Hg, the plunger is able to move with less than 2.0 LbF of pull.

The plunger 372 may further contain a piston valve 382 that is mechanically opened and automatically closed, as shown in the cross-sectional side views of FIGS. 44A and 44B. The sealing valve size may be tuned to allow fat flow when opened during the harvesting procedure but also prevent air and liquid leakage when closed during the injection procedure. The valve 382 outer diameter may be greater than, e.g., 0.626 in, to provide a seal. The valve 382 may be less than, e.g., 0.875 in, to allow flow around it. The distance to which the valve 382 is moved away from the plunger 372 when opened is also tuned to allow for easy fat fill. A distance of at least, e.g., 0.125 in, from gasket to plunger 372 to allow fat to flow through. The valve 382 may also include a soft gasket that may seal against the opening plunger 372.

Figure 45:
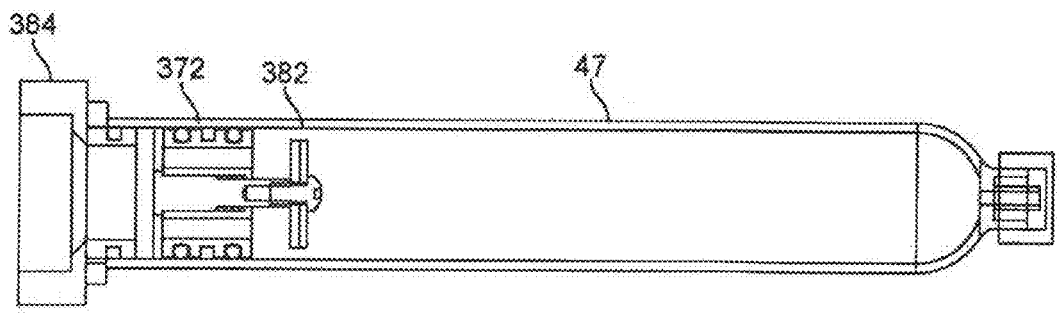
FIG. 45 shows a partial cross-sectional side view of a plunger and valve assembly coupled to a port adapter.

The plunger 372 may be activated when the cartridge 47 is engaged into the port adapters 384 which may be integrated into the base dock 370 for coupling to the cartridges 47. The design concept incorporates the use of a spring that may close the valve 382 in a rest state. When actuated, the spring may compress, opening the valve 372 for fill, as shown in the cross-sectional side view of FIG. 45. When released, the force of the spring may provide at least, e.g., 2.0 LbF, to overcome the vacuum draw in the injection device. Force of the vacuum draw to move the plunger 372 may be less than the force required to hold an air tight seal on the valve or leakage may occur.

Figure 46:
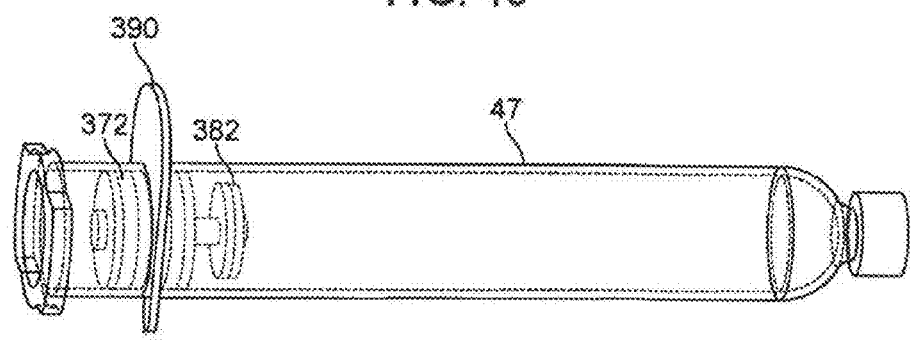
FIG. 46 shows a perspective view of another variation of a plunger and valve assembly integrated with a key for maintaining a position of the plunger.

A key 390 may be incorporated into the design to hold the plunger 372 in place while the cartridge 47 is engaged on to the adapter, as shown in the perspective view of FIG. 46. After fill, the key 390 may be removed and discarded to allow the plunger 372 to move.

Figure 47:
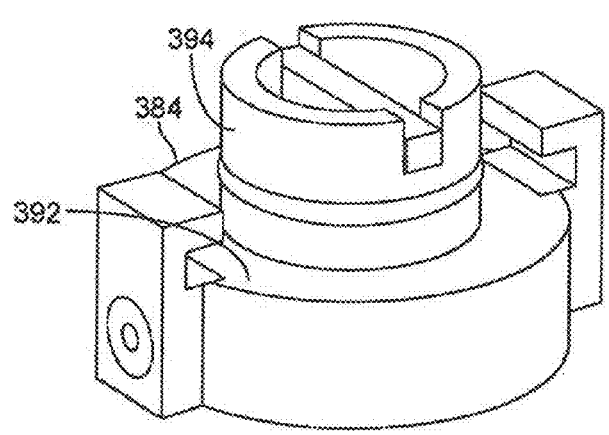
FIG. 47 shows a perspective view of an example of a port adapter.

A perspective view of a port adapter 384 is shown in FIG. 47. The variation illustrated may incorporate flanges 392 to hold the cartridge 47 against the base of the port 370 due to counter forces from the spring, which may pushes the cartridge 47 off the adapter 384. A static O-ring 394 may be incorporated to provide a vacuum seal during fat fill. The bar may push the valve open when engaged.

Figure 48A:
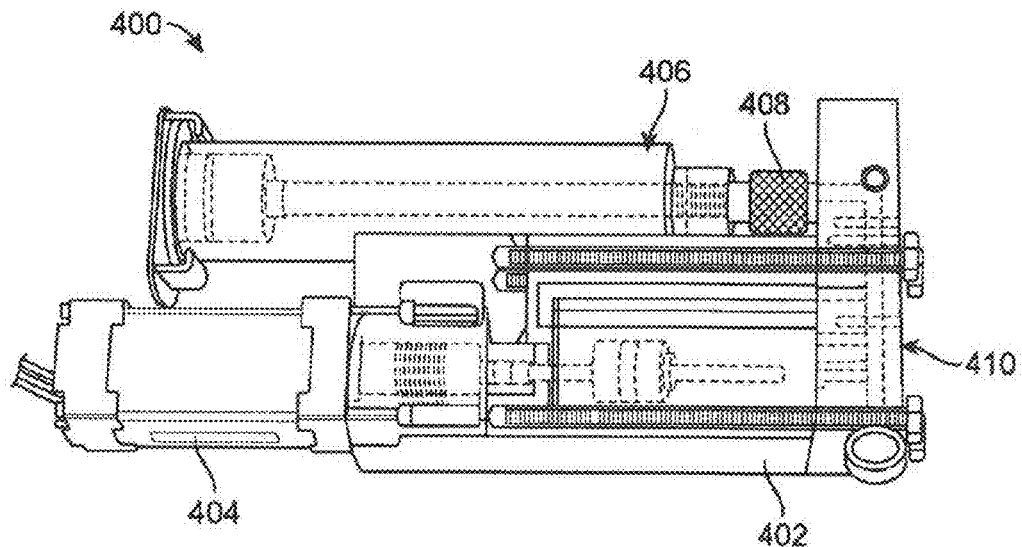
FIGS. 48A and 48B show respective side and schematic views of an example of a reversible pump assembly which may be integrated into any of the handle variations described herein.
Figure 48B:
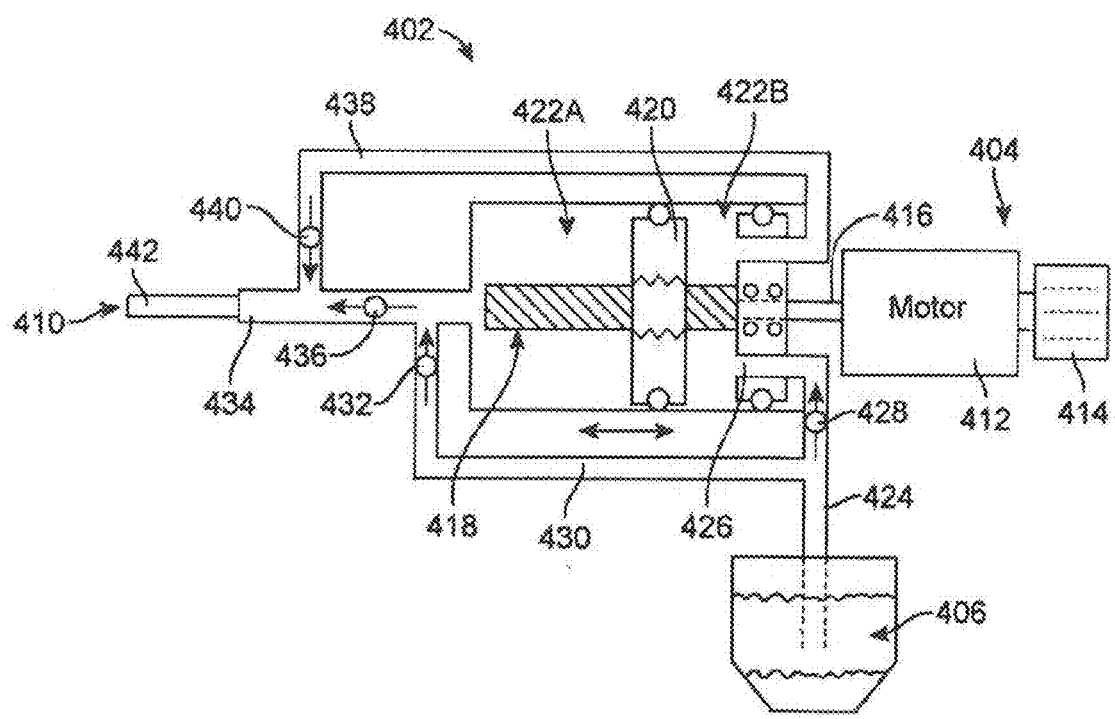

An example of a reversible pump assembly 400 which may be integrated into any of the handle variations described herein is shown in the side and schematic side views of FIGS. 48A and 48B. The pump assembly 400 shown may be integrated into any of the handle assemblies for use with the detachable harvesting and/or injection cannula to provide for continuous and uninterrupted withdrawal of tissue from the body for harvesting or for continuous infusion of tissue for injection, as described above. In either harvesting or injection, the vacuum pressure or injection pressure may be generated directly within the handle by the pump assembly 400 rather than relying upon a pumping mechanism separated from the handle.

Moreover, because the pump assembly 400 both aspirates and dispenses the tissue simultaneously, the pump 400 makes it possible to continually deliver the tissue with no wait time and shortens the overall procedure time.

The pump assembly 400 is shown as generally comprising a motor assembly 404 coupled to the pump 402. A detachable reservoir 406, e.g., cartridge 47, may be removably coupled via connection 408 to the pump 402. The pump 402 may further define an opening 410 through which tissue may be harvested from the body and into the pump 402 or injected from the pump 402 and into the body.

As illustrated in detail schematic of FIG. 48B, the motor assembly 404 may have a motor 412, e.g., stepper motor, with an optional time relay or controller 414. The motor 412 may be rotatably attached, e.g., to a rotatable lead screw 418, via a sealed motor coupling 416 where the lead screw 418 is contained within a common chamber. A plunger 420 translatably positioned upon the lead screw 418 may separate the common chamber into a first chamber 422A and second chamber 422B which may both be variably sized depending upon the relative position of the plunger 420 relative to the motor 412. When the lead screw 418 is rotated in a first direction, the plunger 420 may be forced to translate in a first direction within the chamber and when the lead screw 418 is rotated in a second opposite direction, the plunger 420 may accordingly translate in a second direction within the chamber opposite to the first direction.

In the case of tissue injection into the body, the detachable reservoir 406 having a volume of harvested tissue for injection may be removably coupled to a fluid channel 424. Fluid channel 424 may be fluidly coupled to the second chamber 422B via opening 426 and to fluid channel 434 which is in communication with opening 410. A valve 428, e.g., one-way valve, located along fluid channel 424 may allow for the uni-directional flow of tissue into second chamber 422B and a valve 432, e.g., one-way valve, located along fluid channel 430 coupling the reservoir 406 to fluid channel 434 may similarly allow for the uni-directional flow of tissue into and through fluid channel 434. A valve 436, e.g., one-way valve, positioned along fluid channel 434 may allow for the uni-direction flow of tissue from the first chamber 422A into and through fluid channel 434 and out of cannula 442. A fluid channel 438 fluidly connecting second chamber 422B to fluid channel 434 may also have a valve 440, e.g., one-way valve, which allows for the uni-directional flow of tissue from second chamber 422B into and through fluid channel 434.

In use, when the reservoir 406 is initially attached to the fluid channel 424, motor 412 may be actuated to urge the plunger 420 in a first direction, e.g., distally relative to the motor 412. As the plunger 420 moves along the first direction, a vacuum pressure generated within second chamber 422B may draw the tissue from reservoir 406 through channel 424 and through valve 428 and into second chamber 422B. Once the plunger 420 has been moved to a distal position along the lead screw 418, the motor 412 may be reversed to turn the lead screw 418 in a second opposite direction to force the plunger 420 to move in a second opposite direction proximally towards the motor 412. The reversed motion of the plunger 420 may generate a vacuum pressure within first chamber 422A to then draw the tissue from reservoir 406 through channel 430 and valve 432 and into first chamber 422A. As the tissue is drawn into first chamber 422A, the volume of tissue contained within second chamber 422B may be forced into channel 438 and through valve 440 and into channel 434 and out of the cannula 442 for injection into the body. The one-way valve 428 may close to prevent the reintroduction of tissue from second chamber 422B back into reservoir 406 and one-way valve 436 may likewise close to prevent the tissue passed through channel 438 from being drawn back into first chamber 422A.

As the plunger 420 reaches the end of its stroke, its direction may again be reversed to then urge the drawn volume of tissue within first chamber 422A through valve 436 and through cannula 442 and into the body while valve 432 and 440 may close to prevent the reintroduction of the tissue back into the reservoir 406. This process may be repeated in a continuous manner such that the tissue from reservoir 406 may be injected into the body in a continuous and uninterrupted flow regardless of which direction the plunger 420 is moved. Alternatively, the valves may be reversed in direction to provide for harvesting of the tissue from the body through cannula 442 (harvesting cannula) and into pump 402 for collection in reservoir 406 also in a continuous and uninterrupted manner.

Figure 49:
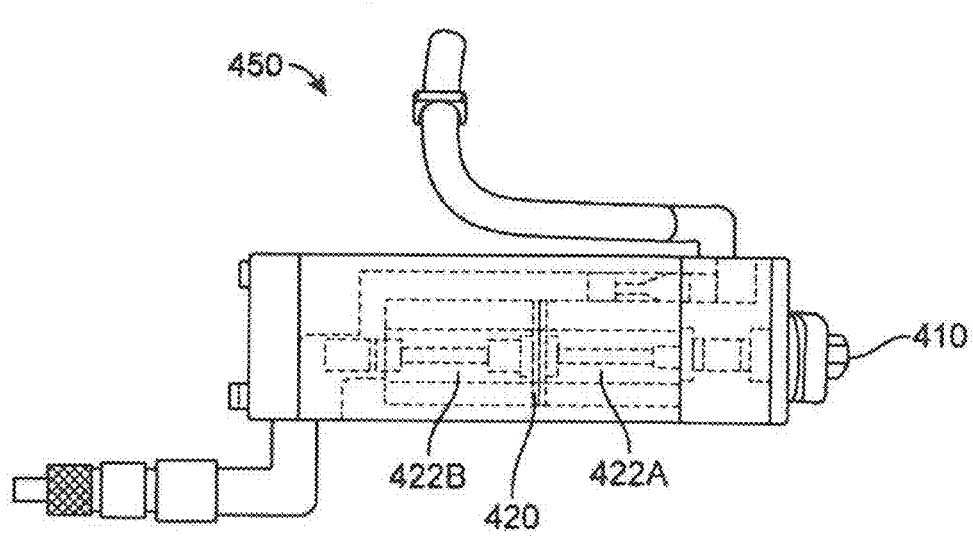
FIG. 49 shows a side view of another variation of the reversible pump assembly.

FIG. 49 shows a side view of another variation of the continuous pump assembly 450. As shown, the first and second chambers 422A, 422B may be seen separated by the translatable plunger 420. In this example, the reservoir is detached and may be coupled via a separate channel, as shown.

To ensure a predictable amount of material is dispensed with each stroke, the total travel of the plunger 420 may be sensed. One method is to use feedback from an encoder or controller, e.g., controller 414, attached to the drive motor 412. Another method to assess the position of piston 420 is to monitor the current required to drive the piston 420.

Figure 50:
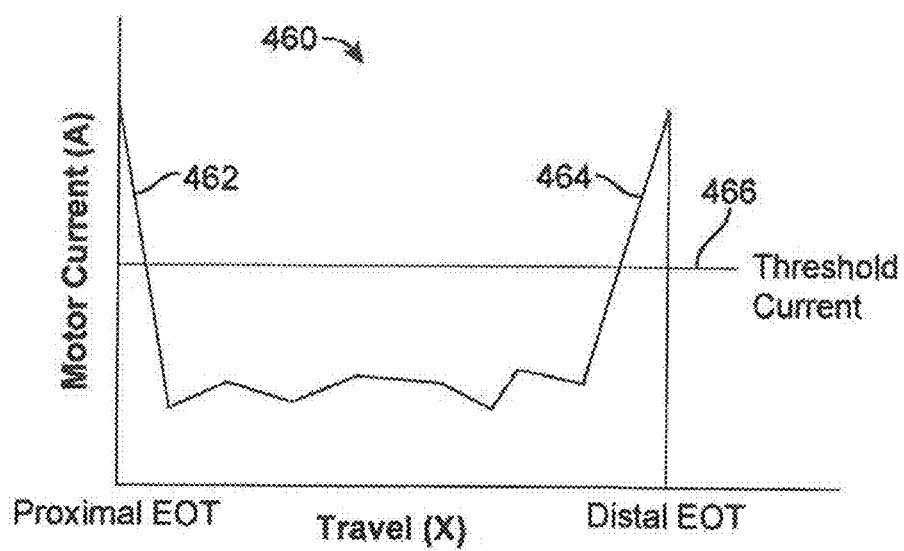
FIG. 50 shows a graph of the travel distance of the piston relative to the current drawn by the motor.

As shown in the exemplary graph of FIG. 50, the motor current may be graphed against a travel distance of the piston 420 within the chambers. As the piston travels between a proximal and distal end-of-travel (EOT) within the chamber, the current to the motor 412 changes with piston position. The signal moves up and down with changes in the power required to move the piston 420. For example, the current signal may increase when a large sample moves through the system and may drop when a more fluid sample moves through the system. However, when the piston 420 reaches the EOT, the piston 420 stops moving and the motor 412 draws more current to try and overcome the stalled piston 420. An internal electrical circuit may detect when that current exceeds a threshold current 466 indicating that the piston 420 has reached EOT and reverse the direction of the motor 412. The process repeats when the current threshold 466 is exceeded when the piston 420 reaches EOT at the opposite end of the chamber.

Figure 51A:
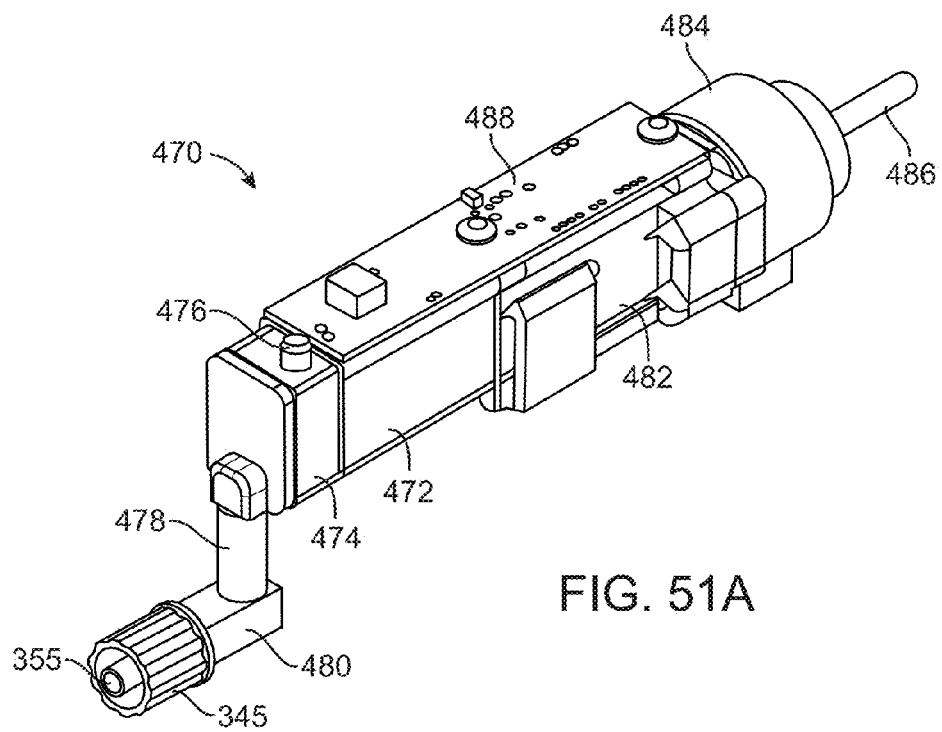
FIG. 51A shows a perspective view of yet another variation of a continuous pump assembly removed from the handle for clarity.

FIG. 51A shows a perspective view of yet another variation of a continuous pump assembly 470 removed from the handle for clarity. In this variation, the pump assembly 470 may incorporate a sensing and aliquot metering assembly within a proximal body 482 of the assembly, as described in further detail below. The main chamber 472 positioned distal to the proximal body 482 may contain the variable first chamber 490A and second chamber 490B with a translatable plunger 492 positioned to slide therethrough. A distal body 474 may be attached distal to the main chamber 472 and may integrate a port 476 for attachment to a channel in fluid communication with the cartridge 47. The fat tissue held within the cartridge 47 may flow into the port 476, through distal body 474, and into and through the main chamber 472 (as previously described) for passage through angled channel 478, luer block 480, and through lumen 355 for introduction into the body via the cannula 334.

Motor 484 may be positioned at a proximal end of the pump assembly 470 and may have a linear drive shaft 486 positioned through the motor 484 for translation through the assembly 470 to actuate the plunger 492. A linear position sensor circuit assembly 488 having a microprocessor and/or programmable logic device (such as a FPGA—fully programmable gate array) platform may be positioned along the pump assembly 470 and may further include sensor assemblies for detecting and/or controlling a position of the plunger relative to the chamber 472.

Figures 51B, 51C:
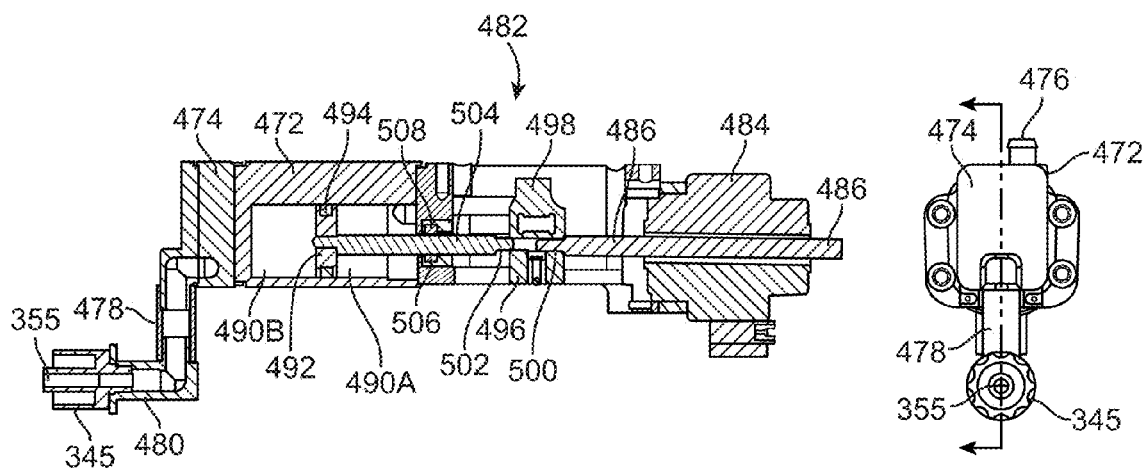
FIGS. 51B and 51C show cross-sectional side and end views, respectively, of the pump assembly with the circuit assembly removed for clarity.

FIGS. 51B and 51C show cross-sectional side and end views, respectively, of the pump assembly 470 with the circuit assembly 488 removed for clarity. As illustrated, motor 484 may have linear drive shaft 486 positioned to pass through the motor 484 such that drive shaft 486 may be translated linearly through the pump assembly 470 without rotating about its longitudinal axis via, e.g., an internal member such as a nut which may rotate within the motor 484 to translate the drive shaft 486 rather than rotating it. Linear translation of the drive shaft 486 rather than rotation of the shaft 486 may prevent any debris such as septae, which may be present in the fat tissue being pumped through main chamber 472, from wrapping or winding around the drive shaft 486 as it passes through main chamber 472. Accumulation of debris about the drive shaft 486 may inhibit or prevent further movement of the drive shaft 486 and reduce the pumping efficiency.

With the drive shaft 486 extending through motor 484, the distal end of the shaft 486 may be coupled to an interrupter assembly 496 through a drive shaft receiving channel 500. The interrupter assembly 496 may be configured as a slidable member which has a thin flag or projection 498 extending from the member with a drive shaft receiving channel 500 and plunger shaft receiving channel 502 defined collinearly through the assembly 496 and parallel with the flag or projection 498. With the distal end of the drive shaft 496 positioned within the receiving channel 500, a proximal end of the plunger shaft 504 may be positioned within the plunger shaft receiving channel 502 collinearly aligned and adjacent. As the drive shaft 486 translates through the motor 484 and proximal body 482, the translational force may be transmitted via the interrupter assembly 496 to the plunger shaft 504 and down to the plunger 492 which may translate through the main chamber 472 to effectuate tissue injection. The plunger 492 may incorporate a seal 494 around its periphery as well as a seal 506 along the plunger shaft 504 along a pump barrier 508 between the main chamber 472 and proximal body 482 to prevent or inhibit fluid from escaping from or between the chambers 490A, 490B.

Prior to and during fat tissue injection through the pump assembly 470, the circuit assembly 488 may initiate the device as well as control the aliquot delivery from the assembly 470. An example is shown in the end view of FIG. 52A and perspective cross-sectional side views of FIGS. 52B to 52D which show the pump assembly 470 with the handle housing removed for clarity. As illustrated in FIG. 52B, upon attaching the cartridge to the handle assembly and turning the assembly on, the circuit assembly 488 may start the motor 484 to position the plunger 492 in a prime position where the plunger 492 is positioned proximally within the main chamber 472 and where the flag or projection 498 or interrupter assembly 496 is correspondingly positioned proximally within the proximal body 482 such that the flag or projection 498 triggers or actuates a proximal sensor 510.

FIG. 52C illustrates an example of how the plunger 492 may be translated through the main chamber 472 until its maximum travel distance has been reached where first chamber 490A is expanded to receive fat tissue and the corresponding second chamber 490B is compressed to inject the tissue contained within. The flag or projection 498 is correspondingly translated through proximal body 492 until it triggers the distal sensor 512 which may provide an indication to circuit assembly 488 that the maximum travel position has been reached.

FIG. 52D illustrates an example of the home position of plunger 492 where both chambers 490A, 490B have been evacuated of any extraneous air or fluids and the device is ready for further actuation. The proximal edge of the flag or projection 498 may just interrupt the proximal sensor 510 to provide an indication to the circuit assembly 488 that the pump assembly 470 is in the home position and ready for further tissue injection.

Figure 53A:
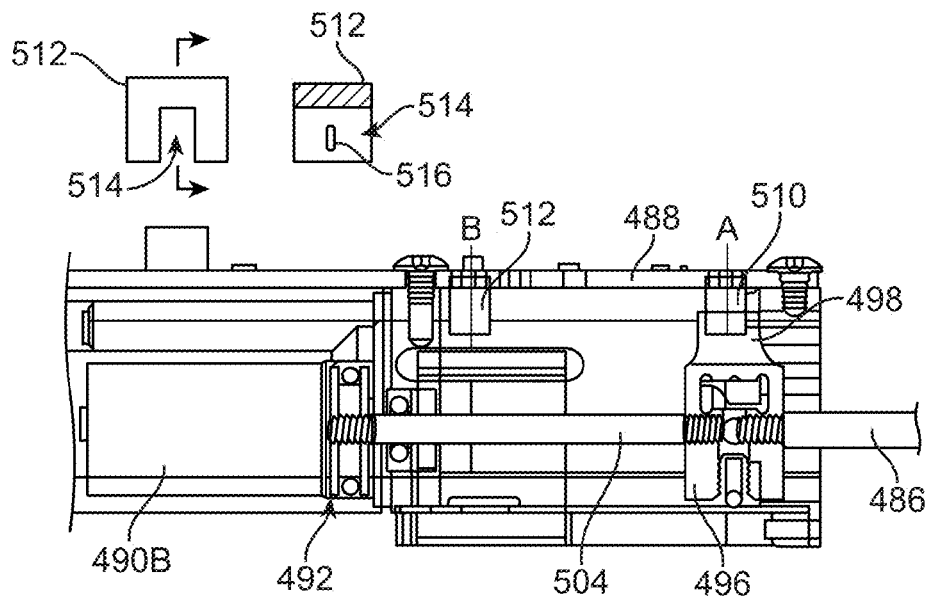
FIGS. 53A to 53C show detailed side views of the proximal body to illustrate corresponding use of the proximal and distal sensors within the pump assembly.
Figure 53B:
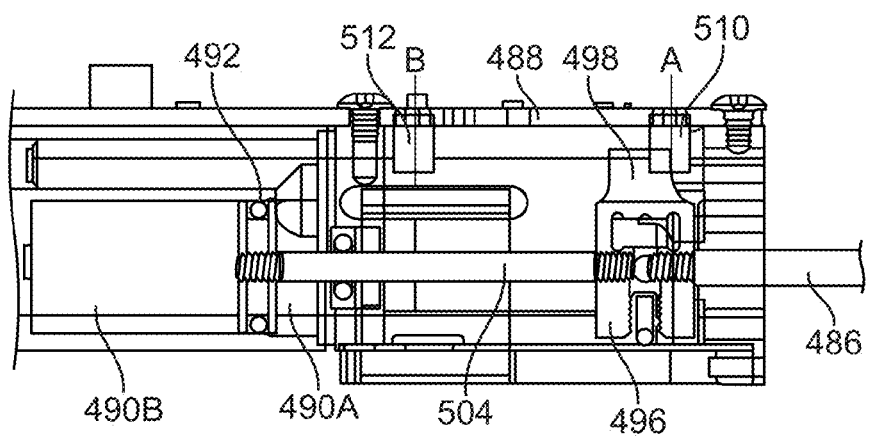
Figure 53C:
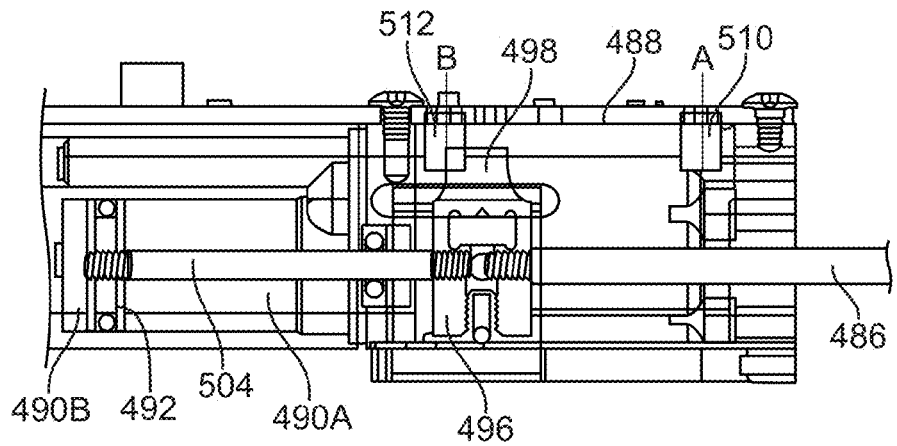

FIGS. 53A to 53C illustrate detailed side views of the proximal body 482 to illustrate corresponding use of the proximal 510 and distal sensors 512. As shown in FIG. 53A, the pump assembly has been initially actuated to prime the main chamber 472 by positioning the plunger 492 in its proximal position where the second chamber 490B is maximized and the flag or projection 498 is positioned to actuate proximal sensor 510. A detail front and partial cross-sectional side view is further shown of distal sensor 512 to illustrate one variation of the sensor which may be used. The proximal sensor 510 and/or distal sensor 512 may be configured as a yoke-shaped structure which defines a flag receiving channel 514 through which the flag or projection 498 may pass. An infrared signal receiver/emitter 516 may be positioned along one member for passing an infrared beam between the members. Because the interrupter assembly 496 may be fabricated from an opaque material (e.g., ABS plastic, metal, etc.), once the flag or projection 498 passes the receiver/emitter 516, the beam may be interrupted and indicate to the circuit assembly 488 that the interrupter assembly 496 is in proximity to the proximal 510 or distal sensor 512.

Although the proximal 510 or distal sensor 512 are illustrated as infrared sensors, any number of alternative sensors may be utilized with the devices described herein. For example, laser sensors, electrical contacts, or any other suitable sensing mechanisms may be utilized.

Once the assembly 470 has been primed and powered, the trigger 349 may be initially actuated to actuate the motor 484 to drive the shaft 486 to move plunger 492 to a home position where the circuit assembly 488 may register a position of the plunger at zero. The drive shaft 486 may move the flag or projection 498 distally until the proximal edge of the flag 498 just interrupts the proximal sensor 510, as shown in FIG. 53B. The plunger 492 may be correspondingly moved to its home position within the main chamber 472 ready to initiate tissue transfer through the first and second chambers 490A, 490B. As the trigger 349 is further actuated, the motor 484 may drive the drive shaft 486 distally to move interrupter assembly 496 and plunger 492 through the pump assembly 470 until the flag or projection 498 triggers the distal sensor 512 which acts as a limiting trigger, as shown in FIG. 53C. Upon detection of the flag or projection 498 in its distal position, the circuit assembly 488 may reverse the direction of the drive shaft 486 and plunger 492 to inject the tissue contained within the first chamber 490A and to re-fill the tissue in second chamber 490B, as described above.

Figure 54:
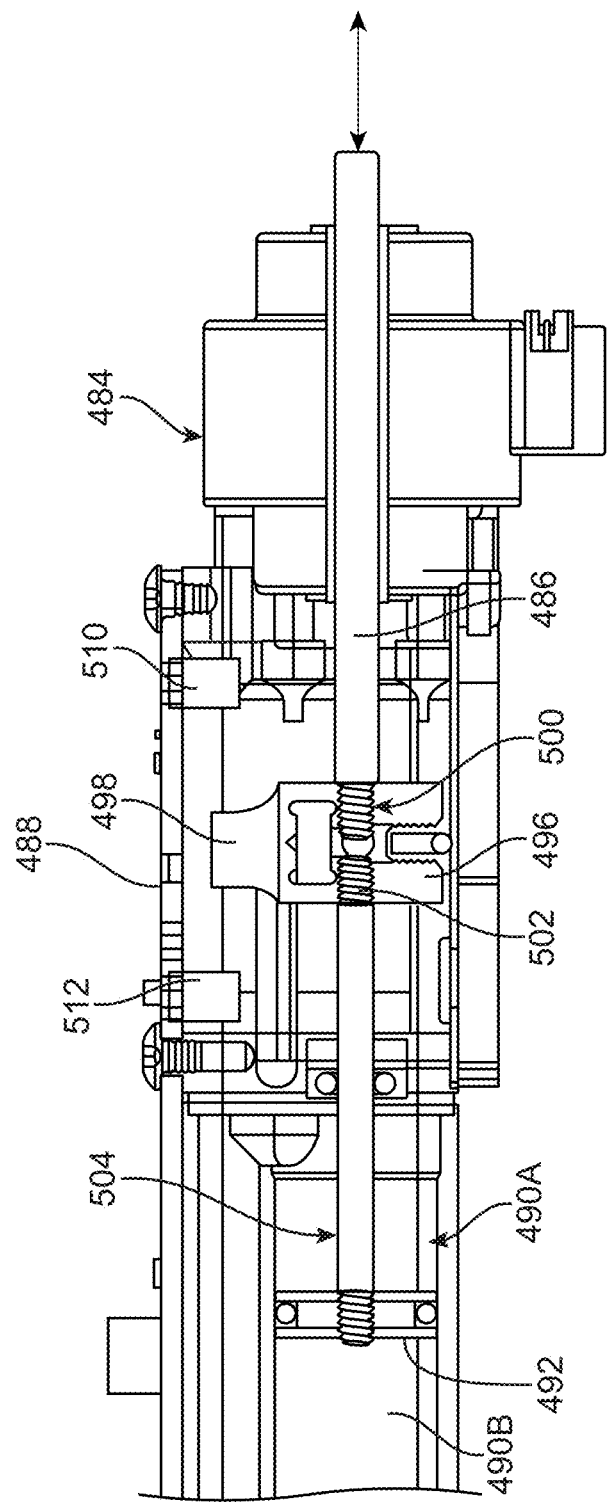
FIG. 54 shows a partial cross-sectional side view of the pump assembly and details of the interrupter assembly.

Aside from the transfer of linear motion from the drive shaft 486 to the plunger shaft 504 and plunger 492, the interrupter assembly 496 may further function as a thermal insulator to prevent or inhibit heat transfer from the motor 484 to the tissue contained within the first and second chambers 490& 490B, as shown in the partial cross-sectional side view of FIG. 54. Because the motor 484 can potentially reach temperatures of around 120° C., cell death can result from exposure to temperatures greater than 37° C. The heat generated by the motor 484 (e.g., 60%-80%) can conducted into and through the drive shaft 486. However, because of the separation between the drive shaft 486 and plunger shaft 504 and the minimal surface area contact between the shaft ends and the interrupter assembly 496, which may be made from a thermally insulating material such as ABS plastic, any heat conduction from the motor 484 via the drive shaft 486 and to the plunger shaft 504 is minimal thereby preventing cell death from heat exposure.

Figure 55A:
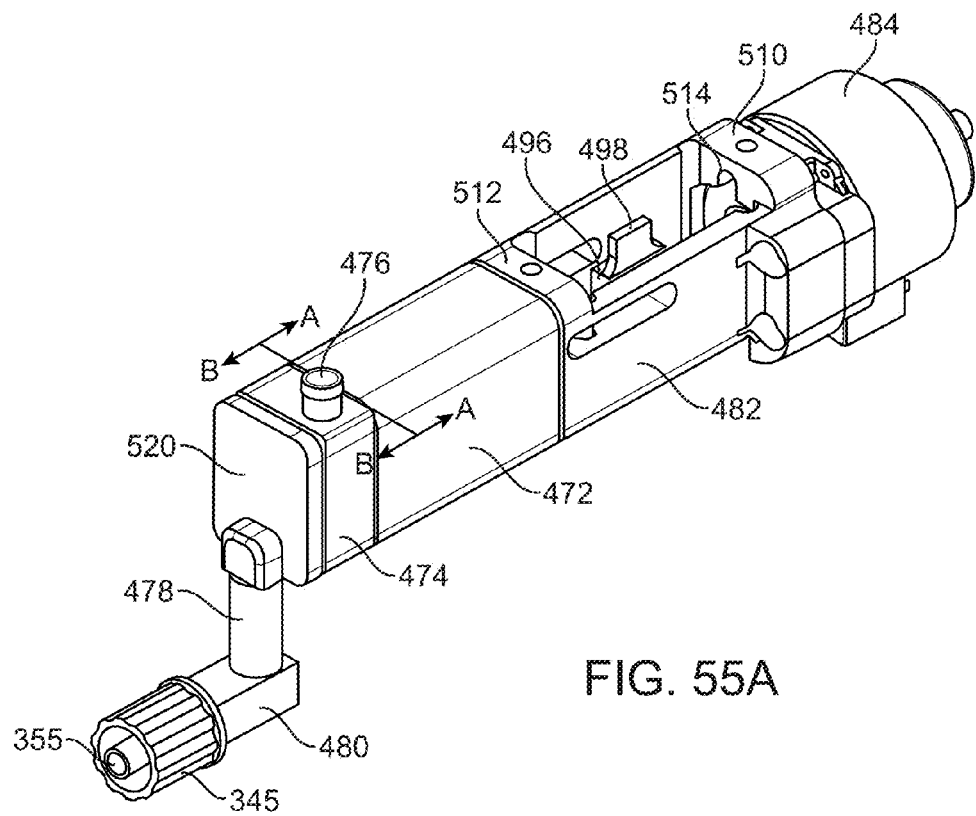
FIG. 55A shows another perspective view of the pump assembly with the circuit assembly removed for clarity.
Figure 55B:
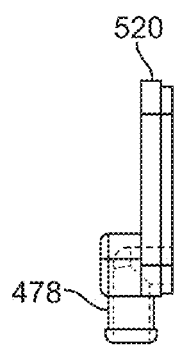
FIGS. 55B to 55D show side and end views of the components of the main chamber and distal cap.
Figure 55C:
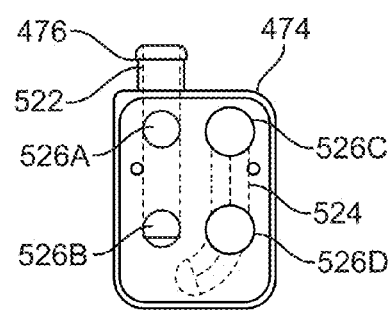
Figure 55D:
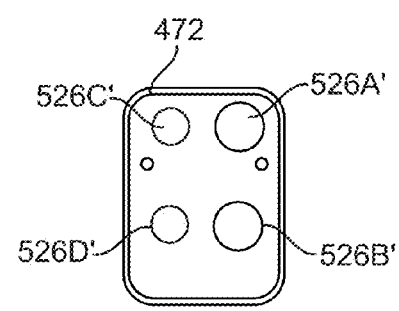

FIG. 55A shows another perspective view of the pump assembly 470 with the circuit assembly 488 removed for clarity. As shown, the interrupter assembly 496 with the flag or projection 498 may be seen slidably positioned between the proximal sensor 510 and distal sensor 512. FIG. 55B also shows a side view of distal cap 520 and angled channel 478 which may cover the distal end of distal body 474. An end view of the distal body 474 is also shown in FIG. 55C which illustrates channel 522, 524 and their respective lumen openings 526A, 526B, 526C, 526D in fluid communication with port 476. Likewise, FIG. 55D shows an end view of the main chamber 472 with corresponding openings 526A', 526B', 526C', 526D' for fluid coupling with the lumen openings 526A, 526B, 526C, 526D. For all internal channels and ports, the respective diameters may range anywhere from, e.g., 0.050 in to 0.250 in, in this variation although other variations may include variable sized lumens.

However, when sizing the lengths and diameters of the ports and lumens (and surface finishes) as well as their positioning relative to one another, there are several factors for consideration in ensuring that the adipose tissue remains viable and survives during pumping and implantation. For instance, such factors become relevant as they may directly impact the flow and shear stresses imparted upon the adipose tissue and ultimately determine whether the tissue survives the implantation process.

A first consideration is the media, i.e., the pumped media may be comprised of adipose, connective tissue and possibly additives (mixed in prior to injection). The ports, lumens, and valves may be sized and positioned to pass the colloid.

A second consideration is that the piston 492 may move at any number of speeds determined by the motor 484. The ports, lumens and valves may be sized and positioned (as described above) to accommodate the pumping speed to ensure head losses do not lead to over pressurization or excessive sheer stress on the media. That is, the port, lumen, and valves dimensions described herein are particular to the delivery and passage of the adipose tissue and are accordingly sized to ensure that excessive pressure is minimized on the tissue and hence to ensure tissue viability.

A third consideration is for valves that operate on pressure differentials, such as flapper or duck bill valves, where the orientation and positioning of these valves are essential to ensure that components such as septae pass through the valves without interfering with the valve or the reciprocating pressures that open, close and seal the flow paths. More specifically, flapper valves hinge from a position of the lowest pressure (lowest flow) in the flow path to ensure septae pass the through the valve. Orienting the flapper improperly allows the septae to catch on the flapper such that the septae may work its way toward the hinge until the hinge is bound and the flapper fails.

Figure 55E:
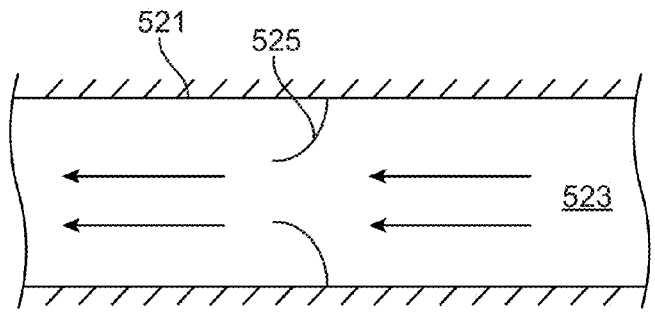
FIGS. 55E and 55F show side and end views of a representative duck bill-type valve oriented to prevent or inhibit tissue from binding against the valve.
Figure 55F:
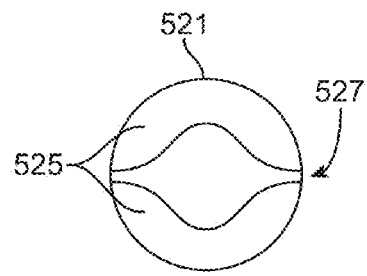

One example is illustrated in the side and end view of FIGS. 55E and 55F which show a representative duck bill-type valve 525 positioned within lumen 521 with adipose tissue 523 flowing through. Such valves 525 may be located throughout the pumping assembly. The valve 525 may be seen in FIG. 55F where the valve leaflets are oriented to open in an up-down orientation relative to the flow path of tissue 523. Because the areas where the valve leaflets converge 527 represent pinching regions where the tissue 523 may accumulate and bind, orienting the valve 525 to maintain the leaflets in the up-down orientation ensures that the converging areas 527 are located along the sides where the tissue 523 is less likely to bind. If the converging areas 527 were rotated, e.g., 90 degrees, such that the valve leaflets were oriented left-right relative to the tissue flow, the tissue 523 may be more likely to accumulate and bind around the areas 527 thus fouling the valve 525.

Figure 55G:
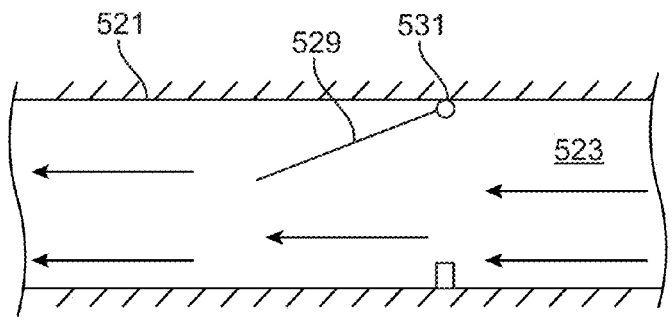
FIGS. 55G to 55I show side and end views of a representative flapper-type valve oriented to prevent or inhibit tissue from binding against the valve.
Figure 55H:
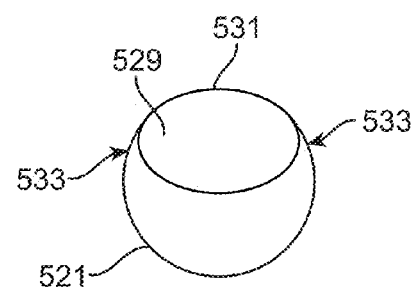

Another example is shown in the side and end views of FIGS. 55G and 55H which illustrate a representative flapper-type valve 529 which may rotate about hinge 531. Similarly, valve 529, as it rotates to open/close, may have converging areas 533 which may pinch the tissue as it flows and where the tissue may likely accumulate and bind. Having the converging areas 533 oriented along the left-right of the valve 529 may help to ensure that the tissue 523 is less likely to bind around the valve 529. Similarly, if the converging areas 533 were rotated, e.g., 90 degrees, such that the hinge 531 were oriented up-down, the tissue 523 may be more likely to bind and foul the valve 529.

Figure 55I:
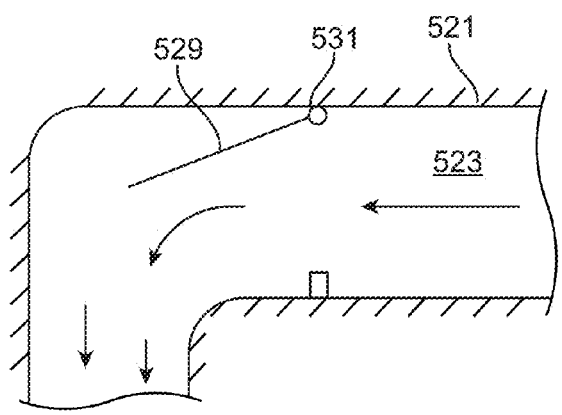

FIG. 55I shows a side view of an example where having the valve 529 oriented in the manner shown and described may be particularly helpful in reducing or inhibiting tissue from binding to or around the valve 529. In this example, the flapper valve 529 may be hinged 531 along the top relative to the tissue flow particularly where the lumen 521 may bend or curve upstream or downstream in proximity to the valve 529. As illustrated, valve 529 may be hinged 531 to rotate upwardly relative to the flow just proximal or upstream to where lumen 521 bends or curves, such as in a 90 degree bend. In other variations, valve 529 may be positioned distal to the bend as well in the same manner as shown and described. Positioning the hinge 531 opposite to the location shown and described (i.e., 180 degrees from the position shown) may appear to ensure a secure closure of the valve 529 in sealing properly by taking advantage of a relatively large reciprocating pressure differential. However, positioning hinge 531 in such a manner may actually hinder proper closure of the valve 529 due to the difficulties in accumulating tissue around the converging areas and may actually prevent adequate sealing of the valve 529.

A fourth consideration relates to form factor where once the ports, lumens and valves are properly sized and positioned, the form factor is desirably small enough to fit within the confines of a hand-held device that keeps wasted media to a minimum. That is, the port, lumen, and valve positioning as described herein is sized and located to ensure that the assembly is optimally sized for configuring into the hand-held assembly shown, for instance, in FIGS. 36A to 36J.

Moreover, while these considerations are generally for adipose tissue and its particular composition, they may also apply to other materials such as colloids where the tissue is comprised of autologous tissue and one or more supplements added to improve the graft's performance.

As previously described, while the flag or projection 498 acts as a linear encoder, the assembly may further incorporate a linear position sensor 530, e.g., FSLR position sensing resistor, positioned along the proximal body. Interrupter assembly 496 may incorporate a plunger 532, e.g., ball plunger, which maintains a force upon the linear position sensor 530 as the interrupter assembly 496 traverses through the proximal body, as shown in the partial cross-sectional side views of FIGS. 56A and 56B. The position of the plunger 532 upon the linear position sensor 530 may provide the position of the interrupter assembly 496 and hence the plunger position within the main chamber 472 at all times to the circuit assembly 488.

Figure 56A:
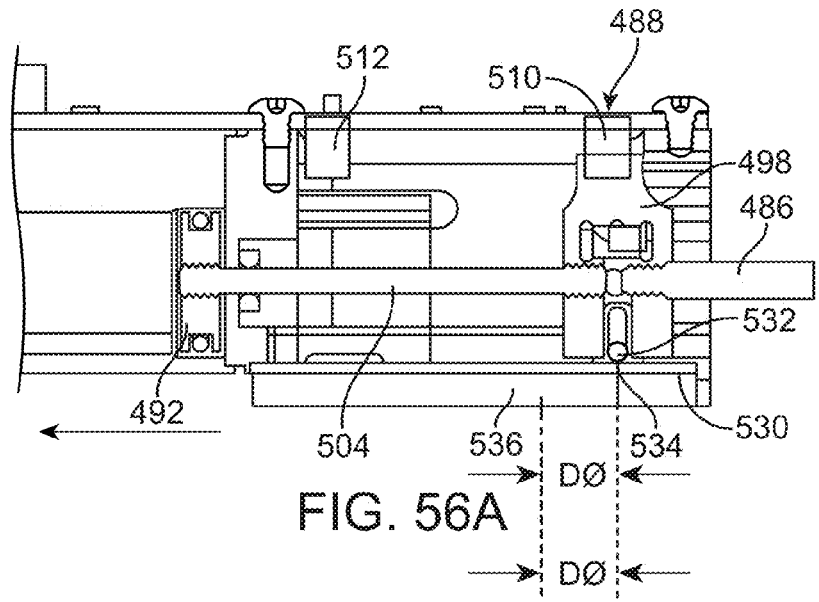
FIGS. 56A to 56C illustrate how the plunger may be initiated in a primed position and home position and subsequently stepped to deliver a controlled volume of aliquots.
Figure 56B:
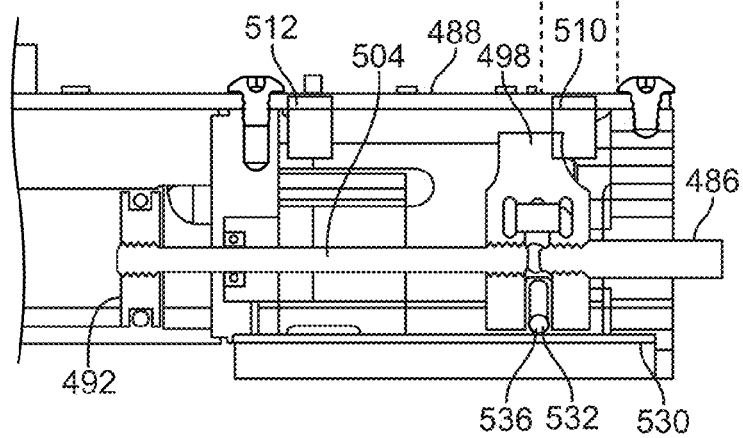
Figure 56C:
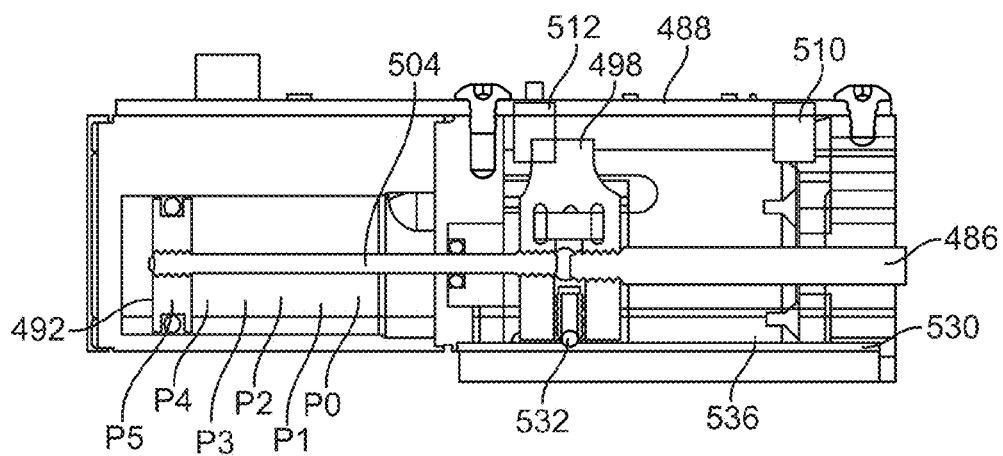

As shown in FIG. 56A, the initial prime position 534 may correspond with 0.0 V as a starting condition and the home position may correspond with 0.75 V as output by the linear position sensor 530 and as registered by the processor on circuit assembly 488. Once the pump assembly 470 is turned on, primed, and moved into the home position 536, i.e., a distance D0 from the initial prime position 534 to the home position 536, the circuit assembly 488 may begin to measure and compare voltages at each subsequent position along the linear position sensor 530 and compare the relative differences. For instance, the plunger 492 may be programmed to move in a stepped manner such that the plunger 492 moves from its home position P0 to any number of subsequent stepped position P1, P2, P3, P4, P5 corresponding to each volume pumped from the assembly 470, as shown in FIG. 56C. If those measured differences remain consistent, the pump is operating correctly. However, if the differences begin to read differently, e.g., relatively lower, then this may be an indication that the pump is malfunctioning or this may indicate the presence of a clog in the pump.

As the plunger 492 translates, it may be translate at a rate sufficient to pump the tissue anywhere between, e.g., 0.1 to 2.5 cc per second, without damaging the tissue. Moreover, the pumping system may maintain an internal pressure between, e.g., 15 in Hg (vacuum) and 51 in Hg (pressure).

The circuit assembly 488 may constantly check for clogs and whether they have been cleared. Each time an aliquot is dispensed and the piston 492 stops (e.g., at subsequent stepped position P1, P2, P3, P4, P5, etc.) an associated piston position value (count) may be stored in the circuit assembly 488 and compared with previous aliquot counts. Under normal operation, the count change is repeatable within some tolerance (the tolerance accounts for any system hysteresis or manufacturing/component variation). When a clog develops, pressure builds and the piston 492 may not move as far as it should, the resulting count falls out of the tolerance range and a clog is indicated. When a clog clears (either on its own or with outside intervention such as by replacing the cannula), the counts fall back within normal tolerances and the clog flag clears.

Clog detection becomes more complex with the pump's capability of delivering two different sized aliquot as well as a platform that can be programmed to provide a range of predetermined aliquot sizes to select from. Consequently, the clog detection scheme may also be equally flexible.

The circuit assembly 488 may provide this flexibility by comparing the counts of consecutively stored position counts and programmed parameters to detect clogs (and clears). Clogs may be flagged if an out of tolerance condition has occurred within any of the previous aliquot deliveries, e.g., 1 to last 8 aliquots. An all-clear signal may be flagged in a similar manner and has priority to a flagged clog. For example, assuming the circuit assembly 488 is programmed to look back N=6 aliquots for clogs and N=2 for cleared, every time the piston 492 stops, the count may be recorded and circuit assembly 488 may examine the difference between the current count and the previous 6 aliquot counts. If the count comparison is out of range, a clog is flagged. Next the count comparison is made 2 aliquot counts back and if it is within the tolerance range, then an all-clear signal is provided and any previous clog flag may be cleared and no clog is indicated. If the difference is out of range and the clog flag is set, a clog is indicated.

Since aliquot parameters are stored in the device for the pre-programmed aliquot sizes, when the user selects a different aliquot size, the new parameters may be used to evaluate clog/clear conditions for the new size without the need to restart or home the device.

In the event of a clog or obstruction in the pump, a visual or audible indicator or alarm may alert the user. For instance, an LED board 550 located along luer block 480, as shown below in FIG. 58A, may illuminate. Additionally, if the clog appears to have cleared (either on its own or manually) and the voltage differences return to a consistent level, then the indicator or alarm may shut itself off.

The motor 484 can be controlled by circuit assembly 488 to be driven a defined amount of steps that equate to the desired dispersement volume of tissue. The number of aliquots that can be pumped without changing the direction of the motor 484 may be defined by the aliquot volume and the number of steps needed. For instance, if one aliquot of a 0.5 cc volume of tissue requires 100 steps of the motor 484 and plunger 492 for dispensing from the pump and the total number of steps available in a single pumping direction is set at 450, then the processor on the circuit assembly 488 may determine that the pump assembly 470 can produce four 0.5 cc aliquots before having to switch motor direction. Avoiding directional changes of the pump mid-delivery of an aliquot may help to avoid any directional-change related inconsistencies in volume size delivered. However, even in the motor 484 requires switching of its direction, the tissue volume dispensed may remain continuous and accurate during tissue injection.

Additionally, the circuit assembly 488 may be programmed to automatically advance the plunger 492 a pre-determined number of steps for metered aliquot delivery. For example, each time the actuation trigger 349 is depressed, the plunger 492 may advance in "small" or "large" steps until a pre-determined number of steps or pre-determined volume is delivered. By depressing the controller 357 once or twice or some pre-determined number of times, the circuit assembly 488 may be programmed to accept a relatively small or large aliquot delivery per step while the actuation trigger 349 remains depressed. For instance, the aliquot volume may range for delivery of 0.5 cc or 1.0 cc per step or smaller increments of 0.2 cc or 0.4 cc per step or any other increments so desired.

The circuit assembly 488 and microprocessor may be programmed to avoid mid-aliquot direction changes by utilizing a "look ahead" feature. When the pump is initially turned on and the piston 492 moves out of its prime position, the assembly 488 may remember the home position. Since the total cylinder stroke length is known by design, the assembly 488 "knows" where the piston 492 is relative to home as it moves back and forth through the cylinder during the pumping process. Before pumping the next aliquot, the assembly 488 "looks ahead" to see if there is enough travel to dispense a complete aliquot. If there is, the piston 492 may continue in its direction of travel. If there is not enough travel, the piston 492 may automatically reverse and starts pumping in the opposite direction.

While this approach addresses the majority of aliquots, there are three other alternative conditions. The first condition is the pre-programmed aliquot that is larger than can be delivered in a single stroke through the cylinder rendering the "look ahead" feature potentially inapplicable. For this case, a number of parameters may be added to account for any inconsistencies that may be related to a directional change. Specifically, the piston 492 may be over-driven by a predetermined amount (e.g., defined by unique variables for proximal and distal direction and for predetermined aliquot sizes) thereby delivering the added material lost during a directional change.

The second condition to address is when the actual piston location may loses sync with the known location which can happen when the stepper motor 484 slips such as when the pump clogs. In this case, the piston 492 will eventually reach the distal end of travel limit switch where the piston location is resynchronized and the end-of-travel parameters define how much farther the piston 492 must travel in the opposite direction to complete the aliquot.

The third condition addresses what happens if aliquot size is changed during the procedure. If the aliquot size is changed mid-procedure, the circuit assembly 488 may determine which way the piston 492 should move immediately after the change and whether it can accommodate the change or whether it will over-drive the piston displacement to ensure the desired aliquot size is delivered. In the event the piston 492 is not where it is expected, the end-of-travel limit switch resynchronizes the piston location with its home position to ensure all the aliquot sizes are consistent.

The volumes and steps described above are intended to be illustrative of the various parameters which may be adjusted by the user with the devices described herein. Hence, the number of steps per trigger actuation as well as the volume dispensed per step (aliquot volume), step rate, dwell time, etc., may be varied over any suitable range depending upon the desired application and volume to be dispensed. Moreover, stepped advancement of the plunger 492 as well as adjustment of the number of steps may be applied to any of the embodiments described herein.

Figure 57A:
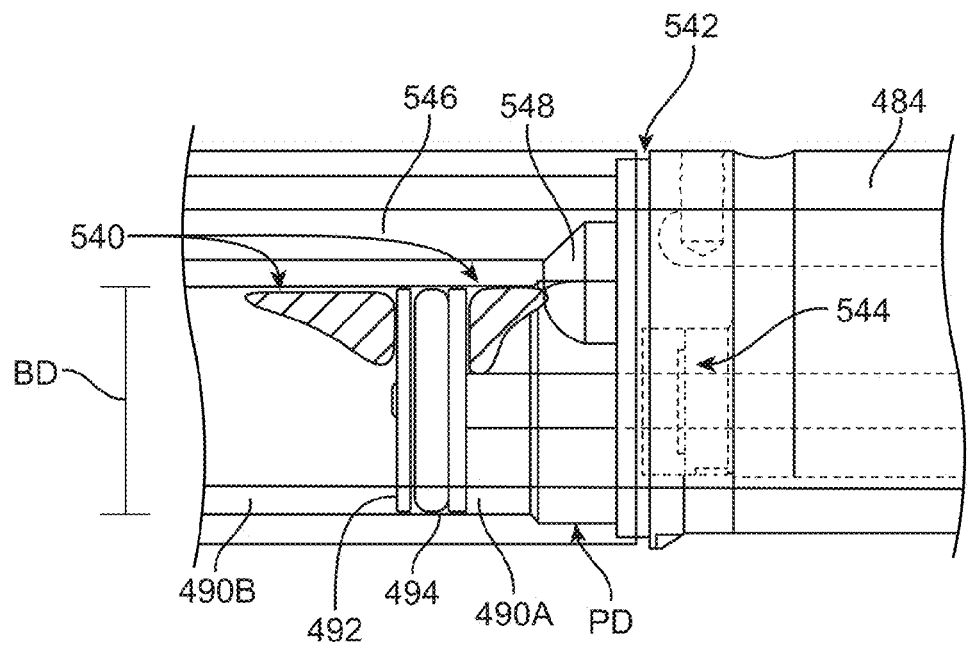
FIGS. 57A and 57B show detail side views of the enlarged priming bore diameter for clearing air or debris from the pump assembly.
Figure 57B:
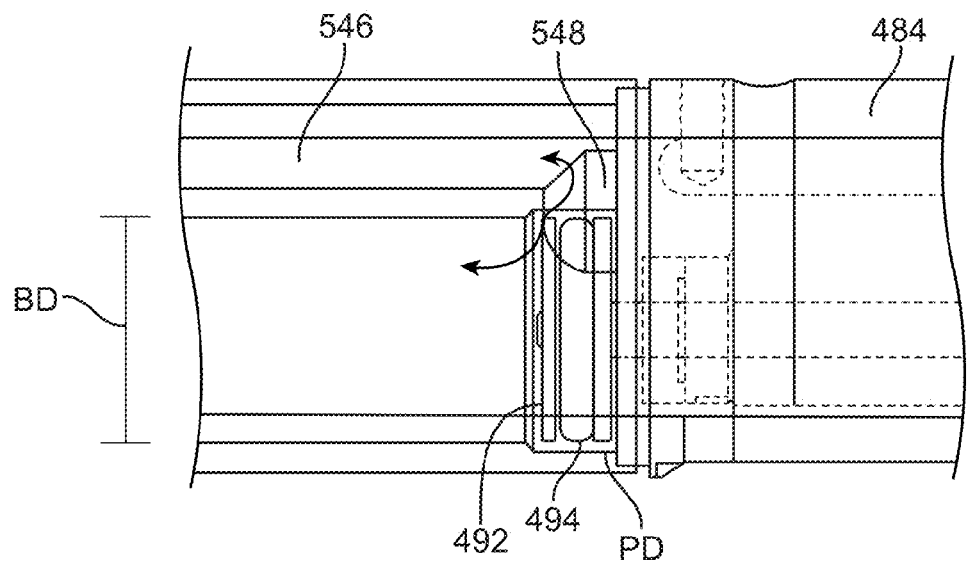

Aside from controlling advancement of the plunger 492, another feature which may be incorporated into any of the embodiments herein is shown in the detail side views of FIGS. 57A and 57B. When tissue is introduced into the chambers 490A, 490B entrapped air or debris 540 may accumulate within one or both chambers 490A, 490B particularly because of the circumferential seal 494 around plunger 492. To remove this air or debris 540, a proximal portion of the pumping chamber may be made to have a priming bore diameter PD, e.g., 0.520 in., which is larger than the bore diameter BD, e.g., 0.500 in., of the chambers 490A, 490B. The diameters are provided as examples of the amount of clearance which can be provided and the diameter differences and are not intended to be limiting.

The area around the priming bore diameter PD may be in fluid communication through port or opening 548 in fluid communication with fluid channel 546 through which the tissue within chamber 490A may be pumped through. The priming bore diameter PD may provide enough clearance for the seal 494 such that when plunger 492 is initially moved into its primed positioned (as described above) the air or debris 540 from one or both chambers 490A, 490B may escape through the port or opening 548, as shown in FIG. 57B, and avoid being injected into the patient body. Also shown are the bonded pump joint 542 and shaft seal 544.

Because sufficient clearance is provided around the seal 494 when positioned in its primed location within the priming bore diameter PD, the free lipids within the fat tissue are able to wick around the seal 494 and also provide lubrication to the seal 494 as it traverses through the main chamber 472. Hence, the pumping assembly may be provided to a user with the plunger 492 and seal 494 positioned in its primed location, as shown in FIG. 57B, which will prevent the seal 494 from taking a set if otherwise compressed. Additionally, because the fat tissue introduced into the system may act as the lubricant itself, the pumping system may be provided without any additional lubrication.

Yet another feature which may be incorporated into any of the variations described herein to the extent practicable is shown in the side and detailed perspective views of FIGS. 58A and 58B. As shown, the attachment of the cannula to the pumping assembly may also incorporate a feature which decouples or isolates any forces applied to the cannula from the rest of the pumping assembly. One variation is shown in the side view of FIG. 58A which illustrates the angled channel 478 and luer block 480. The cannula coupler 345 may connect to a cannula such that the forces applied to the cannula during attachment and use are decoupled from the main chamber but preserve the fluid communication through lumen 355. The angled channel 478, having a distal cap 558 attached thereto, and luer block 480 may be attached via attachments 552, 554, 556 (e.g., bonding, interference fit, etc.) and maintain a longitudinal axis of luer block 480 separated or off-set from a longitudinal axis of the main chamber.

As previously described, a visual or audible indicator or alarm such as LED board 550, may be attached proximal to the cannula coupler 345 and may light or flash as an indication that a clog may be present in the lumen 355 or cannula. Other variations of LED board 550 may be used in alternative examples.

As illustrated in the perspective view of FIG. 58B, luer block 480 may also be secured within the bottom portion of handle 566 to further prevent the transmission of forces placed upon the couple 345 from being relayed or imparted to the main chamber. The bottom portion of handle 566 may thus define side channels 560, 562 and a proximal stop 564 within which luer block 480 may rest. As shown in the illustrative end view of FIG. 58C, once luer block 480 is positioned within the channel, the contacting walls of the handle against the luer block 480 may prevent rotation of the block 480 in any of the rotational axes, i.e., X, Y, or Z axes. Moreover, once the top portion of handle 568 is placed upon the pump assembly and luer block 480, the luer block 480 and any forces imparted upon the cannula and luer block 480 itself may be prevented from further transmission.

Further examples and variations of the harvesting instrument as well as processing and guidance and also injection devices and methods are further described in the following description and figures, which is incorporated herein in its entirety.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of implanting tissue, comprising:
    inserting a cannula percutaneously into a targeted area;
    operating a pump including a pumping chamber to inject a plurality of aliquots of adipose tissue from a tissue reservoir through the cannula; and
    injecting the plurality of aliquots of adipose tissue from the tissue reservoir through the cannula into each tract while withdrawing the cannula along a tract;
    the injecting step comprising injecting a total of 100-1000 cc of adipose tissue into the targeted area from the reservoir;
    wherein the pumping chamber defines a bore diameter and a priming bore diameter, the bore diameter separating the priming bore diameter from the cannula, the priming bore diameter being disposed at a proximal portion of the pumping chamber, and the priming bore diameter being dimensioned greater than the bore diameter of the pumping chamber; and
    wherein the pumping chamber includes an opening formed in a wall of the pumping chamber at the priming bore diameter configured for ejection of air or debris from the pumping chamber.

2. The method of claim 1, wherein each aliquot has a volume between 0.2 cc and 1.0 cc.

3. The method of claim 1, wherein the targeted area is a female breast.

4. The method of claim 1, further comprising visually observing a quantity of adipose tissue remaining in the reservoir.

5. The method of claim 1, wherein the pump is a motorized pump, and wherein the injecting step comprises actuating the motorized pump.

6. The method of claim 5, wherein the pump comprises a piston pump.

7. The method of claim 5, wherein the cannula and the reservoir are supported by a handle, the actuating step comprising operating an actuator supported by the handle.

8. The method of claim 1, further comprising monitoring a pump parameter during the injecting step.

9. The method of claim 8, wherein the pump parameter is pump piston position.

10. The method of claim 8, wherein the pump parameter is system pressure.

11. The method of claim 8, further comprising notifying a user of a possible clog based on the monitored pump parameter.

12. The method of claim 1, comprising positioning a plunger of the pump in a primed position to allow the air or debris to escape through the opening associated with the priming bore diameter of the pumping chamber.

13. A method of implanting tissue, comprising:
    inserting a cannula percutaneously along a tract into a targeted area; and
    operating a pump including a pumping chamber to inject a plurality of aliquots of adipose tissue from a tissue reservoir through the cannula into the tract at a pressure between 15 in Hg of vacuum and 51 in Hg of pressure;
    wherein the pumping chamber defines a bore diameter and a priming bore diameter, the bore diameter separating the priming bore diameter from the cannula, the priming bore diameter being disposed at a proximal portion of the pumping chamber, and the priming bore diameter being dimensioned greater than the bore diameter of the pumping chamber; and
    wherein the pumping chamber includes an opening formed in a wall of the pumping chamber at the priming bore diameter configured for ejection of air or debris from the pumping chamber.

14. The method of claim 13, wherein the aliquots comprise aliquots of a first volume, the method further comprising changing the pump operation to inject a plurality of aliquots of a second volume, the second volume being different than the first volume.

15. The method of claim 14, wherein the aliquot volumes are between 0.2 cc and 1.0 cc.

16. The method of claim 13, comprising monitoring a pump parameter to identify a pump malfunction or a system clog.

17. The method of claim 16, wherein the pump parameter is pump piston position.

18. The method of claim 16, wherein the pump parameter is system pressure.

19. The method of claim 18, further comprising notifying a user of a possible clog based on the monitored pump parameter.

20. A device for implanting tissue, comprising:
    a handle comprising first and second longitudinally extending gripping surfaces adapted to be held by a user;
    an injection cannula extending longitudinally from a cannula connection point in the handle, the cannula connection point being disposed below and distal to the first and second longitudinally extending gripping surfaces, the cannula being adapted to be inserted into a targeted area of a human body;

an adipose tissue reservoir connected to the handle; and a pump including a pumping chamber disposed in the handle and adapted to pump a plurality of aliquots of adipose tissue from the adipose tissue reservoir into the cannula for delivery into the targeted area;

wherein the pumping chamber defines a bore diameter and a priming bore diameter, the bore diameter separating the priming bore diameter from the cannula, the priming bore diameter being disposed at a proximal portion of the pumping chamber, and the priming bore diameter being dimensioned greater than the bore diameter of the pumping chamber; and wherein the pumping chamber includes an opening formed in a wall of the pumping chamber at the priming bore diameter configured for ejection of air or debris from the pumping chamber.

21. The system of claim 20, further comprising a cannula coupler adapted to detachably couple the cannula to the handle.

22. The system of claim 20, wherein the cannula connection point is disposed in an attachment assembly offset from the handle.

23. The system of claim 22, wherein the attachment assembly comprises a control surface on a proximal portion adapted to receive pressure from a user's finger for leverage in pushing the system in a distal direction.

24. The system of claim 20, wherein the reservoir is disposed above the gripping surfaces.

25. The system of claim 24, wherein the reservoir is adapted to provide visual feedback with respect to a tissue volume remaining within the reservoir during an injection procedure.

26. The system of claim 24, wherein the handle further comprises a control surface disposed between the first gripping surface and the reservoir adapted to receive a user's webbing between the user's thumb and forefinger.

27. The system of claim 20, further comprising a pump actuator supported by the handle and disposed distal to the gripping surfaces and proximal to the cannula.

28. The system of claim 27, wherein the first gripping surface is on a top side of the handle, pump actuator is disposed below the first gripping surface.

29. The system of claim 28, wherein the second gripping surface is on a bottom side of the handle, the handle further comprising a guard extending downward from the second gripping surface and adapted to prevent inadvertent actuation of the pump actuator.

30. The system of claim 20, further comprising a tissue flow path from the pump to the cannula, the tissue flow path comprising a channel extending in a downward angle from an outlet of the pump to an inlet of the cannula.

31. The system of claim 20, wherein the pump comprises first and second chambers and a translatable plunger slideable therethrough.

32. The system of claim 20, wherein the pump is adapted to deliver an aliquot of adipose tissue to the cannula, the system further comprising a controller configured to change the volume of the aliquot to be delivered.

33. The system of claim 32, wherein the aliquot volume is between 0.2 cc and 1.0 cc.

* * * * *